United States Patent
Nam et al.

(10) Patent No.: US 11,213,510 B2
(45) Date of Patent: Jan. 4, 2022

(54) THIOINDIRUBINS

(71) Applicants: City of Hope, Duarte, CA (US); National and Kapodistrian University of Athens, Athens (GR)

(72) Inventors: Sangkil Nam, Tujunga, CA (US); David Horne, Altadena, CA (US); Ravi Salgia, Pasadena, CA (US); Alexios Leandros Skaltsounis, Athens (GR); Nicolas Gaboriaud-Kolar, Athens (GR); Panagiotis Gerolymatos, Athens (GR); Nikolaos Lougiakis, Athens (GR)

(73) Assignees: City of Hope, Duarte, CA (US); National and Kapodistrian University of Athens, Athens (GR)

( * ) Notice: Subject to any disclaimer, the term of this patent is extended or adjusted under 35 U.S.C. 154(b) by 3 days.

(21) Appl. No.: 16/643,051

(22) PCT Filed: Aug. 30, 2018

(86) PCT No.: PCT/US2018/048799
§ 371 (c)(1),
(2) Date: Feb. 28, 2020

(87) PCT Pub. No.: WO2019/046551
PCT Pub. Date: Mar. 7, 2019

(65) Prior Publication Data
US 2020/0345693 A1 Nov. 5, 2020

Related U.S. Application Data

(60) Provisional application No. 62/553,349, filed on Sep. 1, 2017.

(51) Int. Cl.
| | | |
|---|---|---|
| *A61K 31/4025* | (2006.01) | |
| *A61P 35/00* | (2006.01) | |
| *A61K 31/496* | (2006.01) | |
| *A61K 31/5377* | (2006.01) | |
| *A61K 45/06* | (2006.01) | |
| *C07D 409/04* | (2006.01) | |
| *C07D 409/14* | (2006.01) | |
| *C07D 413/14* | (2006.01) | |

(52) U.S. Cl.
CPC ........ *A61K 31/4025* (2013.01); *A61K 31/496* (2013.01); *A61K 31/5377* (2013.01); *A61K 45/06* (2013.01); *A61P 35/00* (2018.01); *C07D 409/04* (2013.01); *C07D 409/14* (2013.01); *C07D 413/14* (2013.01)

(58) Field of Classification Search
None
See application file for complete search history.

(56) References Cited

U.S. PATENT DOCUMENTS

2014/0275168 A1   9/2014   Jove et al.

FOREIGN PATENT DOCUMENTS

| CN | 101747339 B | 4/2012 |
|---|---|---|
| WO | WO-2005/070416 A1 | 8/2005 |

OTHER PUBLICATIONS

Harley-Mason et al., Journal of the Chemical Society (1942), pp. 404-415.*
Database CAPLUS (Acc. No. 1942:36350) CAS SciFinder abstract of Harley-Mason et al., Journal of the Chemical Society (1942), pp. 404-415.*
Meier et al., Liebigs Annalen der Chemie (1981), 7, pp. 1303-1333.*
Database CAPLUS (Acc. No. 1981:517040) CAS SciFiner abstract of Meier et al., Liebigs Annalen der Chemie (1981), 7, pp. 1303-1333.*
International Search Report dated Dec. 18, 2018, for PCT Application No. PCT/US2018/048799, filed Aug. 30, 2018, 4 pages.
Written Opinion dated Dec. 18, 2018, for PCT Application No. PCT/US2018/048799, filed Aug. 30, 2018, 4 pages.

* cited by examiner

*Primary Examiner* — Brian J Davis
(74) *Attorney, Agent, or Firm* — Mintz, Levin, Cohn, Ferris, Glovsky and Popeo, P.C.; Kenneth E. Jenkins; Joohee Lee

(57) ABSTRACT

Disclosed herein inter alia are compositions and methods for treating cancer using thioindirubin derivatives.

32 Claims, No Drawings

THIOINDIRUBINS

CROSS-REFERENCES TO RELATED APPLICATIONS

This application is a U.S. national phase application, pursuant to 35 U.S.C. § 371, of PCT/US2018/048799, filed Aug. 30, 2018, which claims the benefit of priority of U.S. Provisional Application No. 62/553,349 filed on Sep. 1, 2017, which are incorporated herein by reference in their entirety and for all purposes.

BACKGROUND OF THE INVENTION

Cancer is a significant cause of death worldwide. In 2008, cancer accounted for an estimated 13% of worldwide deaths. Lung, prostate, and colorectal cancer are the most common forms of cancer in men and accounted for 40% of all cancers in men in 2008. Breast, colorectal, and cervical cancers made up more than 40% of all cancers in women in the same year. Overall, lung cancer is the most common cancer. Protein kinases are involved in many signal transduction and other cellular processes. Disregulation of kinase activity has been found to be associated with many forms of cancer. Disclosed herein are, inter alia, are solutions to these and other problems in the art, including indirubin derivatives capable of modulating different kinases or single kinases.

BRIEF SUMMARY OF THE INVENTION

Provided herein, inter alia, is a compound, or pharmaceutically acceptable salt thereof, having the formula (I):

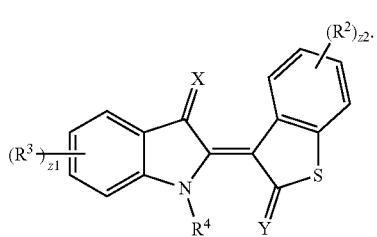

(I)

n1, n2, n3, n4 and n6 are independently an integer from 0 to 4. m2, m3, v1, v2, v3, v4 and v6 are independently 1 or 2. z1 and z2 are independently an integer from 1 to 4.

X is =O, =S or =NR$^1$. Y is =O, =S or =NR$^6$.

R$^1$ is hydrogen, halogen, oxo, CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NRNR$^{2B}$R$^{2C}$, —NHC(O)R$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2_3$, —OCHX$^2_2$, —OCH$_2$X$^2$, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^4$ is hydrogen, halogen, oxo, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^6$ is hydrogen, halogen, oxo, —CX$^6_3$, —CHX$^6_2$, —CH$_2$X$^6$, —N$_3$, —CN, —SO$_{n6}$R$^{6A}$, —SO$_{v6}$NR$^{6B}$R$^{6C}$, —NR$^{6B}$R$^{6C}$, —C(O)R$^{6D}$, —C(O)OR$^{6D}$, C(O)NR$^{6B}$R$^{6C}$, —OR$^{6A}$, —OCX$^6_3$, —OCHX$^6_2$, —OCH$_2$X$^6$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{6A}$, R$^{6B}$, R$^{6C}$ and R$^{6D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1B}$ and R$^{1C}$, R$^{2B}$ and R$^{2C}$, R$^{3B}$ and R$^{3C}$, R$^{4B}$ and R$^{4C}$ and R$^{6B}$ and R$^{6C}$ substituents bonded to the same nitrogen atom may optionally be joined to form a substituted or unsubstituted heterocycloalkyl or substituted or unsubstituted heteroaryl.

X$^1$, X$^2$, X$^3$, X$^4$ and X$^6$ are independently —Cl, —Br, —I or —F.

In embodiments, when X is =O and Y is =O, then at least one of R$^2$, R$^3$ and R$^4$ is not hydrogen.

In embodiments, the compound has structural Formula (I-A):

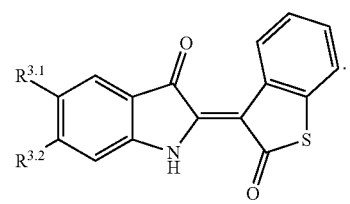

(I-A)

n3.1 and n3.2 are independently an integer from 0 to 4. m3.1, m3.2, v3.1 and v3.2 are independently 1 or 2.

R$^{3.1}$ is hydrogen, halogen, —CX$^{3.1}_3$, —CHX$^{3.1}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}_3$, —OCHX$^{3.1}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. P R$^{3.2}$ is hydrogen, halogen, —CX$^{3.2}_3$, —CHX$^{3.2}_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^{3.1A}$, R$^{3.1B}$, R$^{3.1C}$, R$^{3.1D}$, R$^{3.2A}$, R$^{3.2B}$, R$^{3.2C}$ and R$^{3.2D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{3.1B}$ and R$^{3.1C}$ and R$^{3.2B}$ and R$^{3.2C}$ substituents bonded to the same nitrogen atom may optionally be joined to form a substituted or unsubstituted heterocycloalkyl or substituted or unsubstituted heteroaryl.

X$^{3.1}$ and X$^{3.2}$ are independently —Cl, —Br, —I or —F.

In embodiments, the compound has structural Formula (I-B):

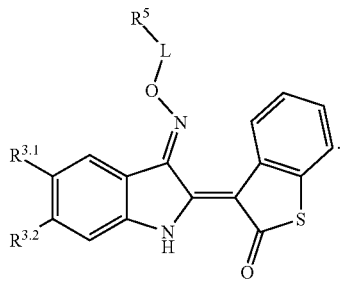

(I-B)

R$^{3.1}$ and R$^{3.2}$ are as described above.

L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

R$^5$ is hydrogen, halogen, —CX$^5_3$, —CHX$^5_2$, —CH$_2$X$^5$, —CN, —N$_3$, —SO$_5$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^5_3$, —OCHX$^5_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{5A}$, R$^{5B}$, R$^{5C}$ and R$^{5D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{5B}$ and R$^{5C}$ substituents bonded to the same nitrogen atom may optionally be joined to form a substituted or unsubstituted heterocycloalkyl or substituted or unsubstituted heteroaryl. n5 is independently an integer from 0 to 4. m5, and v5 are independently 1 or 2. X$^5$ is independently —Cl, —Br, —I or —F.

In embodiments, the compound is:

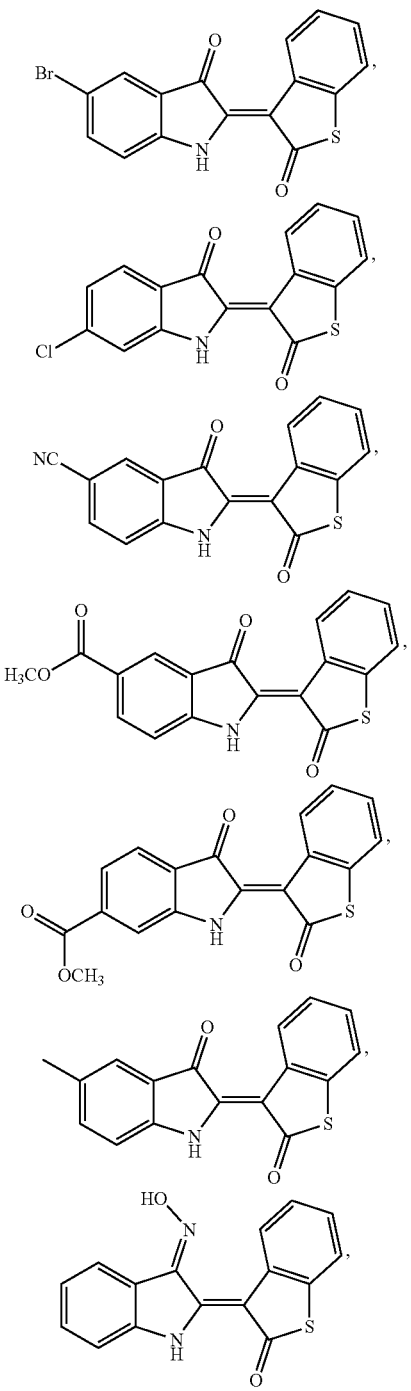

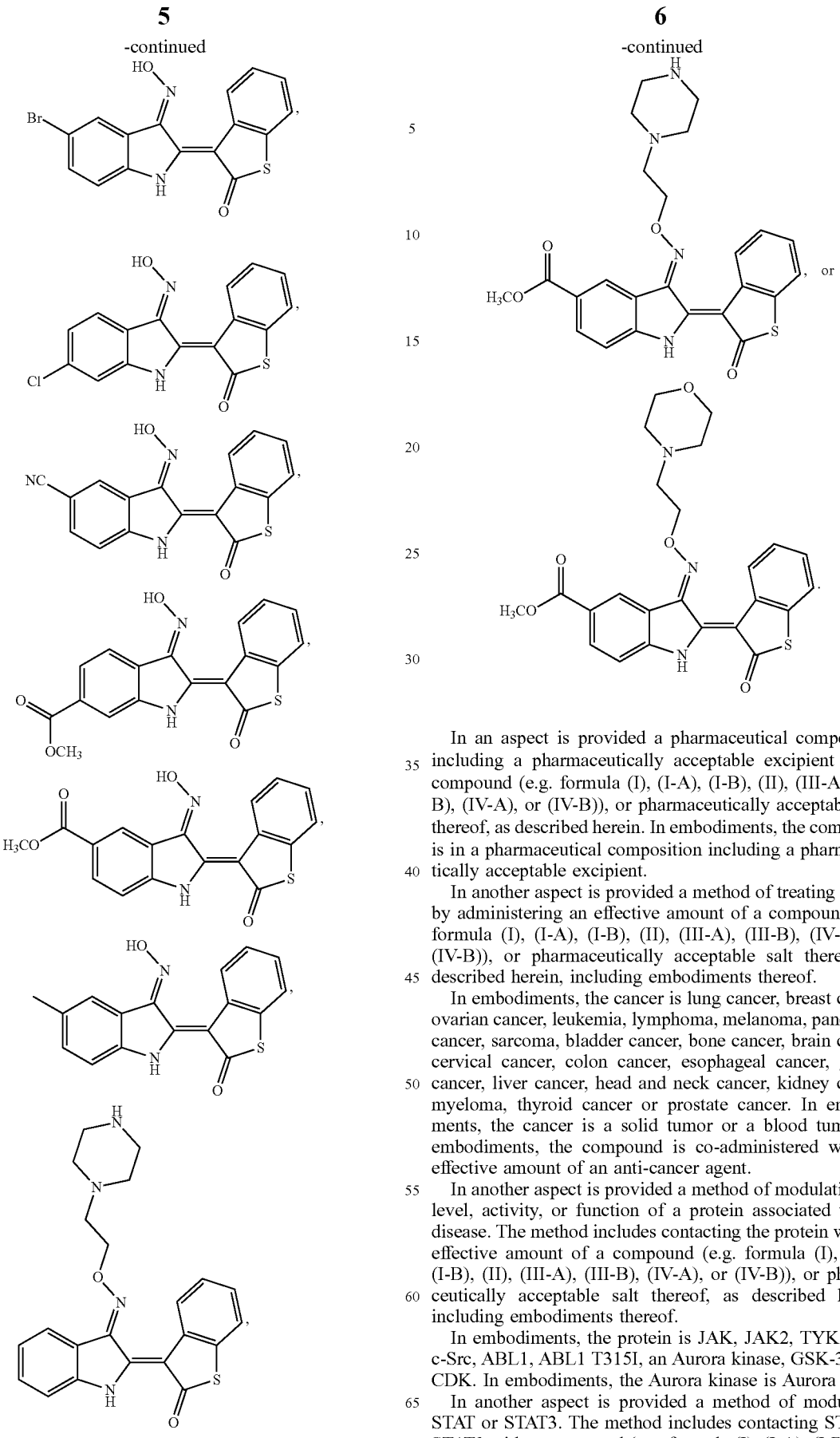

In an aspect is provided a pharmaceutical composition including a pharmaceutically acceptable excipient and a compound (e.g. formula (I), (I-A), (I-B), (II), (III-A), (III-B), (IV-A), or (IV-B)), or pharmaceutically acceptable salt thereof, as described herein. In embodiments, the compound is in a pharmaceutical composition including a pharmaceutically acceptable excipient.

In another aspect is provided a method of treating cancer by administering an effective amount of a compound (e.g. formula (I), (I-A), (I-B), (II), (III-A), (III-B), (IV-A), or (IV-B)), or pharmaceutically acceptable salt thereof, as described herein, including embodiments thereof.

In embodiments, the cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer or prostate cancer. In embodiments, the cancer is a solid tumor or a blood tumor. In embodiments, the compound is co-administered with an effective amount of an anti-cancer agent.

In another aspect is provided a method of modulating the level, activity, or function of a protein associated with a disease. The method includes contacting the protein with an effective amount of a compound (e.g. formula (I), (I-A), (I-B), (II), (III-A), (III-B), (IV-A), or (IV-B)), or pharmaceutically acceptable salt thereof, as described herein, including embodiments thereof.

In embodiments, the protein is JAK, JAK2, TYK2, Src, c-Src, ABL1, ABL1 T315I, an Aurora kinase, GSK-3b or a CDK. In embodiments, the Aurora kinase is Aurora A.

In another aspect is provided a method of modulating STAT or STAT3. The method includes contacting STAT or STAT3 with a compound (e.g. formula (I), (I-A), (I-B), (II), (III-A), (III-B), (IV-A), or (IV-B)) as described herein, or pharmaceutically acceptable salt thereof.
In embodiments, the compound in the pharmaceutical compositions and methods as described herein is:
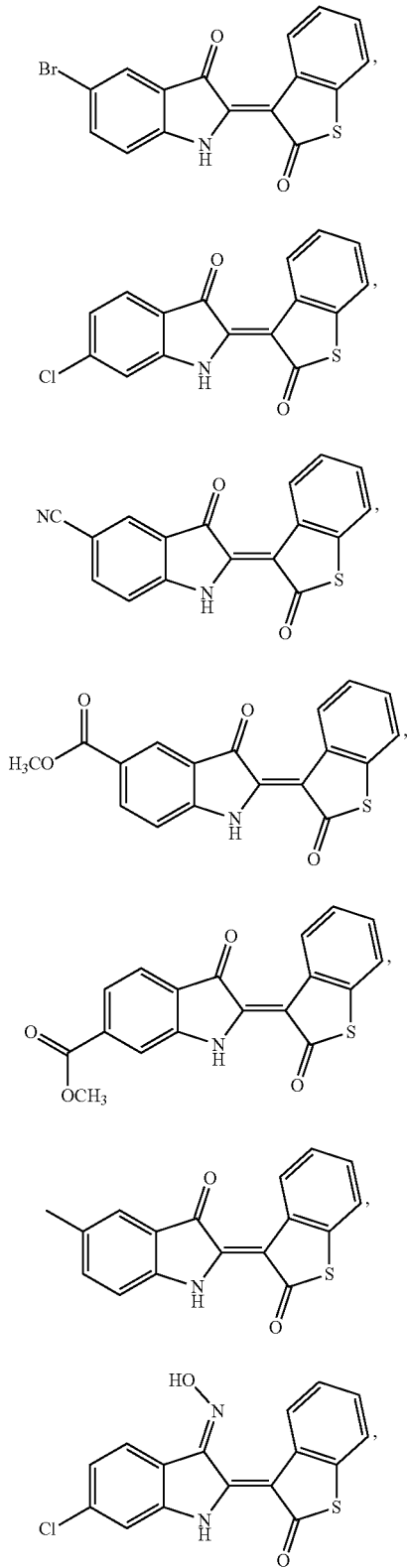
-continued
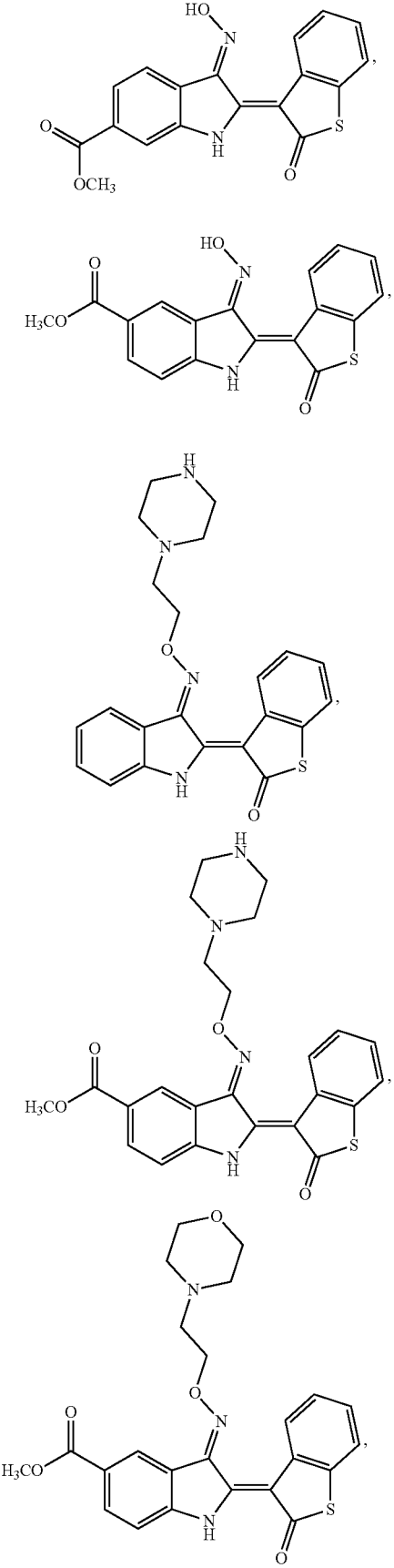

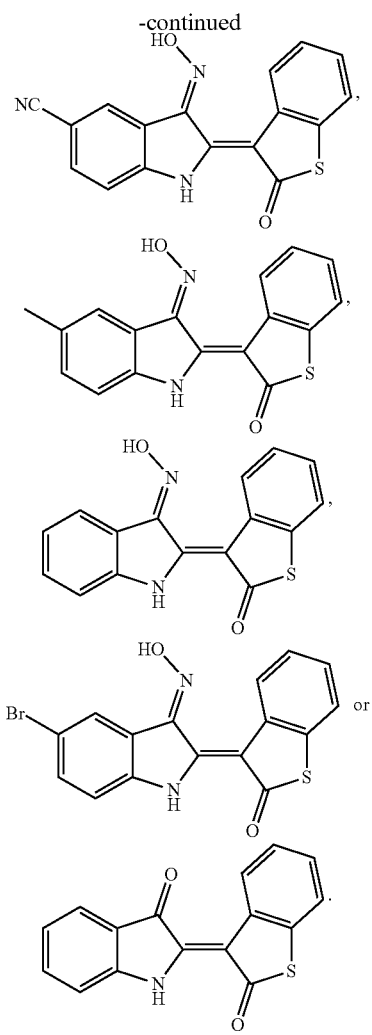

Other aspects of the invention are disclosed infra.

DETAILED DESCRIPTION OF THE INVENTION

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbon atoms (e.g. C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P).

A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, biphenyl, pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl.

Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different.

Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH2Br, —OCH$_2$I, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments of the compounds herein, each substituted or unsubstituted alkyl may be a substituted (e.g., substituted with a substituent group, a size-limited substituent group, or a lower substituent group) or unsubstituted $C_1$-$C_{20}$ alkyl, each substituted or unsubstituted heteroalkyl is a substituted (e.g., substituted with a substituent group, a size-limited substituent group, or a lower substituent group) or unsubstituted 2 to 20 membered heteroalkyl, each substituted or unsubstituted cycloalkyl is a substituted (e.g., substituted with a substituent group, a size-limited substituent group, or a lower substituent group) or unsubstituted $C_3$-$C_8$ cycloalkyl, each substituted or unsubstituted heterocycloalkyl is a substituted (e.g., substituted with a substituent group, a size-limited substituent group, or a lower substituent group) or unsubstituted 3 to 8 membered heterocycloalkyl, each or unsubstituted aryl is a substituted (e.g., substituted with a substituent group, a size-limited substituent group, or a lower substituent group) or unsubstituted $C_6$-$C_{10}$ aryl, and/or each substituted or unsubstituted heteroaryl is a substituted (e.g., substituted with a substituent group, a size-limited substituent group, or a lower substituent group) or unsubstituted 5 to 10 membered heteroaryl. In embodiments herein, each substituted or unsubstituted alkylene is a substituted (e.g., substituted with a substituent group, a size-limited substituent group, or a lower substituent group) or unsubstituted $C_1$-$C_{20}$ alkylene, each substituted or unsubstituted heteroalkylene is a substituted (e.g., substituted with a substituent group, a size-limited substituent group, or a lower substituent group) or unsubstituted 2 to 20 membered heteroalkylene, each substituted or unsubstituted cycloalkylene is a substituted (e.g., substituted with a substituent group, a size-limited substituent group, or a lower substituent group) or unsubstituted $C_3$-$C_8$ cycloalkylene, each substituted or unsubstituted heterocycloalkylene is a substituted (e.g., substituted with a substituent group, a size-limited substituent group, or a lower substituent group) or unsubstituted 3 to 8 membered heterocycloalkylene, each substituted or unsubstituted arylene is a substituted (e.g., substituted with a substituent group, a size-limited substituent group, or a lower substituent group) or unsubstituted $C_6$-$C_{10}$ arylene, and/or each substituted or unsubstituted heteroarylene is a substituted (e.g., substituted with a substituent group, a size-limited substituent group, or a lower substituent group) or unsubstituted 5 to 10 membered heteroarylene.

In some embodiments, each substituted or unsubstituted alkyl is a substituted (e.g., substituted with a substituent group, a size-limited substituent group, or a lower substituent group) or unsubstituted $C_1$-$C_8$ alkyl, each substituted or unsubstituted heteroalkyl is a substituted (e.g., substituted with a substituent group, a size-limited substituent group, or a lower substituent group) or unsubstituted 2 to 8 membered heteroalkyl, each substituted or unsubstituted cycloalkyl is a substituted (e.g., substituted with a substituent group, a size-limited substituent group, or a lower substituent group) or unsubstituted $C_3$-$C_7$ cycloalkyl, each substituted or unsubstituted heterocycloalkyl is a substituted (e.g., substituted with a substituent group, a size-limited substituent group, or a lower substituent group) or unsubstituted 3 to 7 membered heterocycloalkyl, each substituted or unsubstituted aryl is a substituted (e.g., substituted with a substituent group, a size-limited substituent group, or a lower substituent group) or unsubstituted $C_6$-$C_{10}$ aryl, and/or each substituted or unsubstituted heteroaryl is a substituted (e.g., substituted with a substituent group, a size-limited substituent group, or a lower substituent group) or unsubstituted 5 to 9 membered heteroaryl. In some embodiments, each substituted or unsubstituted alkylene is a substituted (e.g., substituted with a substituent group, a size-limited substituent group, or a lower substituent group) or unsubstituted $C_1$-$C_8$ alkylene, each substituted or unsubstituted heteroalkylene is a substituted (e.g., substituted with a substituent group, a size-limited substituent group, or a lower substituent group) or unsubstituted 2 to 8 membered heteroalkylene, each substituted or unsubstituted cycloalkylene is a substituted (e.g., substituted with a substituent group, a size-limited substituent group, or a lower substituent group) or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted (e.g., substituted with a substituent group, a size-limited substituent group, or a lower substituent group) or unsubstituted $C_6$-$C_{10}$ arylene, and/or each substituted or unsubstituted heteroarylene is a substituted (e.g., substituted with a substituent group, a size-limited substituent group, or a lower substituent group) or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "∽" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, reduce one or more symptoms of a disease or condition, reduce the level of a kinase activity in a cell (e.g. JAK2, Src, STAT3, ABL1, T315I mutant ABL1, TYK2, Aurora A, cylin dependent kinase, or GSK-3β). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"JAK" or "Janus Kinase" as used herein refers to a protein including nonreceptor tyrosine kinases for tranducing cytokine-mediated signals via the JAK-STAT pathway. For example, "JAK1" or "Janus kinase 1" as used herein refers to a protein identified, for example, as UniProt ID: P23458, P52332 or Q09178 or isoforms thereof. "JAK2" or "Janus kinase 2" as used herein refers to a protein identified, for example, as UniProt ID: O60674, Q62689, or Q62120 or isoforms thereof.

"Src" as used herein refers to a protein identified, for example, as UniProt ID: P12931, P05480, or Q9WUD9 or isoforms thereof.

"STAT3" as used herein refers to a protein identified, for example, as UniProt ID: P40763, P42227, or P52631 or isoforms thereof.

"ABL1" as used herein refers to a protein identified, for example, as UniProt ID: P00519, P00520, or Q3SYK5 or isoforms thereof. "T315I mutant ABL" or "ABL1 T315I" as used herein refers to a protein having a mutation at T (threonine) site at $315^{th}$ amino acid into I (isoleucine) in ABL1 propteins or homologous proteins thereof.

"TYK2" as used herein refers to a protein identified, for example, as UniProt ID: P29597, Q9R117, or D3ZD03 or isoforms thereof.

"Aurora kinase" as used herein refers to a protein including serine/threonine kinases involved in cell proliferation. "Aurora A" as used herein refers to a protein identified, for example, as UniProt ID: P97477, O14965, or P59241 or isoforms thereof.

"Cylin dependent kinase" or "CDK" as used herein refers to a protein involved in regulating the cell cycle, e.g., regulating transcription, mRNA processing, and the differentiation of nerve cells. Cylin dependent kinase may include cyclin-dependent kinase 1 (for example, UniProt ID: P06493, P11440, or P48734) or isoforms thereof, or cyclin-dependent kinase 8 (for example, UniProt ID: P49336, or Q8R3L8) or isoforms thereof.

"GSK-3β" as used herein refers to a protein identified as UniProt ID: P49841, Q9WV60, or P18266 or isoforms thereof.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch.

It should be appreciated, however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. JAK, JAK2, TYK2, Src, c-Src, ABL1, ABL1 T315I, an Aurora kinase (e.g. Aurora A), GSK-3b or a CDK). In embodiments contacting includes allowing a compound described herein to interact with a protein or enzyme that is involved in a signaling pathway (e.g. STAT or STAT3 pathway).

As defined herein, the term "inhibition", "inhibit", "inhibiting" and the like in reference to a protein-inhibitor interaction means negatively affecting (e.g. decreasing) the activity or function of the protein (e.g. decreasing the phosphorylation of another protein by a kinase) relative to the activity or function of the protein (e.g. kinase) in the absence of the inhibitor (e.g. kinase inhibitor or kinase inhibitor compound). In embodiments inhibition refers to reduction of a disease or symptoms of disease. In embodiments, inhibition refers to a reduction in the activity of a signal transduction pathway or signaling pathway (e.g. reduction of a pathway involving JAK, JAK2, TYK2, Src, c-Src, ABL1, ABL1 T315I, an Aurora kinase (e.g. Aurora A), GSK-3b, CDK, STAT, or STAT3). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. JAK, JAK2, TYK2, Src, c-Src, ABL1, ABL1 T315I, an Aurora kinase (e.g. Aurora A), GSK-3b, CDK, STAT, or STAT3). In embodiments, JAK, JAK2, TYK2, Src, c-Src, ABL1, ABL1 T315I, an Aurora kinase (e.g. Aurora A), GSK-3b, CDK, STAT, or STAT3 is a human protein.

The term "modulator" refers to a composition that increases or decreases the level of a target molecule or the function of a target molecule (e.g. a target may be a kinase (e.g. JAK, JAK2, TYK2, Src, c-Src, ABL1, ABL1 T315I, an Aurora kinase (e.g. Aurora A), GSK-3b or a CDK) and the function may be to phosphorylate a molecule or the target may be a kinase (e.g. JAK, JAK2, TYK2, Src, c-Src, ABL1, ABL1 T315I, an Aurora kinase (e.g. Aurora A), GSK-3b or a CDK) and the function may be the function of a downstream signaling pathway including a STAT or STAT3. In embodiments, a kinase modulator is a compound that reduces the activity of a kinase in a cell. A kinase modulator may reduce the activity of one kinase but cause an increase in enzyme activity of another kinase that results in a reduction or increase, respectively, of cell growth and proliferation. In embodiments, a kinase disease modulator is a compound that reduces the severity of one or more symptoms of a disease associated with the kinase (e.g. cancer).

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human.

"Disease" or "condition" refer to a state of being or health status of a patient or subject capable of being treated with a compound, pharmaceutical composition, or method provided herein. In embodiments, the disease is a disease related to (e.g. caused by) an activated or overactive kinase or aberrant kinase activity as described herein. In embodiments, the disease is a disease related to (e.g. characterized by) an inhibited kinase or reduced kinase activity (e.g. cancer with decreased level of JAK, JAK2, TYK2, Src, c-Src, ABL1, ABL1 T315I, an Aurora kinase (e.g. Aurora A), GSK-3b or a CDK activity or decreased signal transduction activity in pathways involving JAK, JAK2, TYK2, Src, c-Src, ABL1, ABL1 T315I, an Aurora kinase (e.g. Aurora A), GSK-3b, CDK, STAT, or STAT3). Examples of diseases, disorders, or conditions include, but are not limited to, cancer, lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma. In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Stenberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "associated" or "associated with" in the context of a substance or substance activity or function associated with a disease (e.g. a protein associated disease, a cancer associated with aberrant kinase activity) means that the disease (e.g. cancer) is caused by (in whole or in part), or a symptom of the disease is caused by (in whole or inpart) the substance or substance activity or function. For example, a cancer associated with aberrant kinase activity or function may be a cancer that results (entirely or partially) or is otherwise characterized by aberrant kinase activity or function (e.g. enzyme activity, protein-protein interaction, signaling pathway) or a cancer wherein a particular symptom of the disease is caused (entirely or partially) by aberrant kinase activity or function. As used herein, what is described as being associated with a disease, if a causative agent, could be a target for treatment of the disease. For example, a cancer associated with aberrant kinase activity or function or a kinase associated cancer, may be treated with a kinase modulator or kinase inhibitor, in the instance where increased kinase activity or function (e.g. signaling pathway activity) causes the cancer.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a kinase with a compound as described herein may result in a change in one or more protein-protein interactions of the kinase, resulting in changes in cell growth, proliferation, or survival.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

The compounds described herein can be used in combination with one another, with other active agents known to be useful in treating a disease associated with cells expressing a particular kinase as described herein, or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another.

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The compositions of the present invention can also be delivered as microspheres for slow release in the body. For example, microspheres can be administered via intradermal injection of drug-containing microspheres, which slowly release subcutaneously (see Rao, *J. Biomater. Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J Hosp. Pharm.* 46:1576-1587, 1989).

Pharmaceutical compositions provided by the present invention include compositions wherein the active ingredient (e.g. compounds described herein, including embodiments thereof) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule such as a kinase described herein, and/or reducing, eliminating, or slowing the progression of disease symptoms (e.g. cancer growth or metastasis). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. cancer, lung cancer, breast cancer, ovarian cancer, leukemia, melanoma, pancreatic cancer, or prostate cancer), kind of concurrent treatment, complications from the disease being treated or other health-related problems. Other therapeutic regimens or agents can be used in conjunction with the methods and compounds of Applicants' invention.

Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318026, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142266, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride;

pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9265B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-62638 (Asta Medica), D-62636 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE726, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$Sn, $^{149}$Pm, $^{153}$Sm, $^{166}$Ho, $^{177}$Lu, $^{186}$Re, $^{126}$Re, $^{211}$At, and $^{212}$Bi, optionally conjugated to antibodies directed against tumor antigens.

I. COMPOSITIONS

In an aspect is provided a compound, or pharmaceutically acceptable salt thereof, having the formula:

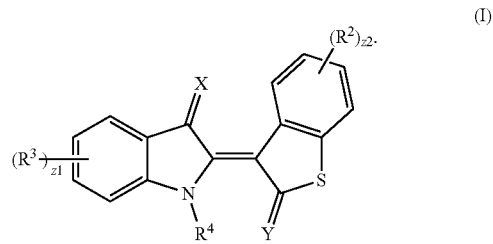

(I)

z1 and z2 are independently an integer from 1 to 4. X is =O, =S or =NR$^1$. Y is =O, =S or =NR$^6$.

R$^1$ is hydrogen, halogen, oxo, —CX$^{13}$, —CHX$^{12}$, —CH$_2$X$^1$, —N$_3$, —CN, —SO$_{n1}$R$^{1A}$, SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2_3$, —OCHX$^2_2$, —OCH$_2$X$^2$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or unsubstituted aryl or substituted or unsubstituted heteroaryl.

R$^4$ is hydrogen, halogen, oxo, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^{4}_{3}$, —OCHX$^{4}_{2}$, —OCH$_2$X$^{4}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^6$ is hydrogen, halogen, oxo, —CX$^{63}$, —CHX$^{62}$, —CH$_2$X$^6$, —N$_3$, —CN, —SO$_{n6}$R$^{6A}$, SO$_{v6}$NR$^{6B}$R$^{6C}$, —NR$^{6B}$R$^{6C}$, —C(O)R$^{6D}$, —C(O)OR$^{6D}$, —C(O)NR$^{6B}$R$^{6C}$, —OR$^{6A}$, —OCX$^{63}$, —OCHX$^{6}_{2}$, —OCH$_2$X$^{6}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{6A}$, R$^{6B}$, R$^{6C}$ and R$^{6D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{1B}$ and R$^{1C}$ together with atoms attached thereto are optionally joined to form substituted or unsubstituted heterocycloalkyl, or substituted or unsubstituted heteroaryl. R$^{2B}$ and R$^{2C}$ together with atoms attached thereto are optionally joined to form substituted or unsubstituted heterocycloalkyl, or substituted or unsubstituted heteroaryl. R$^{3B}$ and R$^{3C}$ together with atoms attached thereto are optionally joined to form substituted or unsubstituted heterocycloalkyl, or substituted or unsubstituted heteroaryl. R$^{4B}$ and R$^{4C}$ together with atoms attached thereto are optionally joined to form substituted or unsubstituted heterocycloalkyl, or substituted or unsubstituted heteroaryl. R$^{6B}$ and R$^{6C}$ substituents bonded to the same nitrogen atom may optionally be joined to form a substituted or unsubstituted heterocycloalkyl or substituted or unsubstituted heteroaryl.

X$^1$, X$^2$, X$^3$, X$^4$ and X$^6$ are independently —Cl, —Br, —I or —F. n1, n2, n3, n4 and n6 are independently an integer from 0 to 4. m2, m3, v1, v2, v3, v4 and v6 are independently 1 or 2.

In embodiments, when X is =O, Y is =O, then at least one of R$^2$, R$^3$ and R$^4$ is not hydrogen.

In embodiments, z1 is 1. In embodiments, z1 is 2. In embodiments, z1 is 3. In embodiments, z1 is 4. In embodiments, z2 is 1. In embodiments, z2 is 2. In embodiments, z2 is 3. In embodiments, z2 is 4.

In embodiments, R$^4$ is hydrogen. In embodiments, R$^4$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, or —CH$_2$I. In embodiments, R$^4$ is —CN. In embodiments, R$^4$ is —SH, —SCH$_3$, —SO$_2$H or —SO$_2$CH$_3$. In embodiments, R$^4$ is —C(O)H, — or C(O)CH$_3$. In embodiments, R$^4$ is —C(O)OH, or —C(O)OCH$_3$). In embodiments, R$^4$ is —C(O)NH$_2$. In embodiments, R$^4$ is —OH, or —OCH$_3$. In embodiments, R4 is —OCF$_3$, —OCCl$_3$, —OCBr$_3$, —OCI$_3$, —OCHF$_2$, —OCHCl$_2$, —OCHBr$_2$, or —OCHI$_2$.

In embodiments, R$^4$ is substituted or unsubstituted alkyl. In embodiments, R$^4$ is substituted or unsubstituted C$_1$-C$_{12}$ alkyl. In embodiments, R$^4$ is substituted or unsubstituted C$_1$-C$_8$ alkyl. In embodiments, R$^4$ is substituted or unsubstituted C$_1$-C$_6$ alkyl. In embodiments, R$^4$ is substituted or unsubstituted C$_1$-C$_4$ alkyl. In embodiments, R$^4$ is substituted or unsubstituted C$_1$-C$_2$ alkyl. In embodiments, R$^4$ is substituted methyl. In embodiments, R$^4$ is unsubstituted methyl. In embodiments, R$^4$ is substituted ethyl. In embodiments, R$^4$ is unsubstituted ethyl.

In embodiments, X is =O. In embodiments, X is =S. In embodiments, X is =NR.

In embodiments, R$^1$ is hydrogen. In embodiments, R$^1$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, or —CH$_2$I. In embodiments, R$^1$ is —CN. In embodiments, R is —SH, —SCH$_3$, —SO$_2$H or —SO$_2$CH$_3$. In embodiments, R$^1$ is —C(O)H, -or C(O)CH$_3$. In embodiments, R$^1$ is —C(O)OH, or —C(O)OCH$_3$). In embodiments, R$^1$ is —C(O)NH$_2$. In embodiments, R$^1$ is —OH, or —OCH$_3$. In embodiments, R is —OCF$_3$, —OCCl$_3$, —OCBr$_3$, —OCI$_3$, —OCHF$_2$, —OCHCl$_2$, —OCHBr$_2$, or —OCHI$_2$.

In embodiments, R$^1$ is substituted or unsubstituted alkyl. In embodiments, R$^1$ is substituted or unsubstituted C$_1$-C$_{12}$ alkyl. In embodiments, R$^1$ is substituted or unsubstituted C$_1$-C$_8$ alkyl. In embodiments, R$^1$ is substituted or unsubstituted C$_1$-C$_6$ alkyl. In embodiments, R$^1$ is substituted or unsubstituted C$_1$-C$_4$ alkyl. In embodiments, R$^1$ is substituted or unsubstituted C$_1$-C$_2$ alkyl. In embodiments, R$^1$ is substituted methyl. In embodiments, R$^1$ is unsubstituted methyl. In embodiments, R$^1$ is substituted ethyl. In embodiments, R$^1$ is unsubstituted ethyl.

In embodiments, R$^1$ is substituted or unsubstituted 2 to 8 membered heteroalkyl. In embodiments, R$^1$ is substituted or unsubstituted 2 to 6 membered heteroalkyl. In embodiments, R$^1$ is substituted or unsubstituted 4 to 6 membered heteroalkyl. In embodiments, R$^1$ is substituted or unsubstituted 2 to 3 membered heteroalkyl. In embodiments, R$^1$ is substituted or unsubstituted 4 to 5 membered heteroalkyl. In embodiments, R$^1$ is substituted or unsubstituted 2 membered heteroalkyl. In embodiments, R$^1$ is substituted or unsubstituted 3 membered heteroalkyl. In embodiments, R$^1$ is substituted or unsubstituted 4 membered heteroalkyl. In embodiments, R$^1$ is substituted or unsubstituted 5 membered heteroalkyl. In embodiments, R$^1$ is substituted or unsubstituted 6 membered heteroalkyl.

In embodiments, R$^1$ is —OR$^A$. In embodiments, R1 is hydrogen. In embodiments, R$^{1A}$ is substituted or unsubstituted alkyl. In embodiments, R$^{1A}$ is substituted or unsubstituted C$_1$-C$_{12}$ alkyl. In embodiments, R$^{1A}$ is substituted or unsubstituted C$_1$-C$_8$ alkyl. In embodiments, R$^1$ is substituted or unsubstituted C$_1$-C$_6$ alkyl. In embodiments, R$^{1A}$ is substituted or unsubstituted C$_1$-C$_4$ alkyl. In embodiments, R$^{1A}$ is substituted or unsubstituted C$_1$-C$_2$ alkyl. In embodiments, R$^{1A}$ is substituted methyl. In embodiments, R$^{1A}$ is unsubstituted methyl. In embodiments, R$^{1A}$ is substituted ethyl. In embodiments, R$^{1A}$ is unsubstituted ethyl.

In embodiments, R$^{1A}$ is substituted or unsubstituted 5 to 6 membered heterocycloalkyl-substituted ethyl. In embodiments, R$^{1A}$ is substituted 5 to 6 membered heterocycloalkyl-substituted ethyl. In embodiments, R$^{1A}$ is unsubstituted 5 to 6 membered heterocycloalkyl-substituted ethyl. In embodiments, R$^{1A}$ is substituted or unsubstituted 5 membered heterocycloalkyl-substituted ethyl. In embodiments, R$^{1A}$ is substituted 5 membered heterocycloalkyl-substituted ethyl. In embodiments, R$^{1A}$ is unsubstituted 5 membered heterocycloalkyl-substituted ethyl. In embodiments, R$^{1A}$ is substituted or unsubstituted 6 membered heterocycloalkyl-substituted ethyl. In embodiments, R$^{1A}$ is substituted 6 membered heterocycloalkyl-substituted ethyl. In embodiments, R$^{1A}$ is unsubstituted 6 membered heterocycloalkyl-substituted ethyl. In embodiments, R$^{1A}$ is substituted or unsubstituted piperazinyl-substituted ethyl. In embodiments, R$^{1A}$ is substituted piperazinyl-substituted ethyl. In embodiments, R$^{1A}$ is unsubstituted piperazinyl-substituted ethyl. In embodiments, R$^{1A}$ is substituted or unsubstituted morpholinyl-substituted ethyl. In embodiments, R$^{1A}$ is substituted morpholinyl-substituted ethyl. In embodiments, $R^{1A}$ is unsubstituted morpholinyl-substituted ethyl.

In embodiments, Y is =O. In embodiments, Y is =S. In embodiments, Y is =NR$^6$.

In embodiments, $R^6$ is hydrogen. In embodiments, $R^6$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, or —CH$_2$I. In embodiments, $R^6$ is —CN. In embodiments, $R^6$ is —SH, —SCH$_3$, —SO$_2$H or —SO$_2$CH$_3$. In embodiments, $R^6$ is —C(O)H, -or C(O)CH$_3$. In embodiments, $R^6$ is —C(O)OH, or —C(O)OCH$_3$). In embodiments, $R^6$ is —C(O)NH$_2$. In embodiments, $R^6$ is —OH, or —OCH$_3$. In embodiments, $R^6$ is —OCF$_3$, —OCCl$_3$, —OCBr$_3$, —OCI$_3$, —OCHF$_2$, —OCHCl$_2$, —OCHBr$_2$, or —OCHI$_2$.

In embodiments, $R^6$ is substituted or unsubstituted alkyl. In embodiments, $R^6$ is substituted or unsubstituted $C_1$-$C_{12}$ alkyl. In embodiments, $R^6$ is substituted or unsubstituted $C_1$-$C_8$ alkyl. In embodiments, $R^6$ is substituted or unsubstituted $C_1$-$C_6$ alkyl. In embodiments, $R^6$ is substituted or unsubstituted $C_1$-$C_4$ alkyl. In embodiments, $R^6$ is substituted or unsubstituted $C_1$-$C_2$ alkyl. In embodiments, $R^6$ is substituted methyl. In embodiments, $R^6$ is unsubstituted methyl. In embodiments, $R^6$ is substituted ethyl. In embodiments, $R^6$ is unsubstituted ethyl.

In embodiments, $R^6$ is substituted or unsubstituted 2 to 8 membered heteroalkyl. In embodiments, $R^6$ is substituted or unsubstituted 2 to 6 membered heteroalkyl. In embodiments, $R^6$ is substituted or unsubstituted 4 to 6 membered heteroalkyl. In embodiments, $R^6$ is substituted or unsubstituted 2 to 3 membered heteroalkyl. In embodiments, $R^6$ is substituted or unsubstituted 4 to 5 membered heteroalkyl. In embodiments, $R^6$ is substituted or unsubstituted 2 membered heteroalkyl. In embodiments, $R^6$ is substituted or unsubstituted 3 membered heteroalkyl. In embodiments, $R^6$ is substituted or unsubstituted 4 membered heteroalkyl. In embodiments, $R^6$ is substituted or unsubstituted 5 membered heteroalkyl. In embodiments, $R^6$ is substituted or unsubstituted 6 membered heteroalkyl.

In embodiments, the compound has structural Formula (I-A):

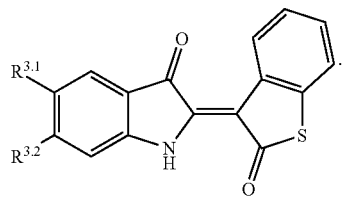

(I-A)

$R^{3.1}$ is hydrogen, halogen, —CX$^{3.1}$$_3$, —CHX$^{3.1}$$_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}$$_3$, —OCHX$^{3.1}$$_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{3.2}$ is hydrogen, halogen, —CX$^{3.2}$$_3$, —CHX$^{3.2}$$_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}$$_3$, —OCHX$^{3.2}$$_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3.1B}$ and $R^{3.1C}$ and $R^{3.2B}$ and $R^{3.2C}$ substituents bonded to the same nitrogen atom may optionally be joined to form a substituted or unsubstituted heterocycloalkyl or substituted or unsubstituted heteroaryl. $X^{3.1}$ and $X^{3.2}$ are independently —Cl, —Br, —I or —F. n3.1 and n3.2 are independently an integer from 0 to 4. m3.1, m3.2, v3.1 and v3.2 are independently 1 or 2.

In embodiments, the compound has structural Formula (I-B):

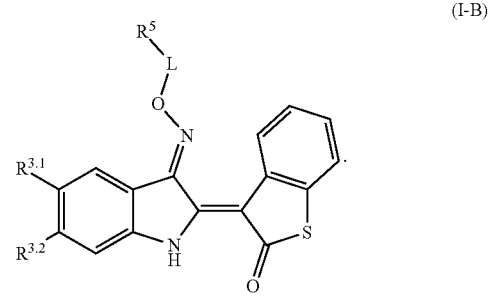

(I-B)

L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

$R^{3.1}$ is hydrogen, halogen, —CX$^{3.1}$$_3$, —CHX$^{3.1}$$_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}$$_3$, —OCHX$^{3.1}$$_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$R^{3.2}$ is hydrogen, halogen, —CX$^{3.2}$$_3$, —CHX$^{3.2}$$_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}$$_3$, —OCHX$^{3.2}$$_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$R^5$ is hydrogen, halogen, —$CX^5{}_3$, —$CHX^{52}$, —$CH_2X^5$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^5{}_3$, —$OCHX^{52}$, —$OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl.

$X^{3.1}$, $X^{3.2}$ and $X^5$ are independently —Cl, —Br, —I or —F. n3.1, n3.2 and n5 are independently an integer from 0 to 4. m3.1, m3.2, m5, v3.1, v3.2 and v5 are independently 1 or 2.

In embodiments, $R^{3.1}$ is hydrogen. In embodiments, $R^{3.1}$ is —F, —Cl, —Br or —I. In embodiments, $R^{3.1}$ is —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, or —$CH_2I$. In embodiments, $R^{3.1}$ is —CN. In embodiments, $R^{3.1}$ is —SH, —$SCH_3$, —$SO_2H$ or —$SO_2CH_3$. In embodiments, $R^{3.1}$ is —C(O)H, -or C(O)$CH_3$. In embodiments, $R^{3.1}$ is —C(O)OH, or —C(O)O$CH_3$. In embodiments, $R^{3.1}$ is —C(O)$NH_2$. In embodiments, $R^{3.1}$ is —OH, or —$OCH_3$. In embodiments, $R^{3.1}$ is —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, or —$OCH_2I$.

In embodiments, $R^{3.1}$ is substituted or unsubstituted alkyl. In embodiments, $R^{3.1}$ is substituted or unsubstituted $C_1$-$C_{12}$ alkyl. In embodiments, $R^{3.1}$ is substituted or unsubstituted $C_1$-$C_8$ alkyl. In embodiments, $R^{3.1}$ is substituted or unsubstituted $C_1$-$C_6$ alkyl. In embodiments, $R^{3.1}$ is substituted or unsubstituted $C_1$-$C_4$ alkyl. In embodiments, $R^{3.1}$ is substituted or unsubstituted $C_1$-$C_2$ alkyl. In embodiments, $R^{3.1}$ is substituted methyl. In embodiments, $R^{3.1}$ is unsubstituted methyl. In embodiments, $R^{3.1}$ is substituted ethyl. In embodiments, $R^{3.1}$ is unsubstituted ethyl.

In embodiments, $R^{3.1}$ is substituted or unsubstituted 2 to 8 membered heteroalkyl. In embodiments, $R^{3.1}$ is substituted or unsubstituted 2 to 6 membered heteroalkyl. In embodiments, $R^{3.1}$ is substituted or unsubstituted 4 to 6 membered heteroalkyl. In embodiments, $R^{3.1}$ is substituted or unsubstituted 2 to 3 membered heteroalkyl. In embodiments, $R^{3.1}$ is substituted or unsubstituted 4 to 5 membered heteroalkyl. In embodiments, $R^{3.1}$ is substituted or unsubstituted 2 membered heteroalkyl. In embodiments, $R^{3.1}$ is substituted or unsubstituted 3 membered heteroalkyl. In embodiments, $R^{3.1}$ is substituted or unsubstituted 4 membered heteroalkyl. In embodiments, $R^{3.1}$ is substituted or unsubstituted 5 membered heteroalkyl. In embodiments, $R^{3.1}$ is substituted or unsubstituted 6 membered heteroalkyl.

In embodiments, $R^{3.2}$ is hydrogen. In embodiments, $R^{3.2}$ is —F, —Cl, —Br or —I. In embodiments, $R^{3.2}$ is —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, or —$CH_2I$. In embodiments, $R^{3.2}$ is —CN. In embodiments, $R^{3.2}$ is —SH, —$SCH_3$, —$SO_2H$ or —$SO_2CH_3$. In embodiments, $R^{3.2}$ is —C(O)H, -or C(O)$CH_3$. In embodiments, $R^{3.2}$ is —C(O)OH, or —C(O)O$CH_3$. In embodiments, $R^{3.2}$ is —C(O)$NH_2$. In embodiments, $R^{3.2}$ is —OH, or —$OCH_3$. In embodiments, $R^{3.2}$ is —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, or —$OCH_2I$.

In embodiments, $R^{3.2}$ is substituted or unsubstituted alkyl. In embodiments, $R^{3.2}$ is substituted or unsubstituted $C_1$-$C_{12}$ alkyl. In embodiments, $R^{3.2}$ is substituted or unsubstituted $C_1$-$C_5$ alkyl. In embodiments, $R^{3.2}$ is substituted or unsubstituted $C_1$-$C_6$ alkyl. In embodiments, $R^{3.2}$ is substituted or unsubstituted $C_1$-$C_4$ alkyl. In embodiments, $R^{3.2}$ is substituted or unsubstituted $C_1$-$C_2$ alkyl. In embodiments, $R^{3.2}$ is substituted methyl. In embodiments, $R^{3.2}$ is unsubstituted methyl. In embodiments, $R^{3.2}$ is substituted ethyl. In embodiments, $R^{3.2}$ is unsubstituted ethyl.

In embodiments, $R^{3.2}$ is substituted or unsubstituted 2 to 8 membered heteroalkyl. In embodiments, $R^{3.2}$ is substituted or unsubstituted 2 to 6 membered heteroalkyl. In embodiments, $R^{3.2}$ is substituted or unsubstituted 4 to 6 membered heteroalkyl. In embodiments, $R^{3.2}$ is substituted or unsubstituted 2 to 3 membered heteroalkyl. In embodiments, $R^{3.2}$ is substituted or unsubstituted 4 to 5 membered heteroalkyl. In embodiments, $R^{3.2}$ is substituted or unsubstituted 2 membered heteroalkyl. In embodiments, $R^{3.2}$ is substituted or unsubstituted 3 membered heteroalkyl. In embodiments, $R^{3.2}$ is substituted or unsubstituted 4 membered heteroalkyl. In embodiments, $R^{3.2}$ is substituted or unsubstituted 5 membered heteroalkyl. In embodiments, $R^{3.2}$ is substituted or unsubstituted 6 membered heteroalkyl.

In embodiments, $R^{3.1}$ and $R^{3.2}$ are independently hydrogen, —F, —Cl, —Br, —I, —CN, substituted or unsubstituted alkyl or substituted or unsubstituted heteroalkyl. In embodiments, $R^{3.1}$ and $R^{3.2}$ are independently hydrogen, —F, —Cl, —Br, —I, —CN, substituted or unsubstituted alkyl (e.g., $C_1$-$C_6$, $C_1$-$C_4$, or $C_1$-$C_2$) or substituted or unsubstituted heteroalkyl (e.g. 2 to 6 membered, 4 to 6 membered, 2 to 3 membered, or 4 to 5 membered).

In embodiments, L is a bond. In embodiments, L is substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, L is substituted or unsubstituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, L is substituted or unsubstituted cycloalkylene (e.g., $C_3$-$C_{10}$, $C_3$-$C_8$, $C_3$-$C_6$, $C_4$-$C_6$, or $C_5$-$C_6$). In embodiments, L is substituted or unsubstituted heterocycloalkylene (e.g., 3 to 10 membered, 3 to 8 membered, 3 to 6 membered, 4 to 6 membered, 4 to 5 membered, or 5 to 6 membered). In embodiments, L is substituted or unsubstituted arylene (e.g., $C_6$-$C_{12}$, $C_6$-$C_{10}$, or phenylene). In embodiments, L is substituted or unsubstituted heteroarylene (e.g., 5 to 12 membered, 5 to 10 membered, 5 to 9 membered, or 5 to 6 membered).

In embodiments, L is unsubstituted alkylene (e.g., $C_1$-$C_8$, $C_1$-$C_6$, $C_1$-$C_4$, or $C_1$-$C_2$). In embodiments, L is unsubstituted $C_1$-$C_8$ alkylene. In embodiments, L is unsubstituted $C_1$-$C_4$ alkylene. In embodiments, L is unsubstituted $C_1$-$C_2$ alkylene. In embodiments, L is unsubstituted methylene. In embodiments, L is unsubstituted ethylene.

In embodiments, $R^5$ is hydrogen. In embodiments, $R^5$ is halogen (e.g. —F, —Cl, —Br or —I). In embodiments, $R^5$ is —$CX^5{}_3$, —$CHX^5{}_2$, or —$CH_2X^5$ (e.g. —$CF_3$, —$CHF_2$, —$CH_2F$, —$CCl_3$, —$CHCl_2$, —$CH_2Cl$, —$CBr_3$, —$CHBr_2$, —CH$_2$Br, —CI$_3$, —CHI$_2$, or —CH$_2$I). In embodiments, R$^5$ is —CN. In embodiments, R$^5$ is —SR$^{5A}$ (e.g. —SH, or —SCH$_3$). In embodiments, R$^5$ is —SO$_{ns}$R$^{5A}$ (e.g. —SO$_2$H or —SO$_2$CH$_3$). In embodiments, R$^5$ is —C(O)OR$^{5D}$ (e.g. —C(O)OH, or —C(O)OCH$_3$). In embodiments, R$^5$ is —C(O)OH. In embodiments, R$^5$ is —C(O)NR$^{5B}$R$^{5C}$, (e.g. —C(O)NH$_2$). In embodiments, R$^5$ is —OR$^{5A}$ (e.g. —OH, or —OCH$_3$). In embodiments, R$^5$ is —OH. In embodiments, R$^5$ is —OCX$^5$ (e.g. —OCF$_3$, —OCCl$_3$, —OCBr$_3$, or —OCI$_3$. In embodiments, R$^5$ is —OCHX$^5{}_2$ (e.g. —OCHF$_2$, —OCHCl$_2$, —OCHBr$_2$, or —OCHI$_2$). In embodiments, R$^5$ is —OCH$_2$X$^5$ (e.g. —OCH$_2$F, —OCH$_2$Cl, —OCH$_2$Br$_2$, or —OCH$_2$I). In embodiments, R$^5$ is —NR$^{5B}$R$^{5C}$ (e.g. —NH$_2$ or —NHCH$_3$). In embodiments, R$^5$ is —NHNR$^{5B}$R$^{5C}$, (e.g. —NHNH$_2$ or —NHNHCH$_3$). In embodiments, R$^5$ is —CN. In embodiments, R$^5$ is —OH. In embodiments, R$^5$ is —NH$_2$. In embodiments, R$^5$ is —C(O)OH. In embodiments, R$^5$ is —C(O)NH$_2$. In embodiments, R$^5$ is —NO$_2$. In embodiments, R$^5$ is —SH. In embodiments, R$^5$ is —NHNH$_2$.

In embodiments, R$^5$ is substituted or unsubstituted alkyl (e.g., C$_1$-C$_8$, C$_1$-C$_6$, C$_1$-C$_4$, or C$_1$-C$_2$). In embodiments, R$^5$ is substituted or unsubstituted C$_1$-C$_{12}$ alkyl. In embodiments, R$^5$ is substituted or unsubstituted C$_1$-C$_8$ alkyl. In embodiments, R$^5$ is substituted or unsubstituted C$_1$-C$_6$ alkyl. In embodiments, R$^5$ is substituted or unsubstituted C$_1$-C$_4$ alkyl. In embodiments, R$^5$ is substituted or unsubstituted C$_1$-C$_2$ alkyl. In embodiments, R$^5$ is substituted methyl. In embodiments, R$^5$ is unsubstituted methyl. In embodiments, R$^5$ is substituted ethyl. In embodiments, R$^5$ is unsubstituted ethyl.

In embodiments, R$^5$ is substituted or unsubstituted 2 to 8 membered heteroalkyl. In embodiments, R$^5$ is substituted or unsubstituted 2 to 6 membered heteroalkyl. In embodiments, R$^5$ is substituted or unsubstituted 4 to 6 membered heteroalkyl. In embodiments, R$^5$ is substituted or unsubstituted 2 to 3 membered heteroalkyl. In embodiments, R$^5$ is substituted or unsubstituted 4 to 5 membered heteroalkyl. In embodiments, R$^5$ is substituted or unsubstituted 2 membered heteroalkyl. In embodiments, R$^5$ is substituted or unsubstituted 3 membered heteroalkyl. In embodiments, R$^5$ is substituted or unsubstituted 4 membered heteroalkyl. In embodiments, R$^5$ is substituted or unsubstituted 5 membered heteroalkyl. In embodiments, R$^5$ is substituted or unsubstituted 6 membered heteroalkyl.

In embodiments, R$^5$ is substituted or unsubstituted cycloalkyl (e.g., C$_3$-C$_6$, C$_4$-C$_6$, or C$_5$-C$_6$). In embodiments, R$^5$ is substituted or unsubstituted C$_3$-C$_6$ cycloalkyl. In embodiments, R$^5$ is substituted or unsubstituted C$_4$-C$_6$ cycloalkyl. In embodiments, R$^5$ is substituted or unsubstituted C$_5$-C$_6$ cycloalkyl. In embodiments, R$^5$ is substituted cyclopropyl.

In embodiments, R$^5$ is unsubstituted cyclopropyl. In embodiments, R$^5$ is substituted cyclobutyl. In embodiments, R$^5$ is unsubstituted cyclobutyl. In embodiments, R$^5$ is substituted cyclopentyl. In embodiments, R$^5$ is unsubstituted cyclopentyl. In embodiments, R$^5$ is substituted cyclohexyl. In embodiments, R$^5$ is unsubstituted cyclohexyl.

In embodiments, R$^5$ is substituted or unsubstituted heterocycloalkyl (e.g., 3 to 6 membered, 4 to 6 membered, 4 to 5 membered, or 5 to 6 membered). In embodiments, R$^5$ is substituted or unsubstituted 3 to 6 membered heterocycloalkyl. In embodiments, R$^5$ is substituted or unsubstituted 4 to 6 membered heterocycloalkyl. In embodiments, R$^5$ is substituted or unsubstituted 5 to 6 membered heterocycloalkyl. In embodiments, R$^5$ is substituted 3 membered heterocycloalkyl. In embodiments, R$^5$ is substituted 3 membered heterocycloalkyl. In embodiments, R$^5$ is substituted 4 membered heterocycloalkyl. In embodiments, R$^5$ is unsubstituted 4 membered heterocycloalkyl. In embodiments, R$^5$ is substituted 5 membered heterocycloalkyl. In embodiments, R$^5$ is unsubstituted 5 membered heterocycloalkyl. In embodiments, R$^5$ is substituted 6 membered heterocycloalkyl. In embodiments, R$^5$ is unsubstituted 6 membered heterocycloalkyl. In embodiments, R$^5$ is substituted or unsubstituted piperazinyl. In embodiments, R$^5$ is substituted piperazinyl. In embodiments, R$^5$ is unsubstituted piperazinyl. In embodiments, R$^5$ is substituted or unsubstituted morpholinyl. In embodiments, R$^5$ is substituted morpholinyl. In embodiments, R$^5$ is unsubstituted morpholinyl. In embodiments, R$^5$ is substituted or unsubstituted piperidinyl. In embodiments, R$^5$ is substituted piperidinyl. In embodiments, R$^5$ is unsubstituted piperidinyl.

In embodiments, R$^5$ is substituted or unsubstituted aryl (e.g., C$_6$-C$_{12}$, or phenyl). In embodiments, R$^5$ is substituted phenyl. In embodiments, R$^5$ is unsubstituted phenyl. In embodiments, R$^5$ is substituted or unsubstituted heteroaryl (e.g., 5 to 10 membered, 5 to 9 membered, or 5 to 6 membered). In embodiments, R$^5$ is substituted or unsubstituted 5 to 10 membered heteroaryl. In embodiments, R$^5$ is substituted or unsubstituted 5 to 9 membered heteroaryl. In embodiments, R$^5$ is substituted or unsubstituted 5 to 6 membered heteroaryl. In embodiments, R$^5$ is substituted 5 membered heteroaryl. In embodiments, R$^5$ is unsubstituted 5 membered heteroaryl. In embodiments, R$^5$ is substituted 6 membered heteroaryl. In embodiments, R$^5$ is unsubstituted 6 membered heteroaryl. In embodiments, R$^5$ is substituted 7 membered heteroaryl. In embodiments, R$^5$ is unsubstituted 7 membered heteroaryl. In embodiments, R$^5$ is substituted 8 membered heteroaryl. In embodiments, R$^5$ is unsubstituted 8 membered heteroaryl. In embodiments, R$^5$ is substituted 9 membered heteroaryl. In embodiments, R$^5$ is unsubstituted 9 membered heteroaryl. In embodiments, R$^5$ is substituted 10 membered heteroaryl. In embodiments, R$^5$ is unsubstituted 10 membered heteroaryl.

In embodiments, L is a bond, R$^5$ is hydrogen and R$^{3.1}$ or R$^{3.2}$ is —Cl, —Br, —I or —F. In embodiments, L is a bond, R$^5$ is hydrogen and R$^{3.1}$ is —Cl. In embodiments, L is a bond, R$^5$ is hydrogen and R$^{3.1}$ is —F. In embodiments, L is a bond, R$^5$ is hydrogen and R$^{3.1}$ is —Br. In embodiments, L is a bond, R$^5$ is hydrogen and R$^{3.1}$ is —I. In embodiments, L is a bond, R$^5$ is hydrogen and R$^{3.2}$ is —Cl. In embodiments, L is a bond, R$^5$ is hydrogen and R$^{3.2}$ is —F. In embodiments, L is a bond, R$^5$ is hydrogen and R$^{3.2}$ is —Br. In embodiments, L is a bond, R$^5$ is hydrogen and R$^{3.2}$ is —I.

In embodiments, R$^5$ is —NR$^{5B}$R$^{5C}$. In embodiments, L is substituted or unsubstituted C$_1$-C$_4$ alkylene. In embodiments, L is unsubstituted C$_1$-C$_4$ alkylene. In embodiments, L is substituted or unsubstituted C$_1$-C$_2$ alkylene. In embodiments, L is unsubstituted C$_1$-C$_2$ alkylene. In embodiments, L is unsubstituted methylene and R$^5$ is —NR$^{5B}$R$^{5C}$. In embodiments, L is unsubstituted ethylene and R$^5$ is —NR$^{5B}$R$^{5C}$, In embodiments, R$^{5B}$ and R$^{5C}$ are independently substituted or unsubstituted alkyl (e.g., C$_1$-C$_8$, C$_1$-C$_6$, C$_1$-C$_4$, or C$_1$-C$_2$). In embodiments, R$^{5B}$ and R$^{5C}$ are independently substituted or unsubstituted C$_1$-C$_{12}$ alkyl. In embodiments, R$^{5B}$ and R$^{5C}$ are independently substituted or unsubstituted C$_1$-C$_8$ alkyl. In embodiments, R$^{5B}$ and R$^{5C}$ are independently substituted or unsubstituted C$_1$-C$_6$ alkyl. In embodiments, R$^{5B}$ and R$^{5C}$ are independently substituted or unsubstituted C$_1$-C$_4$ alkyl. In embodiments, R$^{5B}$ and R$^{5C}$ are independently substituted or unsubstituted C$_1$-C$_2$ alkyl. In embodiments, R$^{5B}$ and R$^{5C}$ are independently unsubstituted C$_1$-C$_8$ alkyl. In embodiments, R$^{5B}$ and R$^{5C}$ are independently unsubstituted $C_1$-$C_6$ alkyl. In embodiments, $R^{5B}$ and $R^{5C}$ are independently unsubstituted $C_1$-$C_4$ alkyl. In embodiments, $R^{5B}$ and $R^{5C}$ are independently substituted methyl. In embodiments, $R^{5B}$ and $R^{5C}$ are independently unsubstituted methyl. In embodiments, $R^{5B}$ and $R^{5C}$ are independently substituted ethyl. In embodiments, $R^{5B}$ and $R^{5C}$ are independently unsubstituted ethyl.

In embodiments, $R^{5B}$ and $R^{5C}$ are independently substituted or unsubstituted 2 to 8 membered heteroalkyl. In embodiments, $R^{5B}$ and $R^{5C}$ are independently substituted or unsubstituted 2 to 6 membered heteroalkyl. In embodiments, $R^{5B}$ and $R^{5C}$ are independently substituted or unsubstituted 4 to 5 membered heteroalkyl. In embodiments, $R^{5B}$ and $R^{5C}$ are independently substituted or unsubstituted 2 to 3 membered heteroalkyl. In embodiments, $R^{5B}$ and $R^{5C}$ are independently substituted or unsubstituted 4 to 5 membered heteroalkyl. In embodiments, $R^{5B}$ and $R^{5C}$ are independently substituted or unsubstituted 2 membered heteroalkyl. In embodiments, $R^{5B}$ and $R^{5C}$ are independently substituted or unsubstituted 3 membered heteroalkyl. In embodiments, $R^{5B}$ and $R^{5C}$ are independently substituted or unsubstituted 4 membered heteroalkyl. In embodiments, $R^{5B}$ and $R^{5C}$ are independently substituted or unsubstituted 5 membered heteroalkyl. In embodiments, $R^{5B}$ and $R^{5C}$ are independently substituted or unsubstituted 6 membered heteroalkyl.

In embodiments, $R^{5B}$ and $R^{5C}$ are independently substituted or unsubstituted cycloalkyl (e.g., $C_3$-$C_6$, $C_4$-$C_6$, or $C_5$-$C_6$). In embodiments, $R^{5B}$ and $R^{5C}$ are independently substituted or unsubstituted $C_3$-$C_6$ cycloalkyl. In embodiments, $R^{5B}$ and $R^{5C}$ are independently substituted or unsubstituted $C_4$-$C_6$ cycloalkyl. In embodiments, $R^{5B}$ and $R^{5C}$ are independently substituted or unsubstituted $C_5$-$C_6$ cycloalkyl. In embodiments, $R^{5B}$ and $R^{5C}$ are independently substituted cyclopropyl. In embodiments, $R^{5B}$ and $R^{5C}$ are independently unsubstituted cyclopropyl. In embodiments, $R^{5B}$ and $R^{5C}$ are independently substituted cyclobutyl. In embodiments, $R^{5B}$ and $R^{5C}$ are independently unsubstituted cyclobutyl. In embodiments, $R^{5B}$ and $R^{5C}$ are independently substituted cyclopentyl. In embodiments, $R^{5B}$ and $R^{5C}$ are independently unsubstituted cyclopentyl. In embodiments, $R^5$ is substituted cyclohexyl. In embodiments, $R^{5B}$ and $R^{5C}$ are independently unsubstituted cyclohexyl.

In embodiments, $R^{5B}$ and $R^{5C}$ are independently substituted or unsubstituted heterocycloalkyl (e.g., 3 to 6 membered, 4 to 6 membered, 4 to 5 membered, or 5 to 6 membered). In embodiments, $R^{5B}$ and $R^{5C}$ are independently substituted or unsubstituted 3 to 6 membered heterocycloalkyl. In embodiments, $R^{5B}$ and $R^{5C}$ are independently substituted or unsubstituted 4 to 6 membered heterocycloalkyl. In embodiments, $R^{5B}$ and $R^{5C}$ are independently substituted or unsubstituted 5 to 6 membered heterocycloalkyl. In embodiments, $R^{5B}$ and $R^{5C}$ are independently substituted 3 membered heterocycloalkyl. In embodiments, $R^{5B}$ and $R^{5C}$ are independently unsubstituted 3 membered heterocycloalkyl. In embodiments, $R^{5B}$ and $R^{5C}$ are independently substituted 4 membered heterocycloalkyl. In embodiments, $R^{5B}$ and $R^{5C}$ are independently unsubstituted 4 membered heterocycloalkyl. In embodiments, $R^{5B}$ and $R^{5C}$ are independently substituted 5 membered heterocycloalkyl. In embodiments, $R^{5B}$ and $R^{5C}$ are independently unsubstituted 5 membered heterocycloalkyl. In embodiments, $R^{5B}$ and $R^{5C}$ are independently substituted 6 membered heterocycloalkyl. In embodiments, $R^{5B}$ and $R^{5C}$ are independently unsubstituted 6 membered heterocycloalkyl.

In embodiments, $R^{5B}$ and $R^{5C}$ are independently substituted or unsubstituted aryl (e.g., $C_6$-$C_{12}$, or phenyl). In embodiments, $R^{5B}$ and $R^{5C}$ are independently substituted phenyl. In embodiments, $R^5$ is unsubstituted phenyl. In embodiments, $R^{5B}$ and $R^{5C}$ are independently substituted or unsubstituted heteroaryl (e.g., 5 to 10 membered, 5 to 9 membered, or 5 to 6 membered). In embodiments, $R^{5B}$ and $R^{5C}$ are independently substituted or unsubstituted 5 to 10 membered heteroaryl. In embodiments, $R^{5B}$ and $R^{5C}$ are independently substituted or unsubstituted 5 to 9 membered heteroaryl. In embodiments, $R^{5B}$ and $R^{5C}$ are independently substituted or unsubstituted 5 to 6 membered heteroaryl. In embodiments, $R^{5B}$ and $R^{5C}$ are independently substituted 5 membered heteroaryl. In embodiments, $R^{5B}$ and $R^{5C}$ are independently unsubstituted 5 membered heteroaryl. In embodiments, $R^{5B}$ and $R^{5C}$ are independently substituted 6 membered heteroaryl. In embodiments, $R^{5B}$ and $R^{5C}$ are independently unsubstituted 6 membered heteroaryl. In embodiments, $R^{5B}$ and $R^{5C}$ are independently substituted 7 membered heteroaryl. In embodiments, $R^{5B}$ and $R^{5C}$ are independently unsubstituted 7 membered heteroaryl. In embodiments, $R^{5B}$ and $R^{5C}$ are independently substituted 8 membered heteroaryl. In embodiments, $R^{5B}$ and $R^{5C}$ are independently unsubstituted 8 membered heteroaryl. In embodiments, $R^{5B}$ and $R^{5C}$ are independently substituted 9 membered heteroaryl. In embodiments, $R^{5B}$ and $R^{5C}$ are independently unsubstituted 9 membered heteroaryl. In embodiments, $R^{5B}$ and $R^{5C}$ are independently substituted 10 membered heteroaryl. In embodiments, $R^{5B}$ and $R^{5C}$ are independently unsubstituted 10 membered heteroaryl.

In embodiment, $R^{5B}$ and $R^{5C}$ are joined together to form a substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 5 to 7 membered, 4 to 5 membered, or 5 to 6 membered). In embodiment, $R^{5B}$ and $R^{5C}$ are joined together to form a substituted (e.g., substituted with a substituent group, a size-limited substituent group, or a lower substituent group) or unsubstituted 3 to 8 membered heterocycloalkyl. In embodiment, $R^{5B}$ and $R^{5C}$ are joined together to form a substituted (e.g., substituted with a substituent group, a size-limited substituent group, or a lower substituent group) or unsubstituted 3 to 6 membered heterocycloalkyl. In embodiment, $R^{5B}$ and $R^{5C}$ are joined together to form a substituted (e.g., substituted with a substituent group, a size-limited substituent group, or a lower substituent group) or unsubstituted 4 to 6 membered heterocycloalkyl. In embodiment, $R^{5B}$ and $R^{5C}$ are joined together to form a substituted (e.g., substituted with a substituent group, a size-limited substituent group, or a lower substituent group) or unsubstituted 5 to 6 membered heterocycloalkyl. In embodiment, $R^{5B}$ and $R^{5C}$ are joined together to form a substituted (e.g., substituted with a substituent group, a size-limited substituent group, or a lower substituent group) or unsubstituted 5 membered heterocycloalkyl. In embodiment, $R^{5B}$ and $R^{5C}$ are joined together to form a substituted (e.g., substituted with a substituent group, a size-limited substituent group, or a lower substituent group) or unsubstituted 6 membered heterocycloalkyl. In embodiments, $R^{5B}$ and $R^{5C}$ are joined together to form substituted (e.g., substituted with a substituent group, a size-limited substituent group, or a lower substituent group) or unsubstituted pyridyl. In embodiments, $R^{5B}$ and $R^{5C}$ are joined together to form a substituted (e.g., substituted with a substituent group, a size-limited substituent group, or a lower substituent group) or unsubstituted pyrrolidinyl. In embodiments, $R^{5B}$ and $R^{5C}$ are joined together to form a substituted (e.g., substituted with a substituent group, a size-limited substituent group, or a lower substituent group) or unsubstituted piperazinyl. In embodiments, $R^{5B}$ and $R^{5C}$ are joined together to form substituted (e.g., substituted with a substituent group, a size-limited substituent group, or a lower substituent group) or unsubstituted piperidinyl. In embodiments, $R^{5B}$ and $R^{5C}$ are joined together to form substituted (e.g., substituted with a substituent group, a size-limited substituent group, or a lower substituent group) or unsubstituted morpholinyl.

In embodiment, $R^{5B}$ and $R^{5C}$ are joined together to form a substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiment, $R^{5B}$ and $R^{5C}$ are joined together to form a substituted (e.g., substituted with a substituent group, a size-limited substituent group, or a lower substituent group) or unsubstituted 5 to 10 membered heteroaryl. In embodiment, $R^{5B}$ and $R^{5C}$ are joined together to form a substituted (e.g., substituted with a substituent group, a size-limited substituent group, or a lower substituent group) or unsubstituted 5 to 9 membered heteroaryl. In embodiment, $R^{5B}$ and $R^{5C}$ are joined together to form a substituted (e.g., substituted with a substituent group, a size-limited substituent group, or a lower substituent group) or unsubstituted 5 to 6 membered heteroaryl. In embodiment, $R^{5B}$ and $R^{5C}$ are joined together to form a substituted (e.g., substituted with a substituent group, a size-limited substituent group, or a lower substituent group) or unsubstituted 5 membered heteroaryl. In embodiment, $R^{5B}$ and $R^{5C}$ are joined together to form a substituted (e.g., substituted with a substituent group, a size-limited substituent group, or a lower substituent group) or unsubstituted 6 membered heteroaryl. In embodiments, $R^{5B}$ and $R^{5C}$ are joined together to form substituted (e.g., substituted with a substituent group, a size-limited substituent group, or a lower substituent group) or unsubstituted pyrrolyl. In embodiments, $R^{5B}$ and $R^{5C}$ are joined together to form substituted (e.g., substituted with a substituent group, a size-limited substituent group, or a lower substituent group) or unsubstituted pyrimidinyl.

In embodiments, the compound has structural Formula (II):

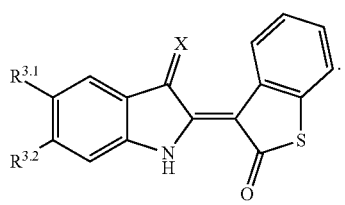

(II)

X, $R^{3.1}$, and $R^{3.2}$ areas described herein.

In embodiments, the compound has structural formula

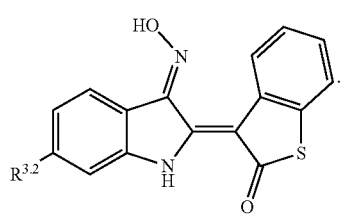

(III-A)

$R^{3.2}$ is as described herein.

In embodiments, the compound has structural formula

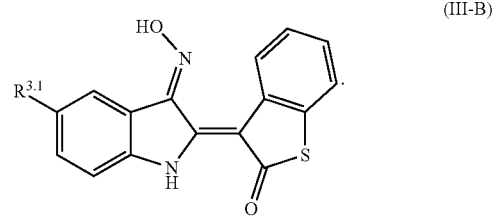

(III-B)

$R^{3.1}$ is as described herein.

In embodiments, $R^{3.1}$ and $R^{3.2}$ are independently —F, —Cl, —Br, or —I. In embodiments, $R^{3.1}$ is —F. In embodiments, $R^{3.1}$ is —Cl. In embodiments, $R^{3.1}$ is —Br. In embodiments, $R^{3.1}$ is —I. In embodiments, $R^{3.2}$ is —F. In embodiments, $R^{3.2}$ is —Cl. In embodiments, $R^{3.2}$ is —Br. In embodiments, $R^{3.2}$ is —I.

In embodiments, the compound has structural formula

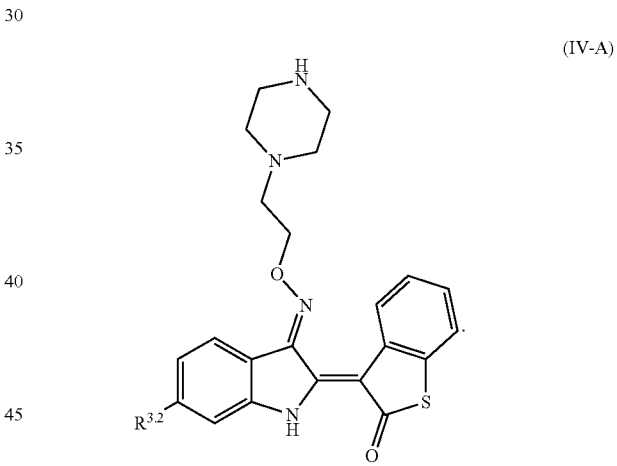

(IV-A)

$R^{3.2}$ is as described herein.

In embodiments, $R^{3.2}$ is —C(O)$R^{3.2D}$. In embodiments, $R^{3.2}$ is —C(O)O$R^{3.2D}$. In embodiments, $R^{3.2D}$ is hydrogen, or substituted or unsubstituted $C_1$-$C_4$ alkyl. In embodiments, $R^{3.2D}$ is hydrogen. In embodiments, $R^{3.2D}$ is substituted $C_1$-$C_4$ alkyl. In embodiments, $R^{3.2D}$ is unsubstituted $C_1$-$C_4$ alkyl. In embodiments, $R^{3.2D}$ is substituted $C_1$-$C_2$ alkyl. In embodiments, $R^{3.2D}$ is unsubstituted $C_1$-$C_2$ alkyl. In embodiments, $R^{3.2D}$ is unsubstituted ethyl. In embodiments, $R^{3.2D}$ is unsubstituted methyl. In embodiments, $R^{3.2}$ is —C(O)H. In embodiments, $R^{3.2}$ is —C(O)CH$_3$. In embodiments, $R^{3.2}$ is —C(O)OH. In embodiments, $R^{3.2D}$ is —C(O)OCH$_3$.

In embodiments, the compound has structural formula

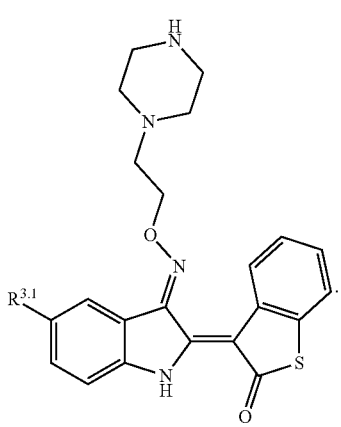

(IV-B)

R^{3.1} is as described herein.

In embodiments, R^{3.1} is —C(O)R^{3.1D}. In embodiments, R^{3.1} is —C(O)OR^{3.1D}. In embodiments, R^{3.1D} is hydrogen, or substituted or unsubstituted $C_1$-$C_4$ alkyl. In embodiments, R^{3.1D} is hydrogen. In embodiments, R^{3.1D} is substituted $C_1$-$C_4$alkyl. In embodiments, R^{3.1D} is unsubstituted $C_1$-$C_4$ alkyl. In embodiments, R^{3.1D} is substituted $C_1$-$C_2$ alkyl. In embodiments, R^{3.1D} is unsubstituted $C_1$-$C_2$ alkyl. In embodiments, R^{3.1D} is unsubstituted ethyl. In embodiments, R^{3.1D} is unsubstituted methyl. In embodiments, R^{3.1} is —C(O)H. In embodiments, R^{3.1} is —C(O)CH_3. In embodiments, R^{3.1} is —C(O)OH. In embodiments, R^{3.1} is —C(O)OCH_3.

In embodiments, $R^1$ is hydrogen, halogen (e.g., —F, —Cl, —Br, —I), oxo, —CX$^1_3$ (e.g., —CF_3, —CCl_3, —CBr_3 or —C_3), —CHX$^1_2$ (e.g., —CHF_2, —CHCl_2, —CHBr_2 or —CHI_2), —CH_2X$^1$ (e.g., —CH_2F, —CH_2Cl, —CH_2Br or —CH_2I), —N_3, —CN, —SO_{n1}R^{1A} (e.g., —SH, —SCH_3, —SOH, —SOCH_3, —SO_2H, or —SO_2CH_3), —SO_{v1}NR^{1B}R^{1C} (e.g., —SO_2NH_2 or —SO_2NHCH_3), —NR^{1B}R^{1C} (e.g., —NH_2 or —NHCH_3), —C(O)R^{1D} (e.g., —C(O)H or —C(O)CH_3), —C(O)OR^{1D} (e.g., —C(O)OH or —C(O)OCH_3), —C(O)NR^{1B}R^{1C} (e.g., —C(O)NH_2 or —C(O)NHCH_3), —OR^{1A} (e.g., —OH or —OCH_3), —OCX^{13} (e.g., —OCF_3, —OCCl_3, —OCBr_3 or —OCI_3), —OCHX$^1_2$ (e.g., —OCHF_2, —OCHCl_2, —OCHBr_2 or —OCHI_2), —OCH_2X$^1$ (e.g. —OCH_2F, —OCH_2Cl, —OCH_2Br, or —OCH_2I), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n1 is an integer from 0 to 4 (e.g. 0). v1 are independently an integer from 1 to 2. $X^1$ is independently —F, —Cl, —Br, or —I.

In embodiments $R^1$ is hydrogen, —F, —Cl, Br, —I, oxo, —CF_3, —CCl_3, —CBr_3, —CI_3, —CHF_2, —CHCl_2, —CHBr_2, —CHI_2, —CH_2F, —CH_2C, —CH_2Br, —CH_2I, —N_3, —CN, —SH, —SCH_3, —SOH, —SOCH_3, —SO_2H, —SO_2CH_3, —SO_2NH_2, —SO_2NHCH_3, —NH_2, —NHCH_3, —C(O)H, —C(O)CH_3, —C(O)OH, —C(O)OCH_3, —C(O)NH_2, —C(O)NHCH_3, —OH, —OCH_3, —OCF_3, —OCCl_3, —OCBr_3, —OCI_3, —OCHF_2, —OCHCl_2, —OCHBr_2, —OCHI_2, —OCH_2F, —OCH_2Cl, —OCH_2Br, —OCH_2I, R^{1E} substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), R^{1E}-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), R^{1E}-substituted or unsubstituted cycloalkyl (e.g., $C_3$-$C_{10}$, $C_3$-$C_8$, $C_3$-$C_6$, $C_4$-$C_6$, or $C_5$-$C_6$), R^{1E}-substituted or unsubstituted heterocycloalkyl (e.g., 3 to 10 membered, 3 to 8 membered, 3 to 6 membered, 4 to 6 membered, 4 to 5 membered, or 5 to 6 membered), R^{1E}-substituted or unsubstituted aryl (e.g., $C_6$-$C_{12}$, $C_6$-$C_{10}$, or phenyl), or R^{1E}-substituted or unsubstituted heteroaryl (e.g., 5 to 12 membered, 5 to 10 membered, 5 to 9 membered, or 5 to 6 membered). In embodiments, $R^1$ is hydrogen, —F, —Cl, Br, —I, —CF_3, —CHF_2, —CH_2F, —CCl_3, —CHCl_2, —CH_2Cl, —CBr_3, —CHBr_2, —CH_2Br, —CI_3, —CHI_2, —CH_2I, —OCF_3, —OCCl_3, —OCBr_3, —OCI_3, —OCHF_2, —OCHCl_2, —OCHBr_2, —OCHI_2, —OCH_2F, —OCH_2Cl, —OCH_2Br, —OCH_2I, —N_3, —CN, —SH, —SCH_3, —NHC(O)NH_2, —NHC(O)NHCH_3, —NO_2, —NH_2, —NHCH_3, —C(O)H, —C(O)CH_3, —C(O)OH, —C(O)OCH_3, —C(O)NH_2, —C(O)NHCH_3, —OH, —OCH_3, —NHSO_2H, —NHSO_2CH_3, —NHC(O)H, —NCH_3C(O)H, —NHC(O)OH, —NCH_3C(O)OH, —NHOH, —NCH_3OH, —NCH_3OCH_3, R^{1E}-substituted alkyl (e.g., $C_1$-$C_{20}$, $C_1$-$C_2$, $C_1$-$C_8$, $C_1$-$C_6$, $C_1$-$C_4$, or $C_1$-$C_2$), R^{1E}-substituted heteroalkyl (e.g., 2 to 20 membered, 2 to 12 membered, 2 to 8 membered, 2 to 6 membered, 4 to 6 membered, 2 to 3 membered, or 4 to 5 membered), R^{1E}-substituted cycloalkyl (e.g., $C_3$—CIO, $C_3$-$C_8$, $C_3$-$C_6$, $C_4$-$C_6$, or $C_5$-$C_6$), R^{1E}-substituted heterocycloalkyl (e.g., 3 to 10 membered, 3 to 8 membered, 3 to 6 membered, 4 to 6 membered, 4 to 5 membered, or 5 to 6 membered), R^{1E} substituted aryl(e.g., $C_6$-$C_{12}$, $C_6$-$C_{10}$, or phenyl), or R^{1E}-substituted heteroaryl (e.g., 5 to 12 membered, 5 to 10 membered, 5 to 9 membered, or 5 to 6 membered). In embodiments, $R^1$ is hydrogen, —F, —Cl, Br, —I, —CF_3, —CHF_2, —CH_2F, —CCl_3, —CHCl_2, —CH_2Cl, —CBr_3, —CHBr_2, —CH_2Br, —CI_3, —CHI_2, —CH_2I, —OCF_3, —OCCl_3, —OCBr_3, —OCI_3, —OCHF_2, —OCHCl_2, —OCHBr_2, —OCHI_2, —OCH_2F, —OCH_2Cl, —OCH_2Br, —OCH_2I, —N_3, —CN, —SH, —SCH_3, —SO_2H, —SO_2CH_3, —SO_2NH_2, —SO_2NHCH_3, —NHC(O)NH_2, —NHC(O)NHCH_3, —NO_2, —NH_2, —NHCH_3, —C(O)H, —C(O)CH_3, —C(O)OH, —C(O)OCH_3, —C(O)NH_2, —C(O)NHCH_3, —OH, —OCH_3, —NHSO_2H, —NHSO_2CH_3, —NHC(O)H, —NCH_3C(O)H, —NHC(O)OH, —NCH_3C(O)OH, —NHOH, —NCH_3OH, —NCH_3OCH_3, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{1A}$ is $R^{1E}$ substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{1E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{1E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{1E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{1E}$ substituted or unsubstituted aryl(e.g., $C_6$-$C_{12}$, $C_6$-$C_{10}$, or phenyl), or $R^{1E}$-substituted or unsubstituted heteroaryl (e.g., 5 to 12 membered, 5 to 10 membered, 5 to 9 membered, or 5 to 6 membered). In embodiments, $R^{1A}$ is $R^{1E}$ substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{1E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{1E}$-substituted cycloalkyl (e.g., $C_3$-$C_{10}$, $C_3$-$C_8$, $C_3$-$C_6$, $C_4$-$C_6$, or $C_5$-$C_6$), $R^{1E}$-substituted heterocycloalkyl (e.g., 3 to 10 membered, 3 to 8 membered, 3 to 6 membered, 4 to 6 membered, 4 to 5 membered, or 5 to 6 membered), $R^{1E}$ substituted aryl (e.g., $C_6$-$C_{12}$, $C_6$-$C_{10}$, or phenyl), or $R^{1E}$-substituted heteroaryl (e.g., 5 to 12 membered, 5 to 10 membered, 5 to 9 membered, or 5 to 6 membered). In embodiments, $R^{1A}$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^1$ is $R^{1E}$ substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is $R^{1E}$ substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $R^1$ is $R^{1E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered). In embodiments, $R^1$ is $R^{1E}$-substituted heteroalkyl (e.g., 2 to 20 membered, 2 to 12 membered, 2 to 8 membered, 2 to 6 membered, 4 to 6 membered, 2 to 3 membered, or 4 to 5 membered). In embodiments, R is unsubstituted heteroalkyl (e.g., 2 to 20 membered, 2 to 12 membered, 2 to 8 membered, 2 to 6 membered, 4 to 6 membered, 2 to 3 membered, or 4 to 5 membered).

In embodiments, $R^1$ is $R^{1E}$-substituted or unsubstituted cycloalkyl (e.g., $C_3$-$C_{10}$, $C_3$-$C_8$, $C_3$-$C_6$, $C_4$-$C_6$, or $C_5$-$C_6$). In embodiments, $R^1$ is $R^{1E}$-substituted cycloalkyl (e.g., $C_3$-$C_{10}$, $C_3$-$C_8$, $C_3$-$C_6$, $C_4$-$C_6$, or $C_5$-$C_6$). In embodiments, $R^1$ is unsubstituted cycloalkyl (e.g., $C_3$-$C_{10}$, $C_3$-$C_8$, $C_3$-$C_6$, $C_4$-$C_6$, or $C_5$-$C_6$).

In embodiments, $R^1$ is $R^{1E}$-substituted or unsubstituted heterocycloalkyl (e.g., 3 to 10 membered, 3 to 8 membered, 3 to 6 membered, 4 to 6 membered, 4 to 5 membered, or 5 to 6 membered). In embodiments, $R^1$ is $R^{1E}$-substituted heterocycloalkyl (e.g., 3 to 10 membered, 3 to 8 membered, 3 to 6 membered, 4 to 6 membered, 4 to 5 membered, or 5 to 6 membered). In embodiments, $R^1$ is unsubstituted heterocycloalkyl (e.g., 3 to 10 membered, 3 to 8 membered, 3 to 6 membered, 4 to 6 membered, 4 to 5 membered, or 5 to 6 membered).

In embodiments, $R^1$ is $R^{1E}$ substituted or unsubstituted aryl(e.g., $C_6$-$C_{12}$, $C_6$-$C_{10}$, or phenyl). In embodiments, $R^1$ is $R^{1E}$ substituted aryl(e.g., $C_6$-$C_{12}$, $C_6$-$C_{10}$, or phenyl). In embodiments, $R^1$ is unsubstituted aryl (e.g., $C_6$-$C_{12}$, $C_6$-$C_{10}$, or phenyl).

In embodiments, $R^1$ is $R^{1E}$-substituted or unsubstituted heteroaryl (e.g., 5 to 12 membered, 5 to 10 membered, 5 to 9 membered, or 5 to 6 membered). In embodiments, $R^1$ is $R^{1E}$-substituted heteroaryl (e.g., 5 to 12 membered, 5 to 10 membered, 5 to 9 membered, or 5 to 6 membered). In embodiments, $R^1$ is r unsubstituted heteroaryl (e.g., 5 to 12 membered, 5 to 10 membered, 5 to 9 membered, or 5 to 6 membered).

$R^{1E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{1F}$-substituted or unsubstituted alkyl (e.g., $C_1$-$C_8$, $C_1$-$C_6$, or $C_1$-$C_4$ alkyl), $R^{1F}$-substituted or unsubstituted heteroalkyl (e.g., 2 to 8 membered, 2 to 6 membered, or 2 to 4 membered heteroalkyl), $R^{1F}$-substituted or unsubstituted cycloalkyl (e.g., $C_3$-$C_8$, $C_3$-$C_6$, or $C_5$-$C_6$ cycloalkyl), $R^{1F}$ substituted or unsubstituted heterocycloalkyl (e.g., 3 to 8 membered, 3 to 6 membered, or 5 to 6 membered heterocycloalkyl), $R^{1F}$-substituted or unsubstituted aryl (e.g., $C_6$-$C_{10}$, $C_{10}$ aryl, or phenyl), or $R^{1F}$-substituted or unsubstituted heteroaryl (e.g., 5 to 10 membered, 5 to 9 membered, or 5 to 6 membered heteroaryl). In embodiments, $R^{1E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{1F}$ substituted alkyl(e.g., $C_1$-$C_8$, $C_1$-$C_6$, or $C_1$-$C_4$ alkyl), $R^{1F}$-substituted heteroalkyl (e.g., 2 to 8 membered, 2 to 6 membered, or 2 to 4 membered heteroalkyl), $R^{1F}$-substituted cycloalkyl (e.g., $C_3$-$C_8$, $C_3$-$C_6$, or $C_5$-$C_6$ cycloalkyl), $R^{1F}$-substituted heterocycloalkyl (e.g., 3 to 8 membered, 3 to 6 membered, or 5 to 6 membered heterocycloalkyl), $R^{1F}$ substituted aryl(e.g., $C_6$-$C_{10}$, $C_{10}$ aryl, or phenyl), or $R^{1F}$-substituted heteroaryl (e.g., 5 to 10 membered, 5 to 9 membered, or 5 to 6 membered heteroaryl). In embodiments, $R^{1E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

$R^F$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, CIO aryl or phenyl), or unsubstituted heteroaryl (e.g., 5 to 10 membered, 5 to 9 membered, or 5 to 6 membered heteroaryl).

In embodiments, $R^{1B}$ and $R^{1C}$ together with atoms attached thereto are joined to form substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1B}$ and $R^{1C}$ together with atoms attached thereto are joined to form $R^{1E}$-substituted or unsubstituted heterocycloalkyl (e.g., 3 to 10 membered, 3 to 8 membered, 3 to 6 membered, 4 to 6 membered, 4 to 5 membered, or 5 to 6 membered), or $R^{1E}$-substituted or unsubstituted heteroaryl (e.g., 5 to 12 membered, 5 to 10 membered, 5 to 9 membered, or 5 to 6 membered). In embodiments, $R^{1B}$ and $R^{1C}$ together with atoms attached thereto are joined to form $R^{1E}$-substituted heterocycloalkyl (e.g., 3 to 10 membered, 3 to 8 membered, 3 to 6 membered, 4 to 6 membered, 4 to 5 membered, or 5 to 6 membered), or $R^{1E}$ substituted heteroaryl (e.g., 5 to 12 membered, 5 to 10 membered, 5 to 9 membered, or 5 to 6 membered). In embodiments, $R^{1B}$ and $R^{1C}$ together with atoms attached thereto are joined to form unsubstituted heterocycloalkyl (e.g., 3 to 10 membered, 3 to 8 membered, 3 to 6 membered, 4 to 6 membered, 4 to 5 membered, or 5 to 6 membered), or unsubstituted heteroaryl (e.g., 5 to 12 membered, 5 to 10 membered, 5 to 9 membered, or 5 to 6 membered).

$R^2$ is hydrogen, halogen (e.g., —F, —Cl, —Br, —I), —$CX^2_3$ (e.g., —$CF_3$, —$CCl_3$, —$CBr_3$ or —$CI_3$), —$CHX^2_2$ (e.g., —$CHF_2$, —$CHCl_2$, —$CHBr_2$ or —$CHI_2$), —$CH_2X^2$ (e.g., —$CH_2F$, —$CH_2Cl$, —$CH_2Br$ or —$CH_2I$), —$N_3$, —CN, —$SO_{n2}R^{2A}$ (e.g., —SH, —$SCH_3$, —SOH, —$SOCH_3$, —$SO_2H$, or —$SO_2CH_3$), —$SO_{v2}NR^{2B}R^{2C}$ (e.g., —$SO_2NH_2$ or —$SO_2NHCH_3$), —$NHNR^{2B}R^{2C}$ (e.g., —$NHNH_2$ or —$NHNHCH_3$), —$ONR^{2B}R^{2C}$ (e.g., —$ONH_2$ or —$ONHCH_3$), —NHC(O)$NHNR^{2B}R^{2C}$ (e.g., —NHC(O)$NHNH_2$ or —NHC(O)$NHNHCH_3$), —NHC(O)$NR^{2B}R^{2C}$ (e.g., —NHC(O)$NH_2$ or —NHC(O)$NHCH_3$), —N(O)$_{m2}$ (e.g., —$NO_2$), —$NR^{2B}R^{2C}$ (e.g., —$NH_2$ or —$NHCH_3$), —C(O)$R^{2D}$ (e.g., —C(O)H or —C(O)$CH_3$), —C(O)$OR^{2D}$ (e.g., —C(O)OH or —C(O)$OCH_3$), —C(O)$NR^{2B}R^{2C}$ (e.g., —C(O)$NH_2$ or —C(O)$NHCH_3$), —$OR^{2A}$ (e.g., —OH or —$OCH_3$), —$NR^{2B}SO_2R^{2A}$ (e.g., —$NHSO_2H$, —$NCH_3SO_2H$ or —$NHSO_2CH_3$), —$NR^{2B}C(O)R^{2D}$ (e.g., —NHC(O)H, —$NCH_3C(O)H$ or —NHC(O)$CH_3$), —$NR^{2B}C(O)OR^{2D}$ (e.g., —NHC(O)OH, —$NCH_3C(O)OH$ or —NHC(O)$OCH_3$), —$NR^{2B}OR^{2D}$ (e.g., —NHOH, —$NCH_3OH$ or —$NHOCH_3$), —$OCX^2_3$ (e.g., —$OCF_3$, —$OCCl_3$, —$OCBr_3$ or —$OCI_3$), —$OCHX^2_2$ (e.g., —$OCHF_2$, —$OCHCl_2$, —$OCHBr_2$ or —$OCHI_2$), —$OCH_2X^2$ (e.g. —$OCH_2F$, —$OCH_2Cl$, —$OCH_2Br$, or —$OCH_2I$), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, $R^2$ is halogen (e.g., —F, —Cl, —Br, —I), —$CX^2_3$ (e.g., —$CF_3$, —$CCl_3$, —$CBr_3$ or —$C_3$), —$CHX^2_2$ (e.g., —$CHF_2$, —$CHCl_2$, —$CHBr_2$ or —$CHI_2$), —$CH_2X^2$ (e.g., —$CH_2F$, —$CH_2Cl$, —$CH_2Br$ or —$CH_2I$), —$N_3$, —CN, —$SO_{n2}R^{2A}$ (e.g., —SH, —$SCH_3$, —SOH, —$SOCH_3$, —$SO_2H$, or —$SO_2CH_3$), —$SO_{v2}NR^{2B}R^{2C}$ (e.g., —$SO_2NH_2$ or —$SO_2NHCH_3$), —$NHNR^{2B}R^{2C}$, (e.g., —$NH_4NH_2$ or —$NHNHCH_3$), —$ONR^{2B}R^{2C}$, (e.g., —$ONH_2$ or —$ONHCH_3$), —NHC(O)$NHNR^{2B}R^{2C}$ (e.g., —NHC(O)$NH_4NH_2$ or —NHC(O)$NHNHCH_3$), —NHC(O)$NR^{2B}R^{2C}$, (e.g., —NHC(O)$NH_2$ or —NHC(O)$NHCH_3$), —N(O)$_{m2}$ (e.g., —$NO_2$), —$NR^{2B}R^{2C}$ (e.g., —$NH_2$ or —$NHCH_3$), —C(O)$R^{2D}$ (e.g., —C(O)H or —C(O)$CH_3$), —C(O)$OR^{2D}$ (e.g., —C(O)OH or —C(O)$OCH_3$), —C(O)$NR^{2B}R^{2C}$ (e.g., —C(O)$NH_2$ or —C(O)$NHCH_3$), —$OR^{2A}$ (e.g., —OH or —$OCH_3$), —$NR^{2B}SO_2R^{2A}$ (e.g., —$NHSO_2H$, —$NCH_3SO_2H$ or —$NHSO_2CH_3$), —$NR^{2B}C(O)R^{2D}$ (e.g., —NHC(O)H, —$NCH_3C(O)H$ or —NHC(O)$CH_3$), —$NR^{2B}C(O)OR^{2D}$ (e.g., —NHC(O)OH, —$NCH_3C(O)OH$ or —NHC(O)$OCH_3$), —$NR^{2B}OR^{2D}$ (e.g., —NHOH, —$NCH_3OH$ or —$NHOCH_3$), —$OCX^2_3$ (e.g., —$OCF_3$, —$OCCl_3$, —$OCBr_3$ or —$OCI_3$), —$OCHX^2_2$ (e.g., —$OCHF_2$, —$OCHCl_2$, —$OCHBr_2$ or —$OCHI_2$), —$OCH_2X^2$ (e.g. —$OCH_2F$, —$OCH_2Cl$, —$OCH_2Br$, or —$OCH_2I$), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n2 is an integer from 0 to 4 (e.g. 0). m2 and v2 are independently an integer from 1 to 2. $X^2$ is independently —F, —Cl, —Br, or —I.

In embodiments, $R^2$ is hydrogen, —F, —Cl, Br, —I, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —SH, —$SCH_3$, —SOH, —$SOCH_3$, —$SO_2H$, —$SO_2CH_3$, —$SO_2NH_2$, —$SO_2NHCH_3$, —$NHNH_2$, —$NHNHCH_3$, —$ONH_2$, —$ONHCH_3$, —$NHC(O)NHNH_2$, —$NHC(O)NHNHCH_3$, —$NHC(O)NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NCH_3SO_2H$, —$NHSO_2CH_3$, —NHC(O)H, —$NCH_3C(O)H$, —NHC(O)$CH_3$, —NHC(O)OH, —$NCH_3C(O)OH$, —NHC(O)$OCH_3$, —NHOH, —$NCH_3OH$, —$NHOCH_3$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, $R^2$ is —F, —Cl, Br, —I, —$CF_3$, —$CCl_3$, —$CBr_3$, —$C_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —SH, —$SCH_3$, —SOH, —$SOCH_3$, —$SO_2H$, —$SO_2CH_3$, —$SO_2NH_2$, —$SO_2NHCH_3$, —$NHNH_2$, —$NHNHCH_3$, —$ONH_2$, —$ONHCH_3$, —$NHC(O)NHNH_2$, —NHC(O)$NHNHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NCH_3SO_2H$, —$NHSO_2CH_3$, —NHC(O)H, —$NCH_3C(O)H$, —NHC(O)$CH_3$, —NHC(O) OH, —$NCH_3C(O)OH$, —NHC(O)$OCH_3$, —NHOH, —$NCH_3OH$, —$NHOCH_3$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

In embodiments, $R^{2B}$ and $R^{2C}$ together with atoms attached thereto are joined to form substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{2B}$ and $R^{2C}$ together with atoms attached thereto are joined to form substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, $R^{2B}$ and $R^{2C}$ together with atoms attached thereto are joined to form unsubstituted heterocycloalkyl (e.g., 3 to 10 membered, 3 to 8 membered, 3 to 6 membered, 4 to 6 membered, 4 to 5 membered, or 5 to 6 membered), or unsubstituted heteroaryl (e.g., 5 to 12 membered, 5 to 10 membered, 5 to 9 membered, or 5 to 6 membered).

$R^3$ is hydrogen, halogen (e.g., —F, —Cl, —Br, —I), —$CX^3_3$ (e.g., —$CF_3$, —$CCl_3$, —$CBr_3$ or —$CI_3$), —$CHX^3_2$ (e.g., —$CHF_2$, —$CHCl_2$, —$CHBr_2$ or —$CHI_2$), —$CH_2X^3$ (e.g., —$CH_2F$, —$CH_2Cl$, —$CH_2Br$ or —$CH_2I$), —$N_3$, —CN, —$SO_3R^{3A}$ (e.g., —SH, —$SCH_3$, —SOH, —$SOCH_3$, —$SO_2H$, or —$SO_2CH_3$), —$SO_{v3}NR^{3B}R^{3C}$ (e.g., —$SO_2NH_2$ or —$SO_2NHCH_3$), —$N1NR^{3B}R^{3C}$ (e.g., —$NHNH_2$ or —$NHNHCH_3$), —$ONR^{3B}R^{3C}$ (e.g., —$ONH_2$ or —$ONHCH_3$), —NHC(O)$NHNR^{3B}R^{3C}$ (e.g., —NHC(O)$NHNH_2$ or —NHC(O)$NHNHCH_3$), —NHC(O)$NR^{3B}R^{3C}$ (e.g., —NHC(O)$NH_2$ or —NHC(O)$NHCH_3$), —N(O)$_{m3}$ (e.g., —$NO_2$), —$NR^{3B}R^{3C}$ (e.g., —$NH_2$ or —$NHCH_3$), —C(O)$R^{3D}$ (e.g., —C(O)H or —C(O)$CH_3$), —C(O)$OR^{3D}$ (e.g., —C(O)OH or —C(O)OCH$_3$), —C(O)NR$^{3B}$R$^{3C}$ (e.g., —C(O)NH$_2$ or —C(O)NHCH$_3$), —OR$^{3A}$ (e.g., —OH or —OCH$_3$), —NR$^{3B}$SO$_2$R$^{3A}$ (e.g., —NHSO$_2$H, —NCH$_3$SO$_2$H or —NHSO$_2$CH$_3$), —NR$^{3B}$C(O)R$^{3D}$ (e.g., —NHC(O)H, —NCH$_3$C(O)H or —NHC(O)CH$_3$), —NR$^{3B}$C(O)OR$^{3D}$ (e.g., —NHC(O)OH, —NCH$_3$C(O)OH or —NHC(O)OCH$_3$), —NR$^{3B}$OR$^{3D}$ (e.g., —NHOH, —NCH$_3$OH or —NHOCH$_3$), —OCX$^3_3$ (e.g., —OCF$_3$, —OCCl$_3$, —OCBr$_3$ or —OCI$_3$), —OCHX$^3_2$ (e.g., —OCHF$_2$, —OCHCl$_2$, —OCHBr$_2$ or —OCHI$_2$), —OCH$_2$X$^3$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, R$^3$ is halogen (e.g., —F, —Cl, —Br, —I), —CX$^3_3$ (e.g., —CF$_3$, —CCl$_3$, —CBr$_3$ or —C$_3$), —CHX$^3_2$ (e.g., —CHF$_2$, —CHCl$_2$, —CHBr$_2$ or —CHI$_2$), —CH$_2$X$^3$ (e.g., —CH$_2$F, —CH$_2$C, —CH$_2$Br or —CH$_2$I), —N$_3$, —CN, —SO$_{n3}$R$^{3A}$ (e.g., —SH, —SCH$_3$, —SOH, —SOCH$_3$, —SO$_2$H, or —SO$_2$CH$_3$), —SO$_{n3}$NR$^{3B}$R$^{3C}$ (e.g., —SO$_2$NH$_2$ or —SO$_2$NHCH$_3$), —NHNR$^{3B}$R$^{3C}$ (e.g., —NH$_4$NH$_2$ or —NHNHCH$_3$), —ONR$^{3B}$R$^{3C}$ (e.g., —ONH$_2$ or —ONHCH$_3$), —NHC(O)NHNR$^{3B}$R$^{3C}$ (e.g., —NHC(O) NHNH$_2$ or —NHC(O)NHNHCH$_3$), —NHC(O)NR$^{3B}$R$^{3C}$ (e.g., —NHC(O)NH$_2$ or —NHC(O)NHCH$_3$), —N(O)$_{m3}$ (e.g., —NO$_2$), —NR$^{3B}$R$^{3C}$ (e.g., —NH$_2$ or —NHCH$_3$), —C(O)R$^{3D}$ (e.g., —C(O)H or —C(O)CH$_3$), —C(O)OR$^{3D}$ (e.g., —C(O)OH or —C(O)OCH$_3$), —C(O)NR$^{3B}$R$^{3C}$ (e.g., —C(O)NH$_2$ or —C(O)NHCH$_3$), —OR$^{3A}$ (e.g., —OH or —OCH$_3$), —NR$^{3B}$SO$_2$R$^{3A}$ (e.g., —NHSO$_2$H, —NCH$_3$SO$_2$H or —NHSO$_2$CH$_3$), —NR$^{3B}$C(O)R$^{3D}$ (e.g., —NHC(O)H, —NCH$_3$C(O)H or —NHC(O)CH$_3$), —NR$^{3B}$C(O)OR$^{3D}$ (e.g., —NHC(O)OH, —NCH$_3$C(O)OH or —NHC(O)OCH$_3$), —NR$^{3B}$OR$^{3D}$ (e.g., —NHOH, —NCH$_3$OH or —NHOCH$_3$), —OCX$^3_3$ (e.g., —OCF$_3$, —OCCl$_3$, —OCBr$_3$ or —OCI$_3$), —OCHX$^3_2$ (e.g., —OCHF$_2$, —OCHCl$_2$, —OCHBr$_2$ or —OCHI$_2$), —OCH$_2$X$^3$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n3 is an integer from 0 to 4 (e.g. 0). m3 and v3 are independently an integer from 1 to 2. X$^3$ is independently —F, —Cl, —Br, or —I.

In embodiments, R$^3$ is hydrogen, —F, —Cl, Br, —I, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —SH, —SCH$_3$, —SOH, —SOCH$_3$, —SO$_2$H, —SO$_2$CH$_3$, —SO$_2$NH$_2$, —SO$_2$NHCH$_3$, —NHNH$_2$, —NHNHCH$_3$, —ONH$_2$, —ONHCH$_3$, —NHC(O)NHNH$_2$, —NHC(O)NHNHCH$_3$, —NHC(O)NH$_2$, —NHC(O) NHCH$_3$, —NO$_2$, —NH$_2$, —NHCH$_3$, —C(O)H, —C(O) CH$_3$, —C(O)OH, —C(O)OCH$_3$, —C(O)NH$_2$, —C(O) NHCH$_3$, —OH, —OCH$_3$, —NHSO$_2$H, —NCH$_3$SO$_2$H, —NHSO$_2$CH$_3$, —NHC(O)H, —NCH$_3$C(O)H, —NHC(O) CH$_3$, —NHC(O)OH, —NCH$_3$C(O)OH, —NHC(O)OCH$_3$, —NHOH, —NCH$_3$OH, —NHOCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, R$^3$ is —F, —Cl, Br, —I, —CF$_3$, —CCl$_3$, —CBr$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —SH, —SCH$_3$, —SOH, —SOCH$_3$, —SO$_2$H, —SO$_2$CH$_3$, —SO$_2$NH$_2$, —SO$_2$NHCH$_3$, —NHNH$_2$, —NHNHCH$_3$, —ONH$_2$, —ONHCH$_3$, —NHC(O)NH—NH$_2$, —NHC(O) NHNHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NCH$_3$SO$_2$H, —NHSO$_2$CH$_3$, —NHC(O)H, —NCH$_3$C(O)H, —NHC(O)CH$_3$, —NHC(O)

OH, —NCH$_3$C(O)OH, —NHC(O)OCH$_3$, —NHOH, —NCH$_3$OH, —NHOCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

In embodiments, R$^{3B}$ and R$^{3C}$ together with atoms attached thereto are joined to form substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, R$^{3B}$ and R$^{3C}$ together with atoms attached thereto are joined to form substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, R$^{3B}$ and R$^{3C}$ together with atoms attached thereto are joined to form unsubstituted heterocycloalkyl (e.g., 3 to 10 membered, 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered).

R$^{3.1}$ is hydrogen, halogen (e.g., —F, —Cl, —Br, —I), —CX$^{3.13}$ (e.g., —CF$_3$, —CCl$_3$, —CBr$_3$ or —CI$_3$), —CHX$^{3.1}_2$ (e.g., —CHF$_2$, —CHCl$_2$, —CHBr$_2$ or —CHI$_2$), —CH$_2$X$^{3.1}$ (e.g., —CH$_2$F, —CH$_2$Cl, —CH$_2$Br or —CH$_2$I), —N$_3$, —CN, —SO$_{n3.1}$R$^{3.1A}$ (e.g., —SH, —SCH$_3$, —SOH, —SOCH$_3$, —SO$_2$H, or —SO$_2$CH$_3$), —SO$_{v3.1}$NR$^{3.1B}$R$^{3.1C}$ (e.g., —SO$_2$NH$_2$ or —SO$_2$NHCH$_3$), —NHNR$^{3.1B}$R$^{3.1C}$ (e.g., —NHNH$_2$ or —NHNHCH$_3$), —ONR$^{3.1B}$R$^{3.1C}$ (e.g., —ONH$_2$ or —ONHCH$_3$), —NHC(O)NHNR$^{3.1B}$R$^{3.1C}$ (e.g., —NHC(O)NHNH$_2$ or —NHC(O)NHNHCH$_3$), —NHC(O)NR$^{3.1B}$R$^{3.1C}$ (e.g., —NHC(O)NH$_2$ or —NHC(O)NHCH$_3$), —N(O)$_{m3.1}$ (e.g., —NO$_2$), —NR$^{3.1B}$R$^{3.1C}$ (e.g., —NH$_2$ or —NHCH$_3$), —C(O)R$^{3.1D}$ (e.g., —C(O)H or —C(O)CH$_3$), —C(O)OR$^{3.1D}$ (e.g., —C(O)OH or —C(O)OCH$_3$), —C(O)NR$^{3.1B}$R$^{3.1C}$ (e.g., —C(O)NH$_2$ or —C(O)NHCH$_3$), —OR$^{3.1A}$ (e.g., —OH or —OCH$_3$), —NR$^{3.1B}$SO$_2$R$^{3.1A}$ (e.g., —NHSO$_2$H, —NCH$_3$SO$_2$H or —NHSO$_2$CH$_3$), —NR$^{3.1B}$C(O)R$^{3.1D}$ (e.g., —NHC(O)H, —NCH$_3$C(O)H or —NHC(O)CH$_3$), —NR$^{3.1B}$C(O)OR$^{3.1D}$ (e.g., —NHC(O)OH, —NCH$_3$C(O)OH or —NHC(O)OCH$_3$), —NR$^{3.1B}$OR$^{3.1D}$ (e.g., —NHOH, —NCH$_3$OH or —NHOCH$_3$), —OCX$^{3.1}_3$ (e.g., —OCF$_3$, —OCCl$_3$, —OCBr$_3$ or —OCI$_3$), —OCHX$^{3.1}_2$ (e.g., —OCHF$_2$, —OCHCl$_2$, —OCHBr$_2$ or —OCHI$_2$), —OCH$_2$X$^{3.1}$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, R$^{3.1}$ is halogen (e.g., —F, —Cl, —Br, —I), —CX$^{3.1}_3$ (e.g., —CF$_3$, —CCl$_3$, —CBr$_3$ or —C$_3$), —CHX$^{3.1}_2$ (e.g., —CHF$_2$, —CHCl$_2$, —CHBr$_2$ or —CHI$_2$), —CH$_2$X$^{3.1}$ (e.g., —CH$_2$F, —CH$_2$Cl, —CH$_2$Br or —CH$_2$I), —N$_3$, —CN, —SO$_{n3.1}$R$^{3.1A}$ (e.g., —SH, —SCH$_3$, —SOH, —SOCH$_3$, —SO$_2$H, or —SO$_2$CH$_3$), —SO$_{v3.1}$NR$^{3.1B}$R$^{3.1C}$ (e.g., —SO$_2$NH$_2$ or —SO$_2$NHCH$_3$), —NHNR$^{3.1B}$R$^{3.1C}$ (e.g., —NHNH$_2$ or —NHNHCH$_3$), —ONR$^{3.1B}$R$^{3.1C}$ (e.g., —ONH$_2$ or —ONHCH$_3$), —NHC(O)NHNR$^{3.1B}$R$^{3.1C}$ (e.g., —NHC(O)NHNH$_2$ or —NHC(O)NHNHCH$_3$), —NHC(O)NR$^{3.1B}$R$^{3.1C}$ (e.g., —NHC(O)NH$_2$ or —NHC(O)NHCH$_3$), —N(O)$_{m3.1}$ (e.g., —NO$_2$), —NR$^{3.1B}$R$^{3.1C}$ (e.g., —NH$_2$ or —NHCH$_3$), —C(O)R$^{3.1D}$ (e.g., —C(O)H or —C(O)CH$_3$), —C(O)OR$^{3.1D}$ (e.g., —C(O)OH or —C(O)OCH$_3$), —C(O)NR$^{3.1B}$R$^{3.1C}$ (e.g., —C(O)NH$_2$ or —C(O)NHCH$_3$), —OR$^{3.1A}$ (e.g., —OH or —OCH$_3$), —NR$^{3.1B}$SO$_2$R$^{3.1A}$ (e.g., —NHSO$_2$H, —NCH$_3$SO$_2$H or —NHSO$_2$CH$_3$), —NR$^{3.1B}$C(O)R$^{3.1D}$ (e.g., —NHC(O)H, —NCH$_3$C(O)H or —NHC(O)CH$_3$), —NR$^{3.1B}$C(O)OR$^{3.1D}$ (e.g., —NHC(O)OH, —NCH$_3$C(O)OH or —NHC(O)OCH$_3$), —NR$^{3.1B}$OR$^{3.1D}$ (e.g., —NHOH, —NCH$_3$OH or —NHOCH$_3$), —OCX$^{3.1}_3$ (e.g., —OCF$_3$, —OCCl$_3$, —OCBr$_3$ or —OCI$_3$), —OCHX$^{3.1}_2$ (e.g., —OCHF$_2$, —OCHCl$_2$, —OCHBr$_2$ or —OCHI$_2$), —OCH$_2$X$^{3.1}$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n3.1 is an integer from 0 to 4 (e.g. 0). m3.1 and v3.1 are independently an integer from 1 to 2. $X^{3.1}$ is independently —F, —Cl, —Br, or —I.

In embodiments, $R^{3.1}$ is hydrogen, —F, —Cl, Br, —I, —$CF_3$, —$CCl_3$, —$CBr_3$, —$C_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —SH, —$SCH_3$, —SOH, —$SOCH_3$, —$SO_2H$, —$SO_2CH_3$, —$SO_2NH_2$, —$SO_2NHCH_3$, —$NHNH_2$, —$NHNHCH_3$, —$ONH_2$, —$ONHCH_3$, —NHC(O)NH—$NH_2$, —NHC(O)NHNHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NCH$_3$SO$_2$H, —NHSO$_2$CH$_3$, —NHC(O)H, —NCH$_3$C(O)H, —NHC(O)CH$_3$, —NHC(O)OH, —NCH$_3$C(O)OH, —NHC(O)OCH$_3$, —NHOH, —NCH$_3$OH, —NHOCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, $R^{3.1}$ is —F, —Cl, Br, —I, —CF$_3$, —CCl$_3$, —CBr$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —SH, —SCH$_3$, —SOH, —SOCH$_3$, —SO$_2$H, —SO$_2$CH$_3$, —SO$_2$NH$_2$, —SO$_2$NHCH$_3$, —NHNH$_2$, —NHNHCH$_3$, —ONH$_2$, —ONHCH$_3$, —NHC(O)NHNH$_2$, —NHC(O)NHNHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NCH$_3$SO$_2$H, —NHSO$_2$CH$_3$, —NHC(O)H, —NCH$_3$C(O)H, —NHC(O)CH$_3$, —NHC(O)OH, —NCH$_3$C(O)OH, —NHC(O)OCH$_3$, —NHOH, —NCH$_3$OH, —NHOCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

$R^{3.2}$ is hydrogen, halogen (e.g., —F, —Cl, —Br, —I), —$CX^{3.2}_3$ (e.g., —CF$_3$, —CCl$_3$, —CBr$_3$ or —CI$_3$), —$CHX^{3.2}_2$ (e.g., —CHF$_2$, —CHCl$_2$, —CHBr$_2$ or —CHI$_2$), —$CH_2X^{3.2}$ (e.g., —CH$_2$F, —CH$_2$Cl, —CH$_2$Br or —CH$_2$I), —N$_3$, —CN, —SO$_{n3.2}$R$^{3.2A}$ (e.g., —SH, —SCH$_3$, —SOH, —SOCH$_3$, —SO$_2$H, or —SO$_2$CH$_3$), —SO$_{v3.2}$NR$^{3.2B}$R$^{3.2C}$, (e.g., —SO$_2$NH$_2$ or —SO$_2$NHCH$_3$), —NHNR$^{3.2B}$R$^{3.2C}$, (e.g., —NHNH$_2$ or —NHNHCH$_3$), —ONR$^{3.2B}$R$^{3.2C}$, (e.g., —ONH$_2$ or —ONHCH$_3$), —NHC(O)NHNR$^{3.2B}$R$^{3.2C}$, (e.g., —NHC(O)NHNH$_2$ or —NHC(O)NHNHCH$_3$), —NHC(O)NR$^{3.2B}$R$^{3.2C}$, (e.g., —NHC(O)NH$_2$ or —NHC(O)NHCH$_3$), —N(O)$_{m3.2}$ (e.g., —NO$_2$), —NR$^{3.2B}$R$^{3.2C}$, (e.g., —NH$_2$ or —NHCH$_3$), —C(O)R$^{3.2D}$ (e.g., —C(O)H or —C(O)CH$_3$), —C(O)OR$^{3.2D}$ (e.g., —C(O)OH or —C(O)OCH$_3$), —C(O)NR$^{3.2B}$R$^{3.2C}$, (e.g., —C(O)NH$_2$ or —C(O)NHCH$_3$), —OR$^{3.2A}$ (e.g., —OH or —OCH$_3$), —NR$^{3.2B}$SO$_2$R$^{3.2A}$ (e.g., —NHSO$_2$H, —NCH$_3$SO$_2$H or —NHSO$_2$CH$_3$), —NR$^{3.2B}$C(O)R$^{3.2D}$ (e.g., —NHC(O)H, —NCH$_3$C(O)H or —NHC(O)CH$_3$), —NR$^{3.2B}$C(O)OR$^{3.2D}$ (e.g., —NHC(O)OH, —NCH$_3$C(O)OH or —NHC(O)OCH$_3$), —NR$^{3.2B}$OR$^{3.2D}$ (e.g., —NHOH, —NCH$_3$OH or —NHOCH$_3$), —OCX$^{3.2}_3$ (e.g., —OCF$_3$, —OCCl$_3$, —OCBr$_3$ or —OCI$_3$), —OCHX$^{3.2}_2$ (e.g., —OCHF$_2$, —OCHCl$_2$, —OCHBr$_2$ or —OCHI$_2$), —OCH$_2$X$^{3.2}$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, $R^{3.2}$ is halogen (e.g., —F, —Cl, —Br, —I), —$CX^{3.2}_3$ (e.g., —$CF_3$, —$CCl_3$, —$CBr_3$ or —$C_3$), —$CHX^{3.2}_2$ (e.g., —$CHF_2$, —$CHCl_2$, —$CHBr_2$ or —$CHI_2$), —$CH_2X^{3.2}$ (e.g., —$CH_2F$, —$CH_2Cl$, —$CH_2Br$ or —$CH_2I$), —$N_3$, —CN, —$SO_{n3.2}R^{3.2A}$ (e.g., —SH, —$SCH_3$, —SOH, —$SOCH_3$, —$SO_2H$, or —$SO_2CH_3$), —$SO_{v3.2}NR^{3.2B}R^{3.2C}$ (e.g., —$SO_2NH_2$ or —$SO_2NHCH_3$), —$NHNR^{3.2B}R^{3.2C}$ (e.g., —$NHNH_2$ or —$NHNHCH_3$), —$ONR^{3.2B}R^{3.2C}$ (e.g., —$ONH_2$ or —$ONHCH_3$), —$NHC(O)NHNR^{3.2B}R^{3.2C}$ (e.g., —$NHC(O)NHNH_2$ or —$NHC(O)NH_4NHCH_3$), —$NHC(O)NR^{3.2B}R^{3.2C}$, (e.g., —$NHC(O)NH_2$ or —$NHC(O)NHCH_3$), —$N(O)_{m3.2}$ (e.g., —$NO_2$), —$NR^{3.2B}R^{3.2C}$, (e.g., —$NH_2$ or —$NHCH_3$), —$C(O)R^{3.2D}$ (e.g., —C(O)H or —$C(O)CH_3$), —$C(O)OR^{3.2}D$ (e.g., —C(O)OH or —$C(O)OCH_3$), —$C(O)NR^{3.2B}R^{3.2C}$, (e.g., —$C(O)NH_2$ or —$C(O)NHCH_3$), —$OR^{3.2A}$ (e.g., —OH or —$OCH_3$), —$NR^{3.2B}SO_2R^{3.2A}$ (e.g., —$NHSO_2H$, —$NCH_3SO_2H$ or —$NHSO_2CH_3$), —$NR^{3.2B}C(O)R^{3.2D}$ (e.g., —NHC(O)H, —$NCH_3C(O)H$ or —$NHC(O)CH_3$), —$NR^{3.2B}C(O)OR^{3.2D}$ (e.g., —NHC(O)OH, —$NCH_3C(O)OH$ or —$NHC(O)OCH_3$), —$NR^{3.2B}OR^{3.2}D$ (e.g., —NHOH, —$NCH_3OH$ or —$NHOCH_3$), —$OCX^{3.2}_3$ (e.g., —$OCF_3$, —$OCCl_3$, —$OCBr_3$ or —$OCI_3$), —$OCHX^{3.2}_2$ (e.g., —$OCHF_2$, —$OCHCl_2$, —$OCHBr_2$ or —$OCHI_2$), —$OCH_2X^{3.2}$ (e.g. —$OCH_2F$, —$OCH_2Cl$, —$OCH_2Br$, or —$OCH_2I$), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n3.2 is an integer from 0 to 4 (e.g. 0). m3.2 and v3.2 are independently an integer from 1 to 2. $X^{3.2}$ is independently —F, —Cl, —Br, or —I.

In embodiments, $R^{3.2}$ is hydrogen, —F, —Cl, Br, —I, —$CF_3$, —$CCl_3$, —$CBr_3$, —$C_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —SH, —$SCH_3$, —SOH, —$SOCH_3$, —$SO_2H$, —$SO_2CH_3$, —$SO_2NH_2$, —$SO_2NHCH_3$, —$NHNH_2$, —$NHNHCH_3$, —$ONH_2$, —$ONHCH_3$, —$NHC(O)NHNH_2$, —$NHC(O)NHNHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NCH_3SO_2H$, —$NHSO_2CH_3$, —NHC(O)H, —$NCH_3C(O)H$, —$NHC(O)CH_3$, —NHC(O)OH, —$NCH_3C(O)OH$, —$NHC(O)OCH_3$, —NHOH, —$NCH_3OH$, —$NHOCH_3$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

In embodiments, $R^4$ is hydrogen, halogen (e.g., —F, —Cl, —Br, —I), oxo, —$CX^4_3$ (e.g., —$CF_3$, —$CCl_3$, —$CBr_3$ or —$CI_3$), —$CHX^4_2$ (e.g., —$CHF_2$, —$CHCl_2$, —$CHBr_2$ or —$CHI_2$), —$CH_2X^4$ (e.g., —$CH_2F$, —$CH_2Cl$, —$CH_2Br$ or —$CH_2I$), —CN, —$SO_{n4}R^{4A}$ (e.g., —SH, —$SCH_3$, —SOH, —$SOCH_3$, —$SO_2H$, or —$SO_2CH_3$), —$SO_{v4}NR^{4B}R^{4C}$ (e.g., —$SO_2NH_2$ or —$SO_2NHCH_3$), —$NR^{4B}R^{4C}$ (e.g., —$NH_2$ or —$NHCH_3$), —$C(O)R^{4D}$ (e.g., —C(O)H or —$C(O)CH_3$), —$C(O)OR^{4D}$ (e.g., —C(O)OH or —$C(O)OCH_3$), —$C(O)NR^{4B}R^{4C}$ (e.g., —$C(O)NH_2$ or —$C(O)NHCH_3$), —$OR^{4A}$ (e.g., —OH or —$OCH_3$), —$OCX^4_3$ (e.g., —$OCF_3$, —$OCCl_3$, —$OCBr_3$ or —$OCI_3$), —$OCHX^4_2$ (e.g., —$OCHF_2$, —$OCHCl_2$, —$OCHBr_2$ or —$OCHI_2$), —$OCH_2X^4$ (e.g. —$OCH_2F$, —$OCH_2Cl$, —$OCH_2Br$, or —$OCH_2I$), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n4 is an integer from 0 to 4 (e.g. 0). v4 is an integer from 1 to 2. $X^4$ is independently —F, —Cl, —Br, or —I.

In embodiments, $R^4$ is hydrogen, —F, —Cl, Br, —I, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2C$, —$CH_2Br$, —$CH_2I$, —CN, —SH, —$SCH_3$, —SOH, —$SOCH_3$, —$SO_2H$, —$SO_2CH_3$, —$SO_2NH_2$, —$SO_2NHCH_3$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

$R^5$ is hydrogen, halogen (e.g., —F, —Cl, —Br, —I), —$CX^5_3$ (e.g., —$CF_3$, —$CCl_3$, —$CBr_3$ or —$CI_3$), —$CHX^{52}$ (e.g., —$CHF_2$, —$CHCl_2$, —$CHBr_2$ or —$CHI_2$), —$CH_2X^5$ (e.g., —$CH_2F$, —$CH_2C$, —$CH_2Br$ or —$CH_2I$), —CN, —$N_3$, —$SO_{n5}R^{5A}$ (e.g., —SH, —$SCH_3$, —SOH, —$SOCH_3$, —$SO_2H$, or —$SO_2CH_3$), —$SO_{v5}NR^{5B}R^{5C}$ (e.g., —$SO_2NH_2$ or —$SO_2NHCH_3$), —$N1NR^{5B}R^{5C}$ (e.g., —$NHNH_2$ or —$NH_4NHCH_3$), —$ONR^{5B}R^{5C}$ (e.g., —$ONH_2$ or —$ONHCH_3$), —$NHC(O)NHNR^{5B}R^{5C}$, (e.g., —NHC(O)$NHNH_2$ or —NHC(O)$NHNHCH_3$), —$NHC(O)NR^{5B}R^{5C}$ (e.g., —$NHC(O)NH_2$ or —$NHC(O)NHCH_3$), —$N(O)_{m5}$ (e.g., —$NO_2$), —$NR^{5B}R^{5C}$ (e.g., —$NH_2$ or —$NHCH_3$), —$C(O)R^{5D}$ (e.g., —C(O)H or —$C(O)CH_3$), —$C(O)OR^{5D}$ (e.g., —C(O)OH or —$C(O)OCH_3$), —$C(O)NR^{5B}R^{5C}$, (e.g., —$C(O)NH_2$ or —$C(O)NHCH_3$), —$OR^{5A}$ (e.g., —OH or —$OCH_3$), —$NR^{5B}SO_2R^{5A}$, (e.g., —$NHSO_2H$, —$NCH_3SO_2H$ or —$NHSO_2CH_3$), —$NR^BC(O)R^{5D}$ (e.g., —NHC(O)H, —$NCH_3C(O)H$ or —$NHC(O)CH_3$), —$NR^{5B}C(O)OR^{5D}$ (e.g., —NHC(O)OH, —$NCH_3C(O)OH$ or —$NHC(O)OCH_3$), —$NR^{5B}OR^{5D}$ (e.g., —NHOH, —$NCH_3OH$ or —$NHOCH_3$), —$OCX^5_3$ (e.g., —$OCF_3$, —$OCCl_3$, —$OCBr_3$ or —$OCI_3$), —$OCHX^5_2$ (e.g., —$OCHF_2$, —$OCHCl_2$, —$OCHBr_2$ or —$OCHI_2$), —$OCH_2X^5$ (e.g. —$OCH_2F$, —$OCH_2C$, —$OCH_2Br$, or —$OCH_2I$), substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, $R^5$ is halogen (e.g., —F, —Cl, —Br, —I), —$CX^5_3$ (e.g., —$CF_3$, —$CCl_3$, —$CBr_3$ or —$C_3$), —$CHX^{52}$ (e.g., —$CHF_2$, —$CHCl_2$, —$CHBr_2$ or —$CHI_2$), —$CH_2X^5$ (e.g., —$CH_2F$, —$CH_2Cl$, —$CH_2Br$ or —$CH_2I$), —CN, —$N_3$, —$SO_{n5}R^{5A}$ (e.g., —SH, —$SCH_3$, —SOH, —$SOCH_3$, —$SO_2H$, or —$SO_2CH_3$), —$SO_{v5}NR^{5B}R^{5C}$ (e.g., —$SO_2NH_2$ or —$SO_2NHCH_3$), —$NHNR^{5B}R^{5C}$, (e.g., —$NHNH_2$ or —$NHNHCH_3$), —$ONR^{5B}R^{5C}$ (e.g., —$ONH_2$ or —$ONHCH_3$), —$NHC(O)NHNR^{5B}R^{5C}$ (e.g., —NHC(O)$NHNH_2$ or —NHC(O)$NHNHCH_3$), —$NHC(O)NR^{5B}R^{5C}$, (e.g., —$NHC(O)NH_2$ or —$NHC(O)NHCH_3$), —$N(O)_{m5}$ (e.g., —$NO_2$), —$NR^{5B}R^{5C}$ (e.g., —$NH_2$ or —$NHCH_3$), —$C(O)R^{5D}$ (e.g., —C(O)H or —$C(O)CH_3$), —$C(O)OR^{5D}$ (e.g., —C(O)OH or —$C(O)OCH_3$), —$C(O)NR^{5B}R^{5C}$, (e.g., —C(O)NH$_2$ or —C(O)NHCH$_3$), —OR$^{5A}$ (e.g., —OH or —OCH$_3$), —NR$^{5B}$SO$_2$R$^{5A}$ (e.g., —NHSO$_2$H, —NCH$_3$SO$_2$H or —NHSO$_2$CH$_3$), —NR$^{5B}$C(O)R$^{5D}$ (e.g., —NHC(O)H, —NCH$_3$C(O)H or —NHC(O)CH$_3$), —NR$^{5B}$C(O)OR$^D$ (e.g., —NHC(O)OH, —NCH$_3$C(O)OH or —NHC(O)OCH$_3$), —NR$^{5B}$OR$^{5D}$ (e.g., —NHOH, —NCH$_3$OH or —NHOCH$_3$), —OCX$^5_3$ (e.g., —OCF$_3$, —OCCl$_3$, —OCBr$_3$ or —OCI$_3$), —OCHX$^5_2$ (e.g., —OCHF$_2$, —OCHCl$_2$, —OCHBr$_2$ or —OCHI$_2$), —OCH$_2$X$^5$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n5 is an integer from 0 to 4 (e.g. 0). m5 and v5 are independently an integer from 1 to 2. X$^5$ is independently —F, —Cl, —Br, or —I.

In embodiments, R$^5$ is hydrogen, —F, —Cl, Br, —I, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —SH, —SCH$_3$, —SOH, —SOCH$_3$, —SO$_2$H, —SO$_2$CH$_3$, —SO$_2$NH$_2$, —SO$_2$NHCH$_3$, —NHNH$_2$, —NHNHCH$_3$, —ONH$_2$, —ONHCH$_3$, —NHC(O)NH—NH$_2$, —NHC(O)NHNHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NCH$_3$SO$_2$H, —NHSO$_2$CH$_3$, —NHC(O)H, —NCH$_3$C(O)H, —NHC(O)CH$_3$, —NHC(O)OH, —NCH$_3$C(O)OH, —NHC(O)OCH$_3$, —NHOH, —NCH$_3$OH, —NHOCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_1$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, R$^5$ is —F, —Cl, Br, —I, —CF$_3$, —CCl$_3$, —CBr$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —SH, —SCH$_3$, —SOH, —SOCH$_3$, —SO$_2$H, —SO$_2$CH$_3$, —SO$_2$NH$_2$, —SO$_2$NHCH$_3$, —NHNH$_2$, —NHNHCH$_3$, —ONH$_2$, —ONHCH$_3$, —NHC(O)NHNH$_2$, —NHC(O)NHNHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NCH$_3$SO$_2$H, —NHSO$_2$CH$_3$, —NHC(O)H, —NCH$_3$C(O)H, —NHC(O)CH$_3$, —NHC(O)OH, —NCH$_3$C(O)OH, —NHC(O)OCH$_3$, —NHOH, —NCH$_3$OH, —NHOCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., C$_6$-C$_{12}$, C$_6$-C$_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

In embodiments, R$^6$ is hydrogen, halogen (e.g., —F, —Cl, —Br, —I), oxo, —CX$^{63}$ (e.g., —CF$_3$, —CCl$_3$, —CBr$_3$ or —C$_3$), —CHX$^{62}$ (e.g., —CHF$_2$, —CHCl$_2$, —CHBr$_2$ or —CHI$_2$), —CH$_2$X$^6$ (e.g., —CH$_2$F, —CH$_2$C, —CH$_2$Br or —CH$_2$I), —N$_3$, —CN, —SO$_{n6}$R$^{64}$ (e.g., —SH, —SCH$_3$, —SOH, —SOCH$_3$, —SO$_2$H, or —SO$_2$CH$_3$), —SO$_6$NR$^{6B}$R$^{6C}$ (e.g., —SO$_2$NH$_2$ or —SO$_2$NHCH$_3$), —NR$^{6B}$R$^{6C}$ (e.g., —NH$_2$ or —NHCH$_3$), —C(O)R$^{6D}$ (e.g., —C(O)H or —C(O)CH$_3$), —C(O)OR$^{6D}$ (e.g., —C(O)OH or —C(O)OCH$_3$), —C(O)NR$^{6B}$R$^{6C}$ (e.g., —C(O)NH$_2$ or —C(O)NHCH$_3$), —OR$^{6A}$ (e.g., —OH or —OCH$_3$), —OCX$^{63}$ (e.g., —OCF$_3$, —OCCl$_3$, —OCBr$_3$ or —OCI$_3$), —OCHX$^6_2$ (e.g., —OCHF$_2$, —OCHCl$_2$, —OCHBr$_2$ or —OCHI$_2$), —OCH$_2$X$^6$ (e.g. —OCH$_2$F, —OCH$_2$Cl, —OCH$_2$Br, or —OCH$_2$I), substituted (e.g., substituted with a substituent group, a size-limited substituent group, or a lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). n6 is an integer from 0 to 4 (e.g. 0). v6 is an integer from 1 to 2. $X^6$ is independently —F, —Cl, —Br, or —I.

In embodiments, $R^6$ is hydrogen, —F, —Cl, Br, —I, oxo, —CF$_3$, —CCl$_3$, —CBr$_3$, —CI$_3$, —CHF$_2$, —CHCl$_2$, —CHBr$_2$, —CHI$_2$, —CH$_2$F, —CH$_2$C, —CH$_2$Br, —CH$_2$I, —N$_3$, —CN, —SH, —SCH$_3$, —SOH, —SOCH$_3$, —SO$_2$H, —SO$_2$CH$_3$, —SO$_2$NH$_2$, —SO$_2$NHCH$_3$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g., substituted with a substituent group, a size-limited substituent group, or a lower substituent group) or unsubstituted alkyl (e.g., $C_1$-$C_{20}$, $C_1$-$C_2$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_2$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

In embodiments, $R^{6B}$ and $R^{6C}$ together with atoms attached thereto are joined to form substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{6B}$ and $R^{6C}$ together with atoms attached thereto are joined to form substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, $R^{6B}$ and $R^{6C}$ together with atoms attached thereto are joined to form unsubstituted heterocycloalkyl (e.g., 3 to 10 membered, 3 to 8 membered, 3 to 6 membered, 4 to 6 membered, 4 to 5 membered, or 5 to 6 membered), or unsubstituted heteroaryl (e.g., 5 to 12 membered, 5 to 10 membered, 5 to 9 membered, or 5 to 6 membered).

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$ and $R^{6D}$ are independently hydrogen, halogen (e.g., —F, —Cl, —Br, —I), —CF$_3$, —CCl$_3$, —CBr$_3$, —CI$_3$, —COOH, —CONH$_2$, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered). In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^4$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$ and $R^{6D}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —COOH, —CONH$_2$, substituted (e.g., substituted with a substituent group, a size-limited substituent group, or a lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted aryl (e.g., $C_6$-$C_{12}$, $C_6$-$C_{10}$, or phenyl), or substituted (e.g., substituted with a substituent group, a size-limited substituent group, or a lower substituent group) or unsubstituted heteroaryl (e.g., 5 to 12 membered, 5 to 10 membered, 5 to 9 membered, or 5 to 6 membered).

$X^1$, $X^2$, $X^3$, $X^{3.1}$, $X^{3.2}$ $X^4$, $X^5$ and $X^6$ are independently —F, —Cl, —Br, or —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, $X^{3.1}$ is —F. In embodiments, $X^{3.1}$ is —Cl. In embodiments, $X^{3.1}$ is —Br. In embodiments, $X^{3.1}$ is —I. In embodiments, $X^{3.2}$ is —F. In embodiments, $X^{3.2}$ is —Cl. In embodiments, $X^{3.2}$ is —Br. In embodiments, $X^{3.2}$ is —I. In embodiments, $X^4$ is —F. In embodiments, $X^4$ is —Cl. In embodiments, $X^4$ is —Br. In embodiments, $X^4$ is —I. In embodiments, $X^5$ is —F. In embodiments, $X^5$ is —Cl. In embodiments, $X^5$ is —Br. In embodiments, $X^5$ is —I. In embodiments, $X^6$ is —F. In embodiments, $X^6$ is —Cl. In embodiments, $X^6$ is —Br. In embodiments, $X^6$ is —I.

n1, n2, n3, n3.1, n3.2, n4, n5 and n6 are independently an integer from 0 to 4 (e.g. 0). In embodiments, n1 is 0. In embodiments, n1 is 1. In embodiment, n1 is 2. In embodiments, n1 is 3. In embodiment, n1 is 4. In embodiments, n2 is 0. In embodiments, n2 is 1. In embodiments, n2 is 2. In embodiments, n2 is 3. In embodiment, n2 is 4. In embodiments, n3 is 0. In embodiments, n3 is 1. In embodiment, n3 is 2. In embodiments, n3 is 3. In embodiment, n3 is 4. In embodiments, n3.1 is 0. In embodiments, n3.1 is 1. In embodiment, n3.1 is 2. In embodiments, n3.1 is 3. In embodiment, n3.1 is 4. In embodiments, n3.2 is 0. In embodiments, n3.2 is 1. In embodiment, n3.2 is 2. In embodiments, n3.2 is 3. In embodiment, n3.2 is 4. In embodiments, n4 is 0. In embodiments, n4 is 1. In embodiment, n4 is 2. In embodiments, n4 is 3. In embodiment, n4 is 4. In embodiments, n5 is 0. In embodiments, n5 is 1. In embodiment, n5 is 2. In embodiments, n5 is 3. In embodiment, n5 is 4. In embodiments, n6 is 0. In embodiments, n6 is 1. In embodiment, n6 is 2. In embodiments, n6 is 3. In embodiment, n6 is 4.

m2, m3, m3.1, m3.2 and m5 are independently an integer from 1 to 2. In embodiments, m2 is 1. In embodiment, m2 is 2. In embodiments, m3 is 1. In embodiment, m3 is 2. In embodiments, m3.1 is 1. In embodiment, m3.1 is 2. In embodiments, m3.2 is 1. In embodiment, m3.2 is 2. In embodiments, m5 is 1. In embodiment, m5 is 2.

v1, v2, v3, v3.1, v3.2, v4, v5 and v6 are independently an integer from 1 to 2. In embodiments, v is 1. In embodiment, v1 is 2. In embodiments, v2 is 1. In embodiment, v2 is 2. In embodiments, v3 is 1. In embodiment, v3 is 2. In embodiments, v3.1 is 1. In embodiment, v3.1 is 2. In embodiments, v3.2 is 1. In embodiment, v3.2 is 2. In embodiments, v4 is 1. In embodiment, v4 is 2. In embodiments, v5 is 1. In embodiment, v5 is 2. In embodiments, v6 is 1. In embodiment, v6 is 2.

L is a bond, substituted (e.g., substituted with a substituent group, a size-limited substituent group, or a lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or a lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or a lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or a lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or a lower substituent group) or unsubstituted arylene (e.g., $C_6$-$C_{12}$, $C_6$-$C_{10}$, or phenyl), or substituted (e.g., substituted with a substituent group, a size-limited substituent group, or a lower substituent group) or unsubstituted heteroarylene (e.g., 5 to 12 membered, 5 to 10 membered, 5 to 9 membered, or 5 to 6 membered).

In embodiments, when X is =O or S and Y is =O or S, then at least one of $R^2$, $R^3$ and $R^4$ is not hydrogen. In embodiments, when X is =O and Y is =S, then at least one of $R^2$, $R^3$ and $R^4$ is not hydrogen. In embodiments, when X is =S and Y is =O, then at least one of $R^2$, $R^3$ and $R^4$ is not hydrogen. In embodiments, when X is =S and Y is =S, then at least one of $R^2$, $R^3$ and $R^4$ is not hydrogen. In embodiments, when X is =O and Y is =O, then at least one of $R^2$, $R^3$ and $R^4$ is not hydrogen. In embodiments, when X is =O or S, Y is =O or S, then $R^2$, $R^3$ and $R^4$ are not hydrogen. In embodiments, when X is =O, Y is =O, $R^2$ and $R^4$ are hydrogen, then $R^3$ is not hydrogen. In embodiments, when X is =O, Y is =O, $R^3$ and $R^4$ are hydrogen, then $R^2$ is not hydrogen. In embodiments, when X is =O, Y is =O, $R^2$ and $R^3$ are hydrogen, then $R^4$ is not hydrogen. In embodiments, when X is =O, Y is =O, $R^2$, $R^{3.1}$ and $R^4$ are hydrogen, then $R^{3.2}$ is not hydrogen. In embodiments, when X is =O, Y is =O, $R^2$, $R^{3.2}$ and $R^4$ are hydrogen, then $R^{3.1}$ is not hydrogen. In embodiments, when X is =O or S, Y is =O or S, and $R^3$ and $R^4$ are hydrogen, then $R^2$ is not hydrogen. In embodiments, when X is =O or S, Y is =O or S, and $R^2$ and $R^4$ are hydrogen, then $R^3$ is not hydrogen. In embodiments, when X is =O or S, Y is =O or S, and $R^2$ and $R^3$ are hydrogen, then $R^4$ is not hydrogen.

In embodiments, when X is =O or S and Y is =O or S, then at least one of $R^2$, $R^3$ and $R^4$ is halogen. In embodiments, when X is =O and Y is =O, then at least one of $R^2$, $R^3$ and $R^4$ is halogen. In embodiments, when X is =O, Y is =O, and $R^2$ and $R^4$ are hydrogen, then $R^3$ is halogen. In embodiments, when X is =O, Y is =O, and $R^2$ and $R^4$ are hydrogen, then $R^{3.1}$ is halogen. In embodiments, when X is =O, Y is =O, and $R^2$ and $R^4$ are hydrogen, then $R^{3.2}$ is halogen. In embodiments, when X is =O or S and Y is =O or S, then at least one of $R^2$, $R^3$ and $R^4$ is —CN. In embodiments, when X is =O and Y is =O, then at least one of $R^2$, $R^3$ and $R^4$ is —CN. In embodiments, when X is =O, Y is =O, and $R^2$ and $R^4$ are hydrogen, then $R^3$ is —CN. In embodiments, when X is =O, Y is =O, and $R^2$ and $R^4$ are hydrogen, then $R^{3.1}$ is —CN. In embodiments, when X is =O, Y is =O, and $R^2$ and $R^4$ are hydrogen, then $R^{3.2}$ is —CN. In embodiments, when X is =O or S and Y is =O or S, then at least one of $R^2$, $R^3$ and $R^4$ is —C(O)OCH$_3$. In embodiments, when X is =O and Y is =O, then at least one of $R^2$, $R^3$ and $R^4$ is —C(O)OCH$_3$. In embodiments, when X is =O, Y is =O, and $R^2$ and $R^4$ are hydrogen, then $R^3$ is —C(O)OCH$_3$. In embodiments, when X is =O, Y is =O, and $R^2$ and $R^4$ are hydrogen, then $R^{3.1}$ is —C(O)OCH$_3$. In embodiments, when X is =O, Y is =O, and $R^2$ and $R^4$ are hydrogen, then $R^{3.2}$ is —C(O)OCH$_3$. In embodiments, when X is =O and Y is =O, $R^2$ is not hydrogen. In embodiments, when X is =O and Y is =O, $R^3$ is not hydrogen. In embodiments, when X is =O and Y is =O, $R^{3.1}$ is not hydrogen. In embodiments, when X is =O and Y is =O, $R^{3.2}$ is not hydrogen. In embodiments, when X is =O and Y is =O, $R^4$ is not hydrogen. In embodiments, $R^2$ is not hydrogen. In embodiments, $R^3$ is not hydrogen. In embodiments, $R^{3.1}$ is not hydrogen. In embodiments, $R^{3.1}$ is not hydrogen. In embodiments, $R^4$ is not hydrogen.
In embodiments, the compound is:
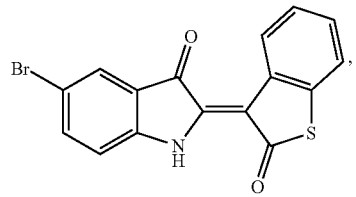
6b
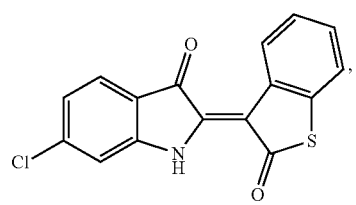
6c
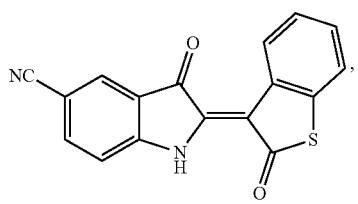
6d
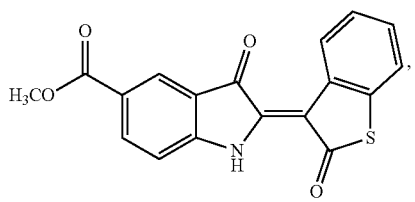
6e
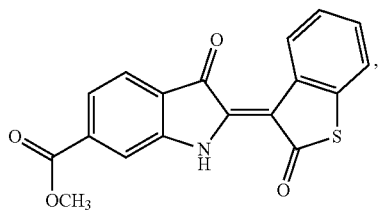
6f
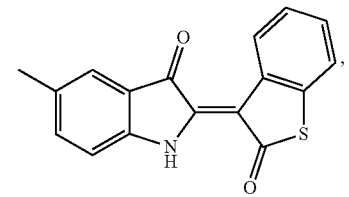
6g
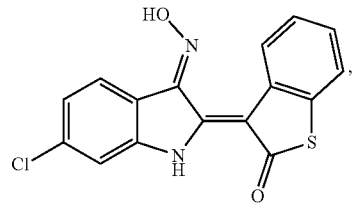
7c
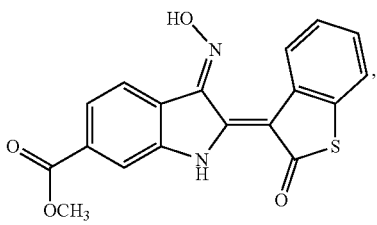
7f
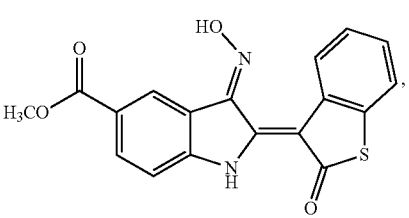
7e
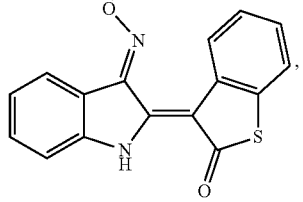
9a
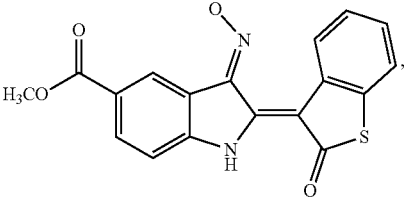
9b

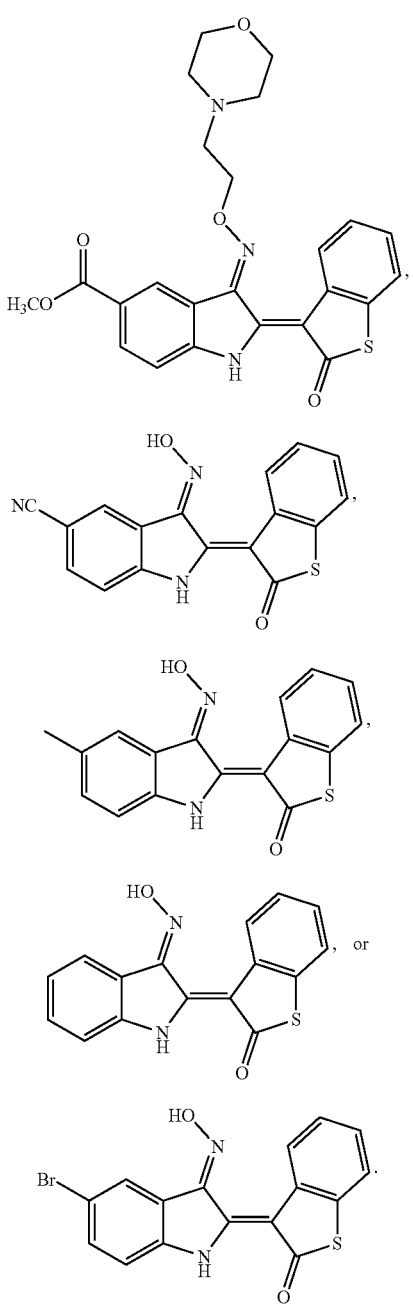

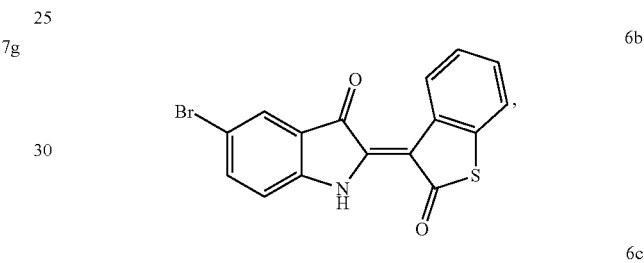

In embodiments, the compound has the formula 6b, or a pharmaceutically acceptable salt thereof. In embodiments, the compound has the formula 6c, or a pharmaceutically acceptable salt thereof. In embodiments, the compound has the formula 6d, or a pharmaceutically acceptable salt thereof. In embodiments, the compound has the formula 6e, or a pharmaceutically acceptable salt thereof. In embodiments, the compound has the formula 6f, or a pharmaceutically acceptable salt thereof. In embodiments, the compound has the formula 6g, or a pharmaceutically acceptable salt thereof. In embodiments, the compound has the formula 7a, or a pharmaceutically acceptable salt thereof. In embodiments, the compound has the formula 7b, or a pharmaceutically acceptable salt thereof. In embodiments, the compound has the formula 7c, or a pharmaceutically acceptable salt thereof. In embodiments, the compound has the formula 7d, or a pharmaceutically acceptable salt thereof. In embodiments, the compound has the formula 7e, or a pharmaceutically acceptable salt thereof. In embodiments, the compound has the formula 7f, or a pharmaceutically acceptable salt thereof. In embodiments, the compound has the formula 7g, or a pharmaceutically acceptable salt thereof. In embodiments, the compound has the formula 9a, or a pharmaceutically acceptable salt thereof. In embodiments, the compound has the formula 9b, or a pharmaceutically acceptable salt thereof. In embodiments, the compound has the formula 9c, or a pharmaceutically acceptable salt thereof.

II. PHARMACEUTICAL COMPOSITIONS

Also provided herein are pharmaceutical formulations. In embodiments, the pharmaceutical formulation includes a compound (e.g., formula (I), (I-A), (I-B), (II), (III-A), (III-B), (IV-A), or (IV-B)) described above (including all embodiments thereof) and a pharmaceutically acceptable excipient.

In embodiments, the pharmaceutical composition includes a compound of

-continued
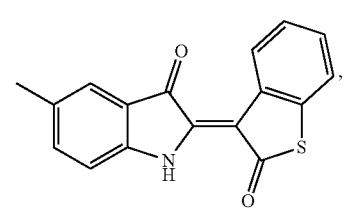
6g
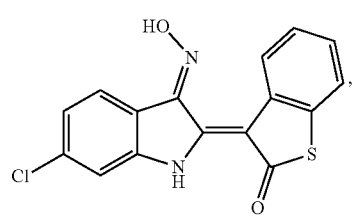
7c
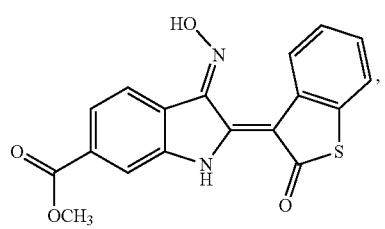
7f
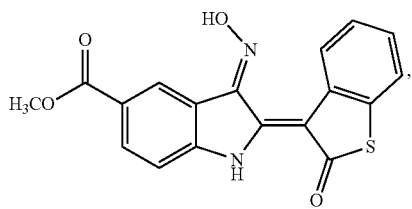
7e
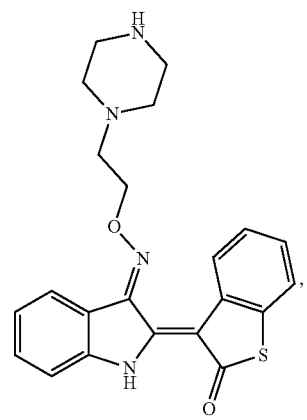
9a
-continued
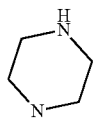
9b
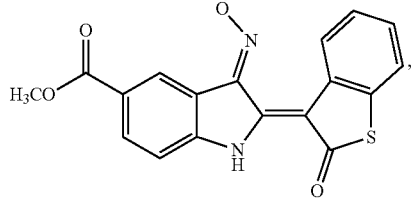
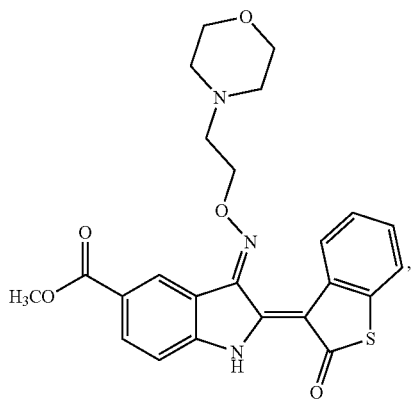
9c
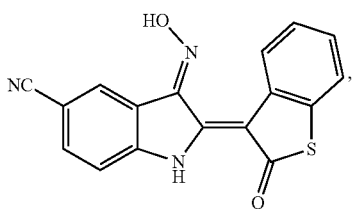
7d
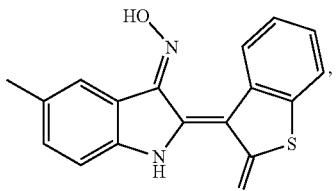
7g
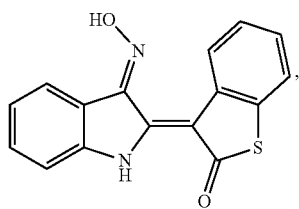
7a 7b

[Structure: 5-bromo-3-(hydroxyimino)indolin-2-ylidene-benzothiophen-2(3H)-one]

or

6a

[Structure: indolin-2,3-dione-benzothiophen-2(3H)-one hybrid]

In embodiments, the compound of the pharmaceutical composition has the formula 6a, or a pharmaceutically acceptable salt thereof. In embodiments, the compound of the pharmaceutical composition has the formula 6b, or a pharmaceutically acceptable salt thereof. In embodiments, the compound of the pharmaceutical composition has the formula 6c, or a pharmaceutically acceptable salt thereof. In embodiments, the compound of the pharmaceutical composition has the formula 6d, or a pharmaceutically acceptable salt thereof. In embodiments, the compound of the pharmaceutical composition has the formula 6e, or a pharmaceutically acceptable salt thereof. In embodiments, the compound of the pharmaceutical composition has the formula 6f, or a pharmaceutically acceptable salt thereof. In embodiments, the compound of the pharmaceutical composition has the formula 6g, or a pharmaceutically acceptable salt thereof. In embodiments, the compound of the pharmaceutical composition has the formula 7a, or a pharmaceutically acceptable salt thereof. In embodiments, the compound of the pharmaceutical composition has the formula 7b, or a pharmaceutically acceptable salt thereof. In embodiments, the compound of the pharmaceutical composition has the formula 7c, or a pharmaceutically acceptable salt thereof. In embodiments, the compound of the pharmaceutical composition has the formula 7d, or a pharmaceutically acceptable salt thereof. In embodiments, the compound of the pharmaceutical composition has the formula 7e, or a pharmaceutically acceptable salt thereof. In embodiments, the compound of the pharmaceutical composition has the formula 7f, or a pharmaceutically acceptable salt thereof. In embodiments, the compound of the pharmaceutical composition has the formula 7g, or a pharmaceutically acceptable salt thereof. In embodiments, the compound of the pharmaceutical composition has the formula 9a, or a pharmaceutically acceptable salt thereof. In embodiments, the compound of the pharmaceutical composition has the formula 9b, or a pharmaceutically acceptable salt thereof. In embodiments, the compound of the pharmaceutical composition has the formula 9c, or a pharmaceutically acceptable salt thereof.

The pharmaceutical compositions described herein, including embodiments thereof may be used in the treatment of cancers. In embodiments, the pharmaceutical compositions described herein, including embodiments thereof may be used in the treatment of lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer or prostate cancer. In embodiments, the pharmaceutical compositions described herein, including embodiments thereof may be used in the treatment of a solid tumor or a blood tumor.

Further provided herein is a pharmaceutical composition including a pharmaceutically acceptable excipient and a compound, or pharmaceutically acceptable salt thereof, as described herein (e.g. a compound of formula (I), (I-A), (I-B), (II), (III-A), (III-B), (IV-A), or (IV-B) including embodiments thereof). In embodiments, the pharmaceutical composition includes a compound, or pharmaceutically acceptable salt thereof, as described herein (e.g. a compound of formula (I), (I-A), (I-B), (II), (III-A), (III-B), (IV-A), or (IV-B), including embodiments thereof) in a therapeutically effective amount. In embodiments, the pharmaceutical composition includes a second agent (e.g. therapeutic agent). In embodiments, the pharmaceutical composition includes a second agent (e.g. therapeutic agent) in a therapeutically effective amount. In embodiments, the second agent (e.g. therapeutic agent) is an anti-cancer agent. In embodiments, the second agent (e.g. therapeutic agent) is a chemotherapeutic.

In embodiments, the pharmaceutical composition includes a compound described herein (e.g., in an aspect, embodiment, example, table, figure, scheme, appendix, or claim) and a pharmaceutically acceptable excipient.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. METHODS OF TREATMENT

Also provided herein is a method of treating cancer by administering to a subject in need thereof a therapeutically effective amount of a compound (e.g. formula (I), (I-A), (I-B), (II), (III-A), (III-B), (IV-A), or (IV-B)) described above including all embodiments thereof), or pharmaceutically acceptable salt thereof.

The cancer may be, for example, lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer or prostate cancer. The method of treating cancer may be a method of treating lung cancer. The method of treating cancer may be a method of treating breast cancer. The method of treating cancer may be a method of treating ovarian cancer. The method of treating cancer may be a method of treating lymphoma. The method of treating cancer may be a method of treating pancreatic cancer. The method of treating cancer may be a method of treating melanoma. The method of treating cancer may be a method of treating prostate cancer. The method of treating cancer may be a method of treating sarcoma. The method of treating cancer may be a method of treating bladder cancer. The method of treating cancer may be a method of treating bone cancer. The method of treating cancer may be a method of treating brain cancer. The method of treating cancer may be a method of treating cervical cancer. The method of treating cancer may be a method of treating colon cancer. The method of treating cancer may be a method of treating esophageal cancer. The method of treating cancer may be a method of treating gastric cancer. The method of treating cancer may be a method of treating liver cancer. The method of treating cancer may be a method of treating head and neck cancer.

The method of treating cancer may be a method of treating kidney cancer. The method of treating cancer may be a method of treating myeloma. The method of treating cancer may be a method of treating multiple myeloma. The method of treating cancer may be a method of treating thyroid cancer. In embodiments, the compounds set forth herein are provided as pharmaceutical compositions including the compound and a pharmaceutically acceptable excipient.

The cancer may be, for example, a solid tumor or a blood tumor. The method of treating cancer may be a method of treating a solid tumor. The method of treating cancer may be a method of treating a blood tumor.

The compound may be administered as described herein, including embodiments, thereof. The method may include co-administering an effective amount of an anti-cancer agent as described herein. In embodiments, the anti-cancer agent is a chemotherapeutic agent.

Also provided herein are methods of modulating the level, activity, or function of a protein associated with a disease (e.g. cancer). The method includes contacting the protein with an effective amount of a compound, or pharmaceutically acceptable salt thereof, as described herein, including embodiments thereof.

In embodiments, the method of modulation includes administering an effective amount of a compound (e.g. formula (I), (I-A), (I-B), (II), (III-A), (III-B), (IV-A), or (IV-B)) described above including all embodiments thereof), or pharmaceutically acceptable salt thereof, as described herein including embodiments thereof. In embodiments, the protein is selected from the group consisting of a JAK, JAK2, TYK2, Src, c-Src, ABL1, ABL1 T315I, an Aurora kinase (e.g. Aurora A), GSK-3b or a CDK. The protein may be a JAK. The protein may be JAK2. The protein may be TYK2. The protein may be a Src. The protein may be c-Src. The protein may be ABL1. The protein may be an ABL1 T315I. The protein may be an Aurora kinase. The protein may be Aurora A. The protein may be GSK-3b. The protein may be CDK. In embodiments, the method of modulation includes modulating different proteins (e.g. kinases). In embodiments, the method of modulation includes modulating two, three, four, five, or six proteins (e.g. kinases).

The method may include modulating the level (e.g. amount) of a protein associated with a disease (e.g. cancer). The method may include modulating the activity of a protein associated with a disease (e.g. cancer). The method may include modulating function of a protein associated with a disease (e.g. cancer). In embodiments, modulating is inhibiting and the compound, or pharmaceutically acceptable salt thereof, as described herein (including embodiments) is an inhibitor. In embodiments, the compounds set forth herein are provided as pharmaceutical compositions including the compound and a pharmaceutically acceptable excipient.

Provided herein is a method of modulating STAT or STAT3. The method includes contacting STAT or STAT3 with a compound (e.g. formula (I), (I-A), (I-B), (II), (III-A), (III-B), (IV-A), or (IV-B)) described above including all embodiments thereof), or pharmaceutically acceptable salt thereof. In embodiments, the method including activating STAT or STAT3. In embodiments, the method including inhibiting STAT or STAT3.

IV. EMBODIMENTS

Embodiments P

Embodiment P1

A compound, or pharmaceutically acceptable salt thereof, having the formula:

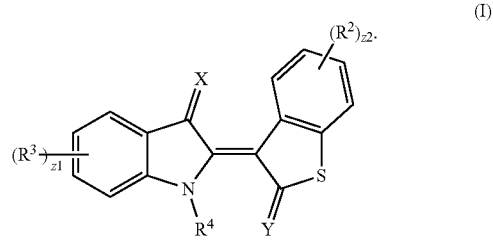

(I)

X, Y, $R^3$, $R^4$, $R^5$, z and z2 are as described herein.

Embodiment P2

A compound, or pharmaceutically acceptable salt thereof, having the formula:

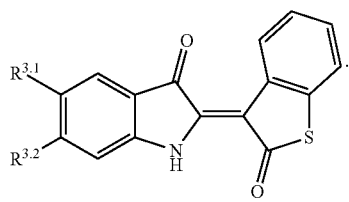

(I-A)

$R^3$ and $R^{3.2}$ are as described herein

Embodiment P3

A compound, or pharmaceutically acceptable salt thereof, having the formula:

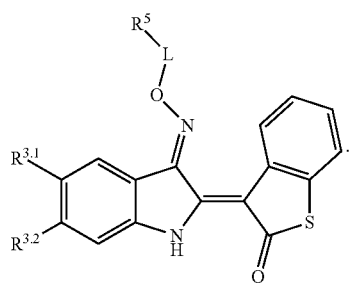

(I-B)

$R^3$ and $R^{3.2}$ are as described herein

Embodiment P4

A compound, or pharmaceutically acceptable salt thereof, having the formula:

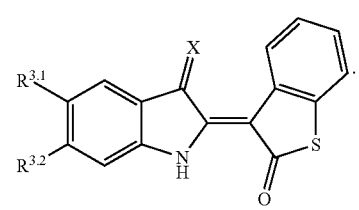

(II)

X, $R^{3.1}$, and $R^{3.2}$ are as described herein.

Embodiment P5

A compound, or pharmaceutically acceptable salt thereof, having the the following structures:

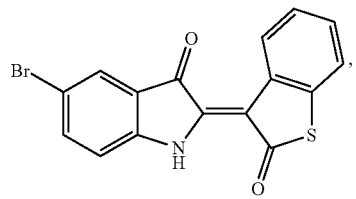

6b

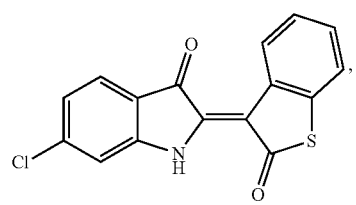

6c

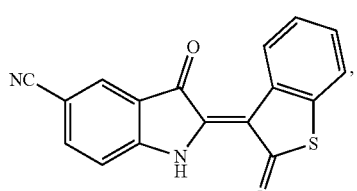

6d

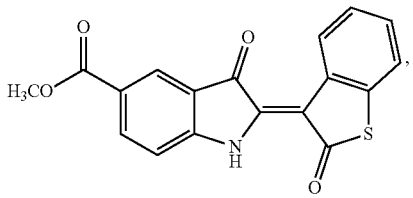

6e

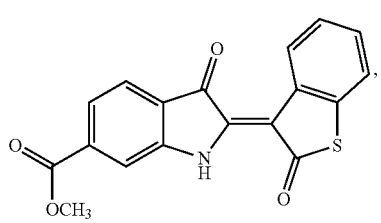

6f

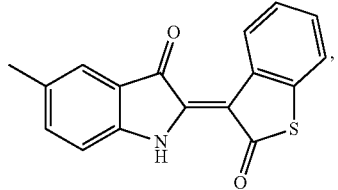

6g

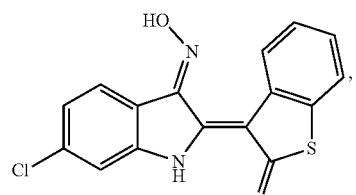

7c

7f
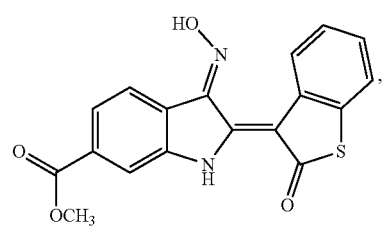
7e
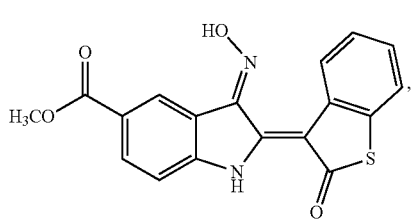
9a
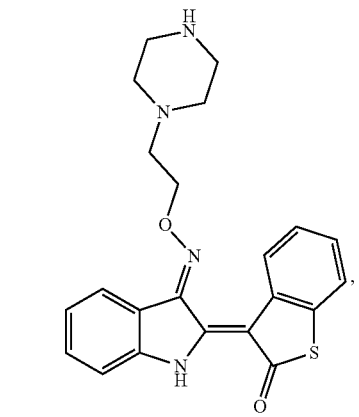
9b
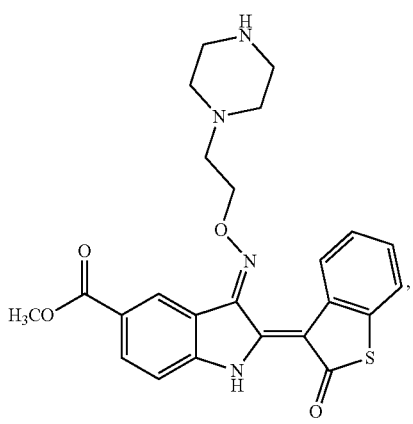
9c
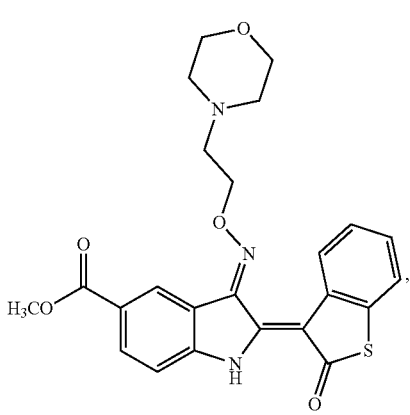
7d
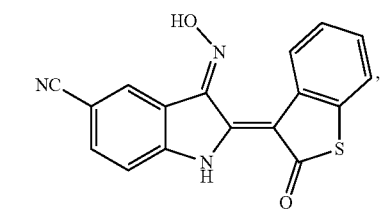
7g
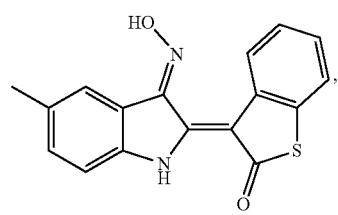
7a
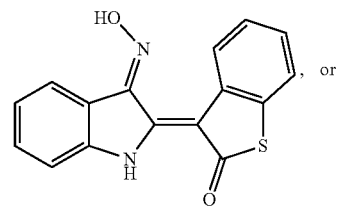, or
7b
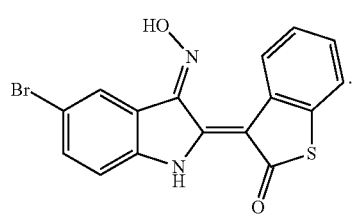

Embodiment P6

A pharmaceutical composition comprising a pharmaceutically acceptable excipient and a compound, or pharmaceutically acceptable salt thereof, having structural formula:

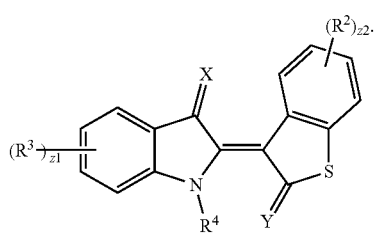

(I)

X, Y, R³, R⁴, R⁵, z1 and z2 are as described herein.

Embodiment P7

A method of treating cancer, comprising administering to a subject in need thereof a therapeutically effective amount of a compound (e.g. formula (I), (I-A), (I-B), (II), (III-A), (III-B), (IV-A), or (IV-B)) described above (including all embodiments thereof), or pharmaceutically acceptable salt thereof.

Embodiment P8

A method of modulating a kinase, comprising contacting the kinase with a compound (e.g. formula (I), (I-A), (I-B), (II), (III-A), (III-B), (IV-A), or (IV-B)) described above (including all embodiments thereof), or pharmaceutically acceptable salt thereof.

Embodiment P9

A method of modulating STAT or STAT3, comprising contacting STAT or STAT3 with a compound (e.g. formula (I), (I-A), (I-B), (II), (III-A), (III-B), (IV-A), or (IV-B)) described above (including all embodiments thereof), or pharmaceutically acceptable salt thereof.

Embodiment P10

A compound of embodiments P6-P9 having formula:

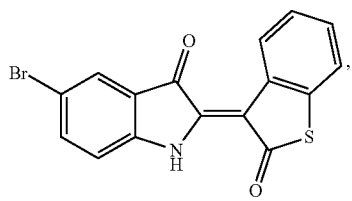
6b

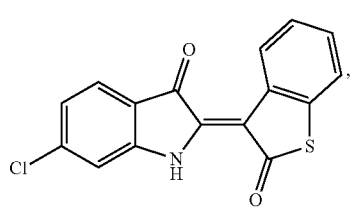
6c

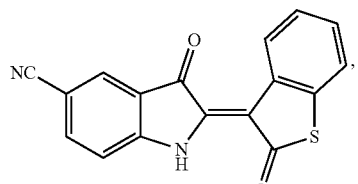
6d

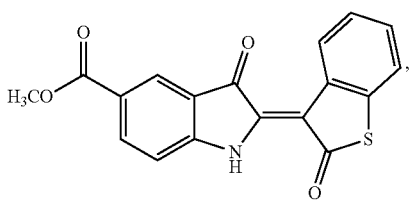
6e

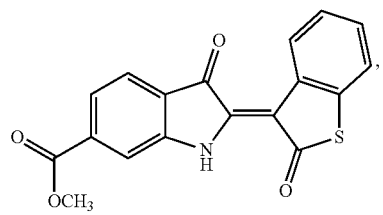
6f

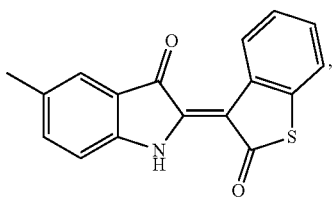
6g

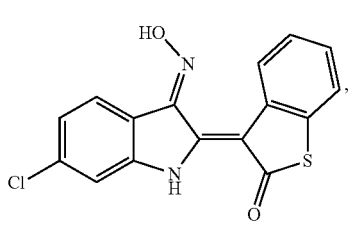
7c

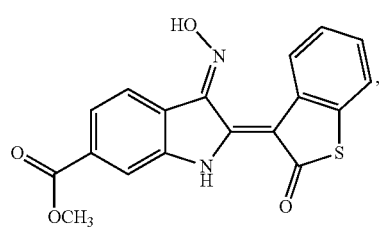
7f

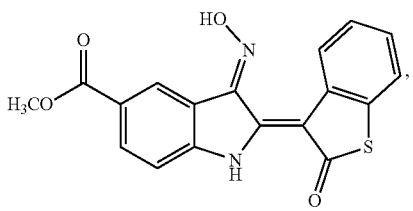
7e

-continued

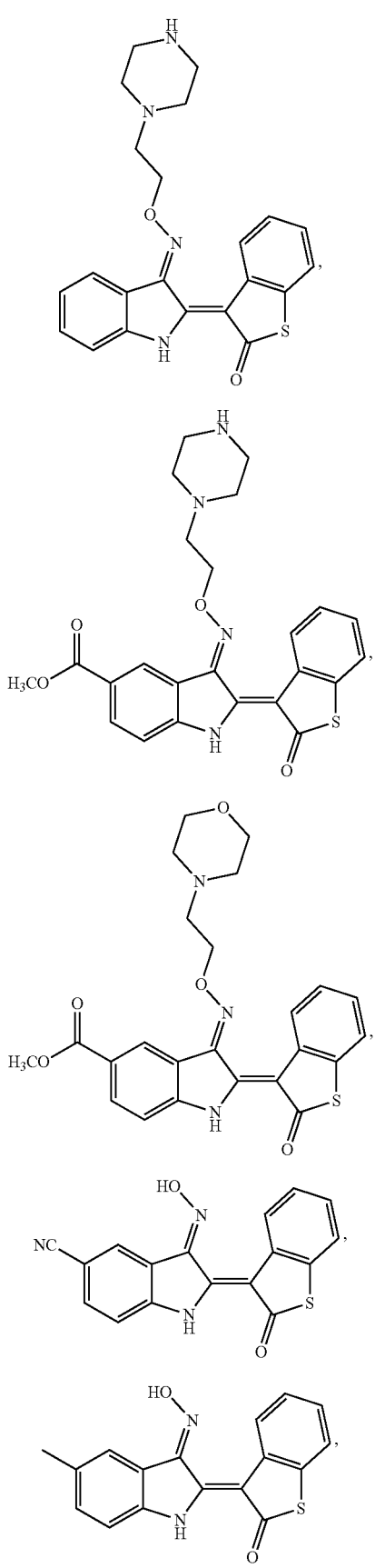

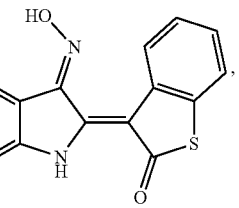

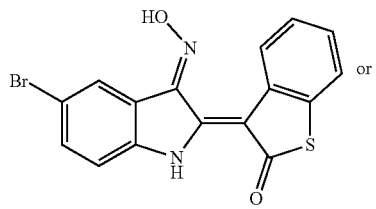

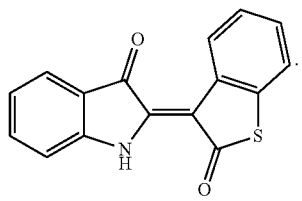

Embodiments Q

Embodiment Q1

A compound, or pharmaceutically acceptable salt thereof, having structural Formula (I):

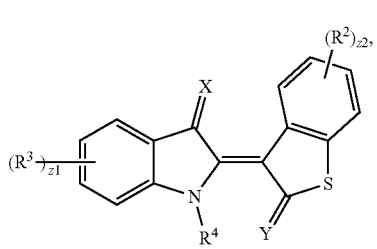

(I)

wherein:
n1, n2, n3, n4 and n6 are independently an integer from 0 to 4;
m2, m3, v1, v2, v3, v4 and v6 are independently 1 or 2;
z1 and z2 are independently an integer from 0 to 4;
X is =O, =S or =NR$^1$;
Y is =O, =S or =NR$^6$.
R$^1$ is hydrogen, halogen, oxo, —CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2{}_3$, —OCHX$^2{}_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, halogen, —CX$^3{}_3$, —CHX$^3{}_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3{}_3$, —OCHX$^3{}_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^4$ is hydrogen, halogen, oxo, —CX$^4{}_3$, —CHX$^4{}_2$, —CH$_2$X$^4$, —CN, —SO$_{n4}$R$^{4A}$, —SO$_2$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4{}_3$, —OCHX$^4{}_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^6$ is hydrogen, halogen, oxo, —CX$^6{}_3$, —CHX$^6{}_2$, —CH$_2$X$^6$, —N$_3$, —CN, —SO$_6$R$^{6A}$, —SO$_6$NR$^{6B}$R$^{6C}$, —NR$^{6B}$R$^{6C}$, —C(O)R$^{6D}$, —C(O)OR$^{6D}$, —C(O)NR$^{6B}$R$^{6C}$, —OR$^{6A}$, —OCX$^6{}_3$, —OCHX$^6{}_2$, —OCH$_2$X$^6$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{6A}$, R$^{6B}$, R$^{6C}$ and R$^{6D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$, R$^{4B}$ and R$^{4C}$ and R$^{6B}$ and R$^{6C}$ substituents bonded to the same nitrogen atom may optionally be joined to form a substituted or unsubstituted heterocycloalkyl or substituted or unsubstituted heteroaryl; and X$^1$, X$^2$, X$^3$, X$^4$ and X$^6$ are independently —Cl, —Br, —I or —F, provided that when X is =O and Y is =O, then at least one of R$^2$, R$^3$ and R$^4$ is not hydrogen.

Embodiment Q2

The compound of Embodiment Q1, wherein z2 is O.

Embodiment Q3

The compound of Embodiment Q1 or Q2, wherein R$^4$ is hydrogen or substituted or unsubstituted alkyl.

Embodiment Q4

The compound of anyone of Embodiments Q1-Q3, wherein X is =O

Embodiment Q5

The compound of any one of Embodiments Q1-Q4, wherein the compound has structural Formula (I-A):

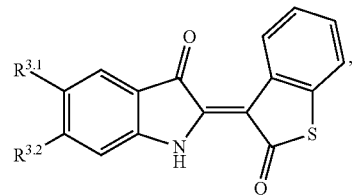

(I-A)

wherein:

n3.1 and n3.2 are independently an integer from 0 to 4; m3.1, m3.2, v3.1 and v3.2 are independently 1 or 2;

R$^{3.1}$ is hydrogen, halogen, —CX$^{3.1}{}_3$, —CHX$^{3.1}{}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}{}_3$, —OCHX$^{3.1}{}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{3.2}$ is hydrogen, halogen, —CX$^{3.2}{}_3$, —CHX$^{3.2}{}_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}{}_3$, —OCHX$^{3.2}{}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{3.1A}$, R$^{3.1B}$, R$^{3.1C}$, R$^{3.1D}$, R$^{3.2A}$, R$^{3.2B}$, R$^{3.2C}$ and R$^{3.2D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.1B}$ and R$^{3.1C}$ and R$^{3.2B}$ and R$^{3.2C}$, substituents bonded to the same nitrogen atom may optionally be joined to form a substituted or unsubstituted heterocycloalkyl or substituted or unsubstituted heteroaryl; and X$^{3.1}$ and X$^{3.2}$ are independently —Cl, —Br, —I or —F.

Embodiment Q6

The compound of any one of Embodiment Q1-Q3, wherein X is =NR$^1$.

Embodiment Q7

The compound of any one of Embodiments Q1-Q3 and Q6, wherein R$^1$ is —OH.

Embodiment Q8

The compound of any one of Embodiments Q1-Q3 and Q6, or a pharmaceutically acceptable salt thereof, wherein the compound has structural Formula (I-B):

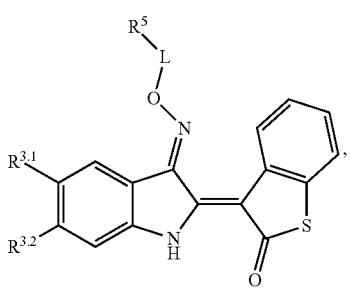

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^{3.1}$ is hydrogen, halogen, $—CX^1_3$, $—CHX^{3.1}_2$, $—CH_2X^{3.1}$, $—N_3$, $—CN$, $—SO_{n3.1}R^{3.1A}$, $—SO_{v3.1}NR^{3.1B}R^{3.1C}$, $—NHNR^{3.1B}R^{3.1C}$, $—ONR^{3.1B}R^{3.1C}$, $—NHC(O)NHNR^{3.1B}R^{3.1C}$, $—NHC(O)NR^{3.1B}R^{3.1C}$, $—N(O)_{m3.1}$, $—NR^{3.1B}R^{3.1C}$, $—C(O)R^{3.1D}$, $—C(O)OR^{3.1D}$, $—C(O)NR^{3.1B}R^{3.1C}$, $—OR^{3.1A}$, $—NR^{3.1B}SO_2R^{3.1A}$, $—NR^{3.1B}C(O)R^{3.1D}$, $—NR^{3.1B}C(O)OR^{3.1D}$, $—NR^{3.1B}OR^{3.1D}$, $—OCX^{3.1}_3$, $—OCHX^{3.1}_2$, $—OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, $—CX^{3.2}_3$, $—CHX^{3.2}_2$, $—CH_2X^{3.2}$, $—N_3$, $—CN$, $—SO_{n3.2}R^{3.2A}$, $—SO_{v3.2}NR^{3.2B}R^{3.2C}$, $—NHNR^{3.2B}R^{3.2C}$, $—ONR^{3.2B}R^{3.2C}$, $—NHC(O)NHNR^{3.2B}R^{3.2C}$, $—NHC(O)NR^{3.2B}R^{3.2C}$, $—N(O)_{m3.2}$, $—NR^{3.2B}R^{3.2C}$, $—C(O)R^{3.2D}$, $—C(O)OR^{3.2D}$, $—C(O)NR^{3.2B}R^{3.2C}$, $—OR^{3.2A}$, $—NR^{3.2B}SO_2R^{3.2A}$, $—NR^{3.2B}C(O)R^{3.2D}$, $—NR^{3.2B}C(O)OR^{3.2D}$, $—NR^{3.2B}OR^{3.2D}$, $—OCX^{3.2}_3$, $—OCHX^{3.2}_2$, $—OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^5$ is hydrogen, halogen, $—CX^5_3$, $—CHX^5_2$, $—CH_2X^5$, $—CN$, $—N_3$, $—SO_{n5}R^{5A}$, $—SO_{v5}NR^{5B}R^{5C}$, $—NHNR^{5B}R^{5C}$, $—ONR^{5B}R^{5C}$, $—NHC(O)NHNR^{5B}R^{5C}$, $—NHC(O)NR^{5B}R^{5C}$, $—N(O)_{m5}$, $—NR^{5B}R^{5C}$, $—C(O)R^{5D}$, $—C(O)OR^{5D}$, $—C(O)NR^{5B}R^{5C}$, $—OR^{5A}$, $—NR^{5B}SO_2R^{5A}$, $—NR^{5B}C(O)R^{5D}$, $—NR^{5B}C(O)OR^{5D}$, $—NR^{5B}OR^{5D}$, $—OCX^5_3$, $—OCHX^5_2$, $—OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, $—CF_3$, $—CCl_3$, $—CBr_3$, $—C_3$, $—COOH$, $—CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and
$X^{3.1}$, $X^{3.2}$ and $X^5$ are independently —Cl, —Br, —I or —F.

Embodiment Q9

The compound of Embodiment Q5 or Q8, wherein $R^{3.1}$ and $R^3_2$ are independently hydrogen, halogen, —CN, substituted or unsubstituted alkyl or substituted or unsubstituted heteroalkyl.

Embodiment Q10

The compound of Embodiments Q8, wherein L is unsubstituted alkylene.

Embodiment Q11

The compound of Embodiments Q8, wherein L is unsubstituted $C_1$-$C_8$ alkylene.

Embodiment Q12

The compound of Embodiments Q8, wherein L is unsubstituted $C_1$-$C_4$ alkylene.

Embodiment Q13

The compound of Embodiments Q8, wherein L is unsubstituted $C_2$ alkylene.

Embodiment Q14

The compound of Embodiments Q8, wherein L is a bond.

Embodiment Q15

The compound of Embodiments Q8, wherein $R^5$ is halogen, $—CX^5_3$, $—OCX^5_3$, —CN, —OH, $—NH_2$, —COOH, $—C(O)OR^{5D}$, $—CONH_2$, $—NO_2$, SH, $—NHNH_2$, $—NR^{5B}R^{5C}$, $—OR^A$, $—SR^A$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment Q16

The compound of Embodiments Q8, wherein $R^5$ is —OH or $—NR^{5B}R^{5C}$.

Embodiment Q17

The compound of Embodiments Q16, wherein $R^{5B}$ and $R^{5C}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment Q18

The compound of Embodiments Q17, wherein $R^{5B}$ and $R^{5C}$ are independently substituted or unsubstituted alkyl.

Embodiment Q19

The compound of Embodiments Q8, wherein $R^{5B}$ and $R^{5C}$ are independently substituted or unsubstituted $C_1$-$C_8$ alkyl.

Embodiment Q20

The compound of Embodiments Q19, wherein $R^{5B}$ and $R^{5C}$ are independently substituted or unsubstituted $C_1$-$C_4$ alkyl.

Embodiment Q21

The compound of Embodiments Q20, wherein $R^{5B}$ and $R^{5C}$ are independently unsubstituted $C_1$-$C_4$ alkyl.

Embodiment Q2₂

The compound of Embodiments Q8, wherein $R^{5B}$ and $R^{5C}$ are joined together to form a substituted or unsubstituted heterocycloalkyl or substituted or unsubstituted heteroaryl.

Embodiment Q23

The compound of Embodiments Q22, wherein $R^{5B}$ and $R^{5C}$ are joined together to form a substituted or unsubstituted heterocycloalkyl.

Embodiment Q24

The compound of Embodiments Q23, wherein $R^{5B}$ and $R^{5C}$ are joined together to form a substituted or unsubstituted $C_5$-$C_7$ heterocycloalkyl.

Embodiment Q25

The compound of Embodiments Q24, wherein $R^{5B}$ and $R^{5C}$ are joined together to form a substituted $C_5$-$C_7$ heterocycloalkyl.

Embodiment Q26

The compound of Embodiments Q25, wherein $R^{5B}$ and $R^{5C}$ are joined together to form a substituted or unsubstituted pyrrolidinyl.

Embodiment Q27

The compound of Embodiments Q25, wherein $R^{5B}$ and $R^{5C}$ are joined together to form a substituted or unsubstituted piperazinyl.

Embodiment Q28

The compound of Embodiment Q1, wherein the compound is:

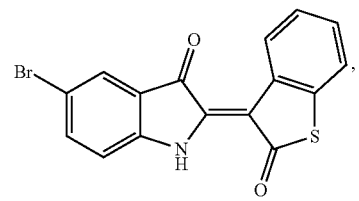

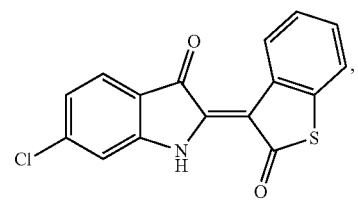

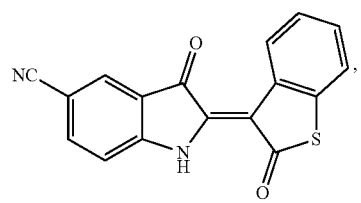

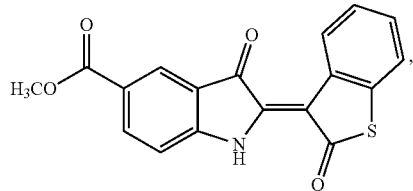

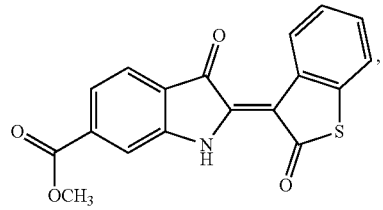

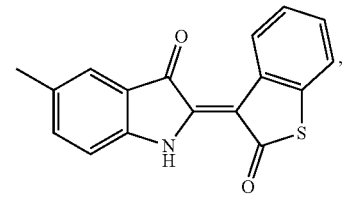

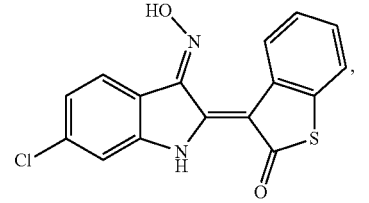

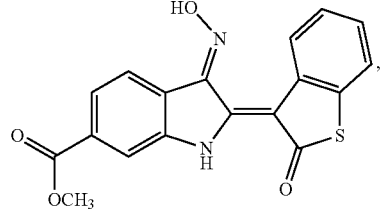

-continued

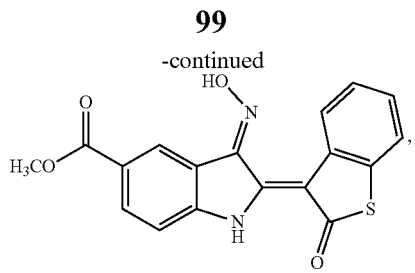

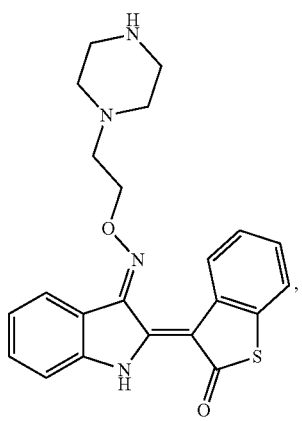

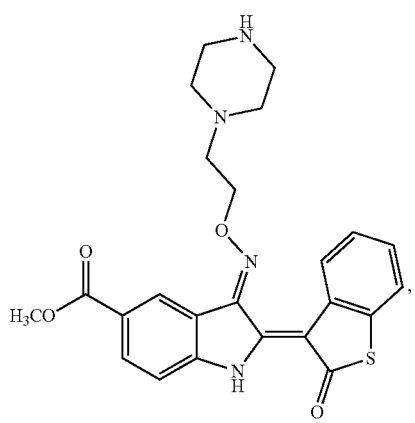

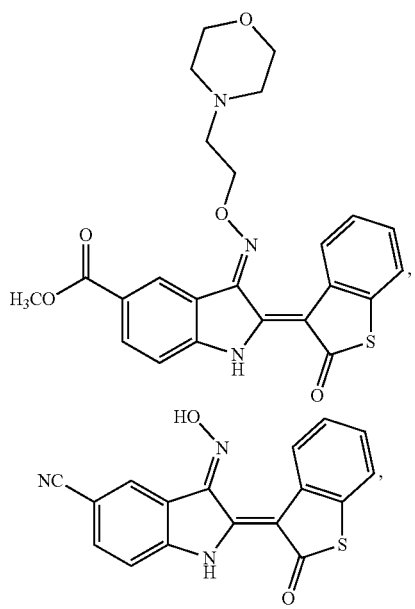

-continued

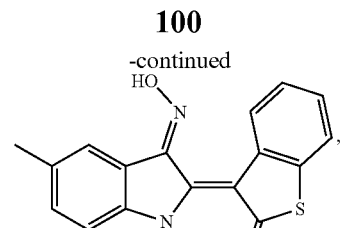

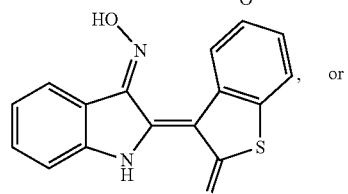

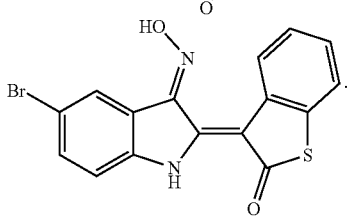

Embodiment Q29

A pharmaceutical composition comprising a pharmaceutically acceptable excipient and a compound, or pharmaceutically acceptable salt thereof, having structural Formula (I):

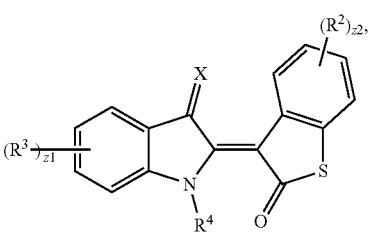

wherein:
n1, n2, n3 and n4 are independently an integer from 0 to 4;
m2, m3, v1, v2, v3 and v4 are independently 1 or 2;
z1 and z2 are independently an integer from 0 to 4;
X is =O, =S or =NR';
$R^1$ is hydrogen, halogen, —$CX^1_3$, —$CHX^1_2$, —$CH_2X^1$, —$N_3$, —CN, —$SO_nR^{1A}$, —$SO_{v1}NR^{1B}R^{1C}$, —$NR^{1B}R^{1C}$, —$C(O)R^{1D}$, —$C(O)OR^{1D}$, —$C(O)NR^{1B}R^{1C}$, —$OR^{1A}$, —$OCX^1_3$, —$OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^2$ is independently hydrogen, halogen, —$CX^2_3$, —$CHX^2_2$, —$CH_2X^2$, —$N_3$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^2_3$, —$OCHX^2_2$, —$OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^3{}_3$, $-CHX^3{}_2$, $-CH_2X^3$, $-N_3$, $-CN$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^3{}_3$, $-OCHX^3{}_2$, $-OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, $-CX^4{}_3$, $-CHX^4{}_2$, $-CH_2X^4$, $-CN$, $-SO_{n4}R^{4A}$, $-SO_{v4}NR^{4B}R^{4C}$, $-NR^{4B}R^{4C}$, $-C(O)R^{4D}$, $-C(O)OR^{4D}$, $-C(O)NR^{4B}R^{4C}$, $-OR^{4A}$, $-OCX^4{}_3$, $-OCHX^4{}_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, $-CF_3$, $-CCl_3$, $-CBr_3$, $-C_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently $-Cl$, $-Br$, $-I$ or $-F$.

Embodiment Q30

The pharmaceutical composition of Embodiment Q29, wherein the compound has structural Formula (I-B):

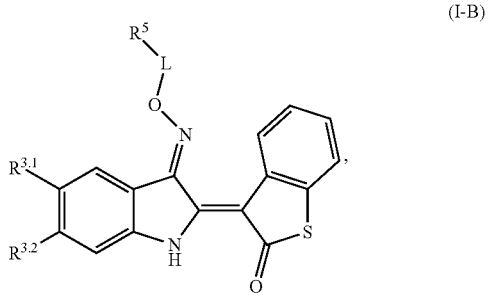

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^{3.1}$ is hydrogen, halogen, $-CX^{3.1}{}_3$, $-CHX^{3.1}{}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}{}_3$, $-OCHX^{3.1}{}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}{}_3$, $-CHX^{3.2}{}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}{}_3$, $-OCHX^{3.2}{}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, $-CX^5{}_3$, $-CHX^5{}_2$, $-CH_2X^5$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^5{}_3$, $-OCHX^5{}_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, $-CF_3$, $-CCl_3$, $-CBr_3$, $-C_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently $-Cl$, $-Br$, $-I$ or $-F$.

Embodiment Q31

The pharmaceutical composition of Embodiments Q29-Q30, wherein the compound is:

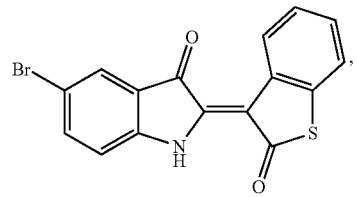

103
-continued
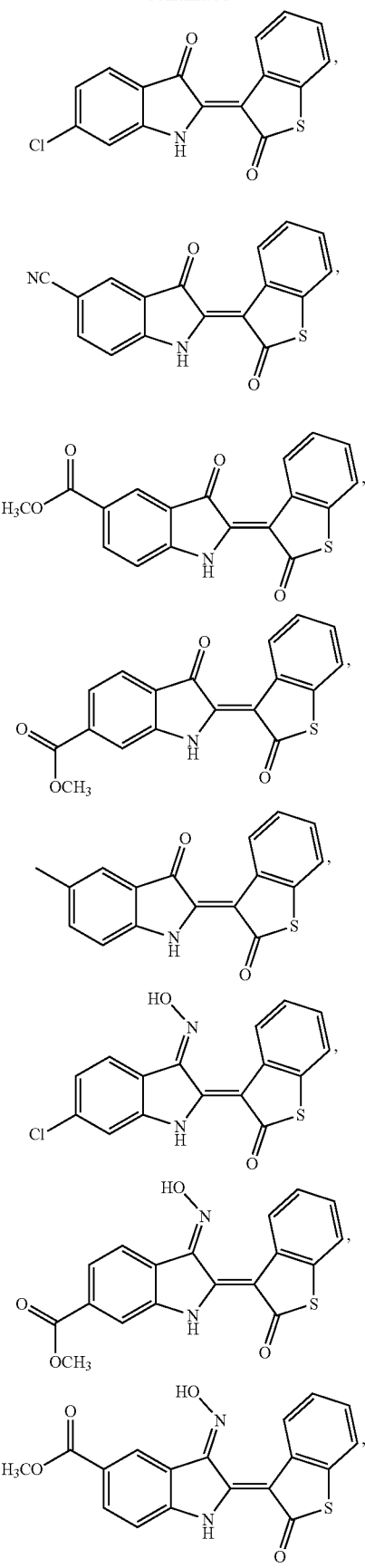
104
-continued
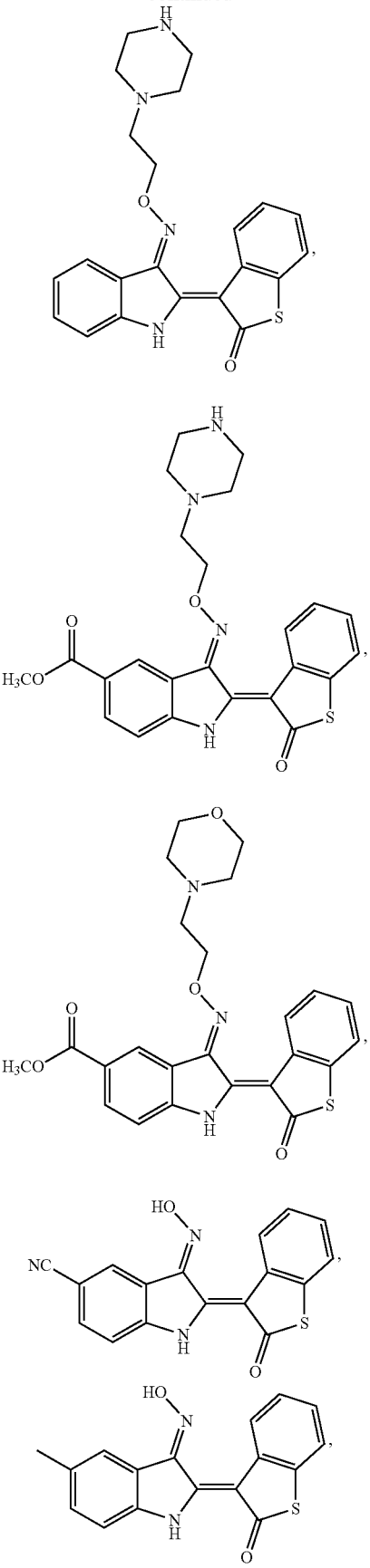

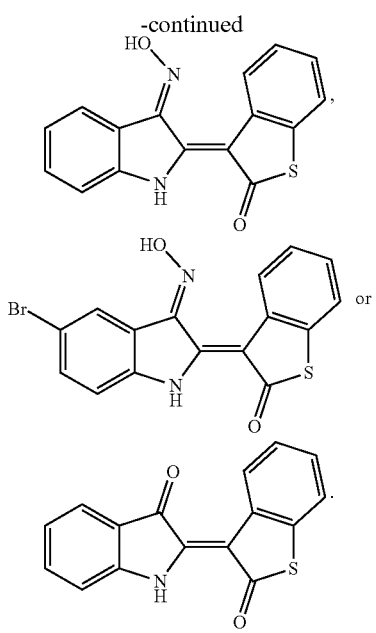

Embodiment Q32

A pharmaceutical composition comprising a compound of any one of Embodiments Q1-Q28.

Embodiment Q33

A method of treating cancer, comprising administering to a subject in need thereof a therapeutically effective amount of a compound, or pharmaceutically acceptable salt thereof, having structural Formula (I):

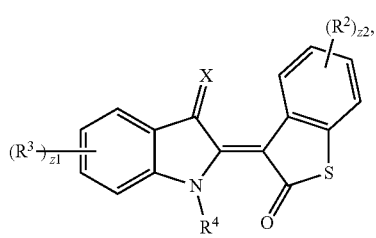

wherein:
n1, n2, n3 and n4 are independently an integer from 0 to 4;
m2, m3, m5, v1, v2, v3 and v4 are independently 1 or 2;
z1 and z2 are independently an integer from 0 to 4;
X is =O, =S or =NR$^1$;
R$^1$ is hydrogen, halogen, —CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^4$ is hydrogen, halogen, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$ and R$^{4B}$ and R$^{4C}$ substituents bonded to the same nitrogen atom may optionally be joined to form a substituted or unsubstituted heterocycloalkyl or substituted or unsubstituted heteroaryl; and
X$^1$, X$^2$, X$^3$ and X$^4$ are independently —Cl, —Br, —I or —F.

Embodiment Q34

The method of Embodiment Q33, wherein the compound has structural Formula (I-B):

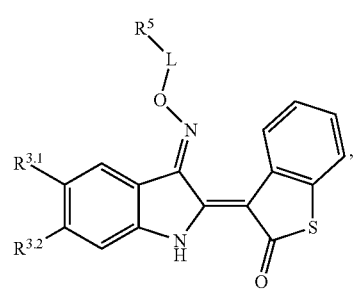

wherein:

n3.1, n3.2 and n5 are independently an integer from 0 to 4;

m3.1, m3.2, m5, v3.1, v3.2 and v5 are independently 1 or 2;

L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^{3.1}$ is hydrogen, halogen, —$CX^{3.1}_3$, —$CHX^{3.1}_2$, —$CH_2X^{3.1}$, —$N_3$, —CN, —$SO_{n3.1}R^{3.1A}$, —$SO_{v3.1}NR^{3.1B}R^{3.1C}$, —$NHNR^{3.1B}R^{3.1C}$, —$ONR^{3.1B}R^{3.1C}$, —$NHC(O)NHNR^{3.1B}R^{3.1C}$, —$NHC(O)NR^{3.1B}R^{3.1C}$, —$N(O)_{m3.1}$, —$NR^{3.1B}R^{3.1C}$, —$C(O)R^{3.1D}$, —$C(O)OR^{3.1D}$, —$C(O)NR^{3.1B}R^{3.1C}$, —$OR^{3.1A}$, —$NR^{3.1B}SO_2R^{3.1A}$, —$NR^{3.1B}C(O)R^{3.1D}$, —$NR^{3.1B}C(O)OR^{3.1D}$, —$NR^{3.1B}OR^{3.1D}$, —$OCX^{3.1}_3$, —$OCHX^{3.1}_2$, —$OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, —$CX^{3.2}_3$, —$CHX^{3.2}_2$, —$CH_2X^{3.2}$, —$N_3$, —CN, —$SO_{n3.2}R^{3.2A}$, —$SO_{v3.2}NR^{3.2B}R^{3.2C}$, —$NHNR^{3.2B}R^{3.2C}$, —$ONR^{3.2B}R^{3.2C}$, —$NHC(O)NHNR^{3.2B}R^{3.2C}$, —$NHC(O)NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}_3$, —$OCHX^{3.2}_2$, —$OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, —$CX^5_3$, —$CHX^5_2$, —$CH_2X^5$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^5_3$, —$OCHX^5_2$, —$OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently —Cl, —Br, —I or —F.

Embodiment Q35

The method of any one of Embodiments Q33-Q34, wherein the cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer or prostate cancer.

Embodiment Q36

The method of any one of Embodiments Q33-Q35, wherein the cancer is a solid tumor or a blood tumor.

Embodiment Q37

The method of any of Embodiments Q33-Q36, wherein the compound is co-administered with an effective amount of an anti-cancer agent.

Embodiment Q38

A method of modulating a kinase, comprising contacting the kinase with a compound, or pharmaceutically acceptable salt thereof, having structural Formula (I):

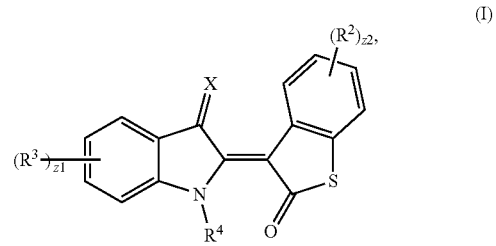

wherein:

n1, n2, n3 and n4 are independently an integer from 0 to 4;

m2, m3, v1, v2, v3 and v4 are independently 1 or 2;

z1 and z2 are independently an integer from 0 to 4;

X is =O, =S or =$NR^1$;

$R^1$ is hydrogen, halogen, —$CX^1_3$, —$CHX^1_2$, —$CH_2X^1$, —$N_3$, —CN, —$SO_nR^{1A}$, —$SO_{v1}NR^{1B}R^{1C}$, —$NR^{1B}R^{1C}$, —$C(O)R^{1D}$, —$C(O)OR^{1D}$, —$C(O)NR^{1B}R^{1C}$, —$OR^{1A}$, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^2$ is independently hydrogen, halogen, —$CX^2_3$, —$CHX^2_2$, —$CH_2X^2$, —$N_3$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^2_3$, —$OCHX^2_2$, —$OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^3_3$, —$CHX^3_2$, —$CH_2X^3$, —$N_3$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^3_3$, —$OCHX^3_2$, —$OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4_3$, —OCHX4$_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^B$ and $R^C$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently —Cl, —Br, —I or —F.

Embodiment Q39

The method of Embodiment Q38, wherein the compound has structural Formula (I-B):

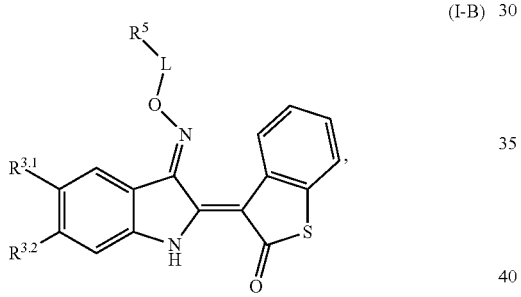

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^{3.1}$ is hydrogen, halogen, —CX$^{1.3}_3$, —CHX$^{3.1}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}_3$, —OCHX$^{3.1}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, —CX$^{3.2}_3$, —CHX$^{3.2}_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$_{2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2}$OR$^{3.2D}$, OCX$^{3.2}_3$, —OCHX$^{3.2}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^5$ is hydrogen, halogen, —CX$^5_3$, —CHX$^{52}$, —CH$_2$X$^5$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^5_3$, —OCHX$^{52}$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{32B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and
$X^{3.1}$, $X^{3.2}$ and $X^5$ are independently —Cl, —Br, —I or —F.

Embodiment Q40

The method of anyone of Embodiments Q38-Q39, wherein the kinase is JAK, JAK2, TYK2, Src, c-Src, ABL1, ABL1 T315I, an Aurora kinase, GSK-3b or a CDK.

Embodiment Q41

The method of Embodiment Q40, wherein the Aurora kinase is Aurora A.

Embodiment Q42

A method of modulating STAT or STAT3, comprising contacting STAT or STAT3 with a compound, or pharmaceutically acceptable salt thereof, having structural Formula (I):

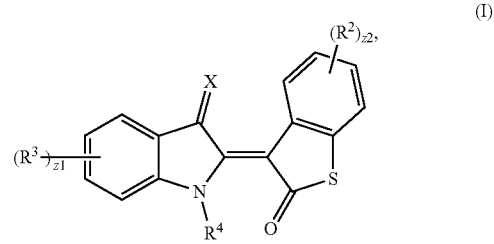

(I)

wherein:
n1, n2, n3 and n4 are independently an integer from 0 to 4;
m2, m3, v1, v2, v3 and v4 are independently 1 or 2;

z1 and z2 are independently an integer from 0 to 4;

X is =O, =S or =NR';

$R^1$ is hydrogen, halogen, $-CX^1_3$, $-CHX^1_2$, $-CH_2X^1$, $-N_3$, $-CN$, $-SO_{n1}R^{1A}$, $-SO_{v1}NR^{1B}R^{1C}$, $-NR^{1B}R^{1C}$, $-C(O)R^{1D}$, $-C(O)OR^{1D}$, $-C(O)NR^{1B}R^{1C}$, $-OR^{1A}$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^2$ is independently hydrogen, halogen, $-CX^2_3$, $-CHX^2_2$, $-CH_2X^2$, $-N_3$, $-CN$, $-SO_{n2}R^{2A}$, $-SO_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^2_3$, $-OCHX^2_2$, $-OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^3_3$, $-CHX^3_2$, $-CH_2X^3$, $-N_3$, $-CN$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^3_3$, $-OCHX3_2$, $-OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, $-CX^4_3$, $-CHX^4_2$, $-CH_2X^4$, $-CN$, $-SO_{n4}R^{4A}$, $-SO_{v4}NR^{4B}R^{4C}$, $-NR^{4B}R^{4C}$, $-C(O)R^{4D}$, $-C(O)OR^{4D}$, $-C(O)NR^{4B}R^{4C}$, $-OR^{4A}$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, $-CF_3$, $-CCl_3$, $-CBr_3$, $-C_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently $-Cl$, $-Br$, $-I$ or $-F$.

Embodiment Q43

The method of Embodiment Q42, wherein the compound has structural Formula (I-B):

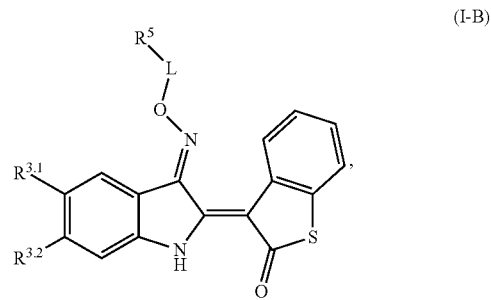

(I-B)

wherein:

n3.1, n3.2 and n5 are independently an integer from 0 to 4;

m3.1, m3.2, m5, v3.1, v3.2 and v5 are independently 1 or 2;

L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^{3.1}$ is hydrogen, halogen, $-CX^{1.3}$, $-CHX^{3.1}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, $-CX^5_3$, $-CHX^5_2$, $-CH_2X^5$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently —Cl, —Br, —I or —F.

Embodiment Q44

The method of any of Embodiments Q33-Q43, wherein the compound is:

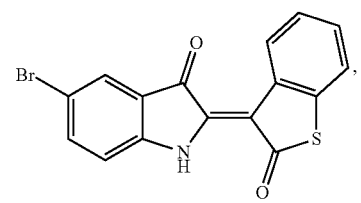

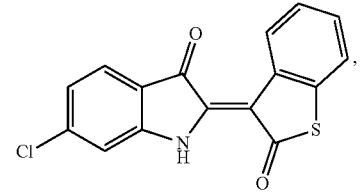

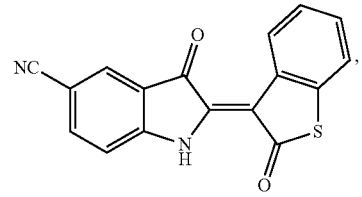

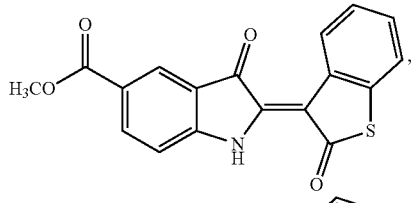

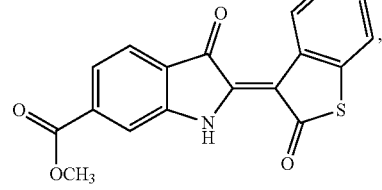

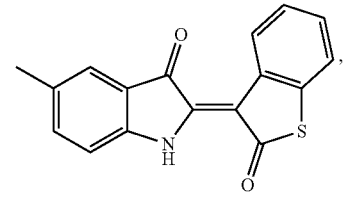

-continued

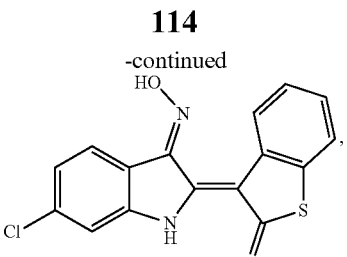

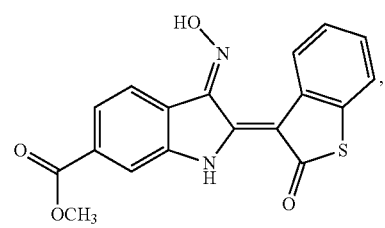

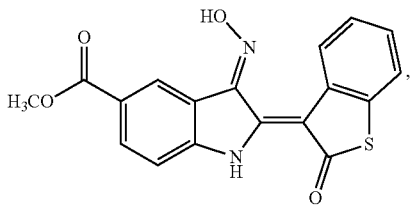

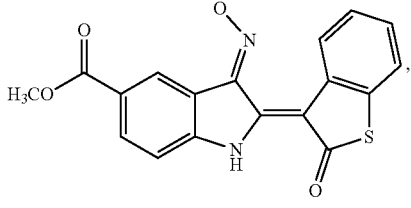

115
-continued

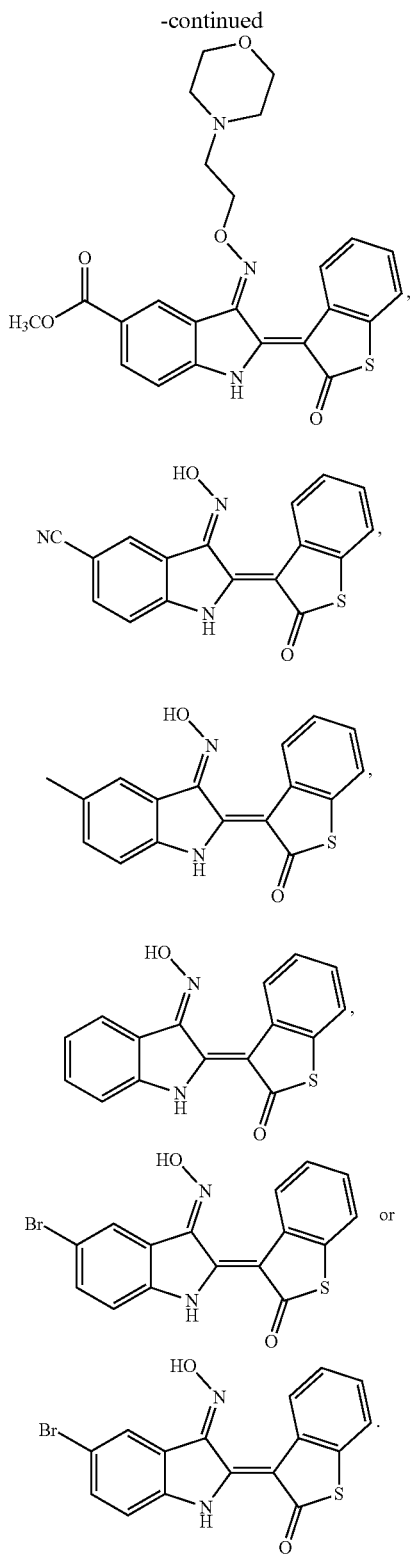

Embodiments Q45

The method of any of Embodiments Q33-Q44, wherein the compound is in a pharmaceutical composition comprising a pharmaceutically acceptable excipient.

116
EMBODIMENTS

Embodiment 1

A compound, or pharmaceutically acceptable salt thereof, having structural Formula (I):

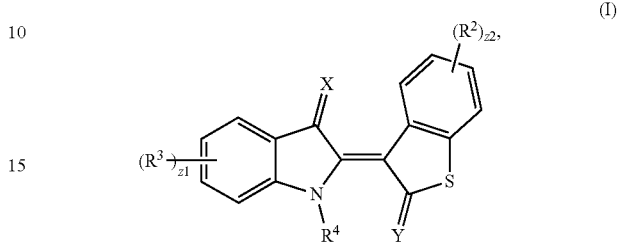

wherein:
n1, n2, n3, n4 and n6 are independently an integer from 0 to 4;
m2, m3, v1, v2, v3, v4 and v6 are independently 1 or 2;
z1 and z2 are independently an integer from 1 to 4;
X is =O, =S or =NR$^1$;
Y is =O, =S or =NR$^6$.
R$^1$ is hydrogen, halogen, oxo, —CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^3$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^4$ is hydrogen, halogen, oxo, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, OR$^{4A}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is hydrogen, halogen, oxo, $-CX^6_3$, $-CHX^6_2$, $-CH_2X^6$, $-N_3$, $-CN$, $-SO_6R^{6A}$, $-SO_6NR^{6B}R^{6C}$, $-NR^{6B}R^{6C}$, $-C(O)R^{6D}$, $-C(O)OR^{6D}$, $-C(O)NR^{6B}R^{6C}$, $-OR^{6A}$, $-OCX^6_3$, $-OCHX^6_2$, $-OCH_2X^6$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$ and $R^{6D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$ and $R^{6B}$ and $R^{6C}$ substituents bonded to the same nitrogen atom may optionally be joined to form a substituted or unsubstituted heterocycloalkyl or substituted or unsubstituted heteroaryl; and $X^1$, $X^2$, $X^3$, $X^4$ and $X^6$ are independently $-Cl$, $-Br$, $-I$ or $-F$, provided that when X is $=O$ and Y is $=O$, then at least one of $R^2$, $R^3$ and $R^4$ is not hydrogen.

Embodiment 2

The compound of Embodiment 1, wherein $R^2$ is hydrogen.

Embodiment 3

The compound of Embodiment 1 or 2, wherein $R^4$ is hydrogen or substituted or unsubstituted alkyl.

Embodiment 4

The compound of any one of Embodiments 1-3, wherein X is $=O$.

Embodiment 5

The compound of any one of Embodiments 1-4, wherein the compound has structural Formula (I-A):

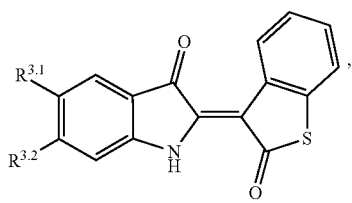

(I-A)

wherein:
n3.1 and n3.2 are independently an integer from 0 to 4;
m3.1, m3.2, v3.1 and v3.2 are independently 1 or 2;
$R^{3.1}$ is hydrogen, halogen, $-CX^{3.1}_3$, $-CHX^{3.1}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$ and $R^{3.2B}$ and $R^{3.2C}$, substituents bonded to the same nitrogen atom may optionally be joined to form a substituted or unsubstituted heterocycloalkyl or substituted or unsubstituted heteroaryl; and $X^{3.1}$ and $X^{3.2}$ are independently $-Cl$, $-Br$, $-I$ or $-F$.

The compound of any one of Embodiments 1-3, wherein X is $=NR^1$.

The compound of any one of Embodiments 1-3 and 6, wherein $R^1$ is $-OH$.

The compound of any one of Embodiments 1-3 and 6, or a pharmaceutically acceptable salt thereof, wherein the compound has structural Formula (I-B):

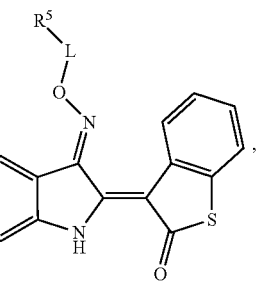

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^{3.1}$ is hydrogen, halogen, $-CX^{3.1}_3$, $-CHX^{3.1}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, $-CX^5_3$, $-CHX^5_2$, $-CH_2X^5$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, $-CF_3$, $-CCl_3$, $-CBr_3$, $-C_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently $-Cl$, $-Br$, $-I$ or $-F$.

Embodiment 9

The compound of Embodiment 5 or 8, wherein $R^{3.1}$ and $R^{3.2}$ are independently hydrogen, halogen, $-CN$, substituted or unsubstituted alkyl or substituted or unsubstituted heteroalkyl.

Embodiment 10

The compound of Embodiment 8, wherein L is unsubstituted alkylene.

Embodiment 11

The compound of Embodiment 8, wherein L is unsubstituted $C_1$-$C_8$ alkylene.

Embodiment 12

The compound of Embodiment 8, wherein L is unsubstituted $C_1$-$C_4$ alkylene.

Embodiment 13

The compound of Embodiment 8, wherein L is unsubstituted ethylene.

Embodiment 14

The compound of Embodiment 8, wherein L is a bond.

Embodiment 15

The compound of Embodiment 8, wherein $R^5$ is hydrogen, halogen, $-CX^5_3$, $-OCX^5_3$, $-CN$, $-OH$, $-NH_2$, $-COOH$, $-C(O)OR^{5D}$, $-CONH_2$, $-NO_2$, SH, $-NHNH_2$, $-NR^{5B}R^{5C}$, $-OR^{5A}$, $-SR^A$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 16

The compound of Embodiment 14, wherein $R^5$ is hydrogen.

Embodiment 17

The compound of Embodiment 16, wherein $R^{3.1}$ or $R^{3.2}$ is $-Cl$, $-Br$, $-I$ or $-F$.

Embodiment 18

The compound of Embodiment 8, wherein $R^5$ is $-NR^{5B}R^{5C}$.

Embodiment 19

The compound of Embodiment 18, wherein $R^{5B}$ and $R^{5C}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 20

The compound of Embodiment 19, wherein $R^{5B}$ and $R^{5C}$ are independently substituted or unsubstituted alkyl.

Embodiment 21

The compound of Embodiment 20, wherein $R^{5B}$ and $R^{5C}$ are independently substituted or unsubstituted $C_1$-$C_8$ alkyl.

Embodiment 22

The compound of Embodiment 21, wherein $R^{5B}$ and $R^{5C}$ are independently substituted or unsubstituted $C_1$-$C_4$ alkyl.

Embodiment 23

The compound of Embodiment 2₂, wherein $R^{5B}$ and $R^{5C}$ are independently unsubstituted $C_1$-$C_4$ alkyl.

Embodiment 24

The compound of Embodiment 8, wherein $R^{5B}$ and $R^C$ are joined together to form a substituted or unsubstituted heterocycloalkyl or substituted or unsubstituted heteroaryl.

Embodiment 25

The compound of Embodiment 24, wherein $R^{5B}$ and $R^{5C}$ are joined together to form a substituted or unsubstituted heterocycloalkyl.

Embodiment 26

The compound of Embodiment 25, wherein $R^{5B}$ and $R^{5C}$ are joined together to form a substituted or unsubstituted $C_5$-$C_7$ heterocycloalkyl.

Embodiment 27

The compound of Embodiment 26, wherein $R^{5B}$ and $R^{5C}$ are joined together to form a substituted $C_5$-$C_7$ heterocycloalkyl.

Embodiment 28

The compound of Embodiment 27, wherein $R^{5B}$ and $R^{5C}$ are joined together to form a substituted or unsubstituted pyrrolidinyl.

Embodiment 29

The compound of Embodiment 27, wherein $R^{5B}$ and $R^{5C}$ are joined together to form a substituted or unsubstituted piperazinyl.

Embodiment 30

The compound of Embodiment 27, wherein $R^{5B}$ and $R^{5C}$ are joined together to form a substituted or unsubstituted morpholinyl

Embodiment 31

The compound of Embodiment 29, wherein the compound has structural formula (IV-A) or (IV-B):

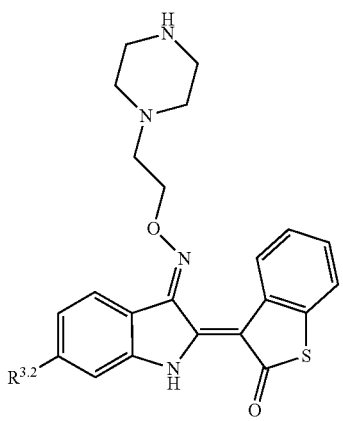

(IV-A)

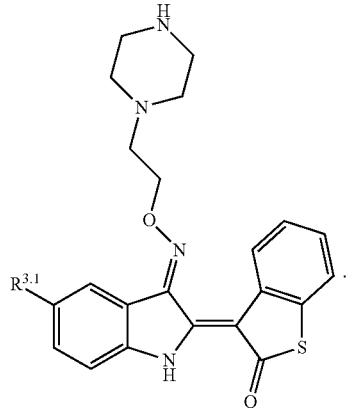

(IV-B)

Embodiment 32

The compound of Embodiment 31, wherein each $R^{3.1}$ and $R^{3.2}$ is independently —C(O)H, —C(O)CH₃, C(O)OH, or —C(O)OCH₃.

Embodiment 33

The compound of anyone of Embodiments 1-32, wherein the compound is:

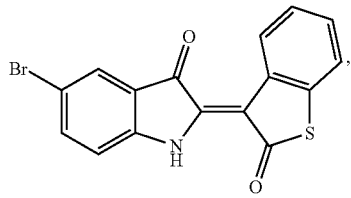

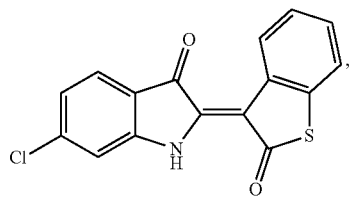

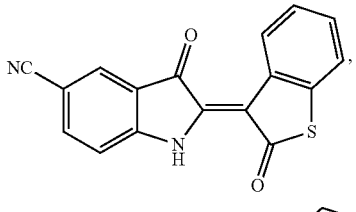

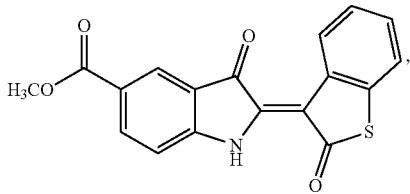

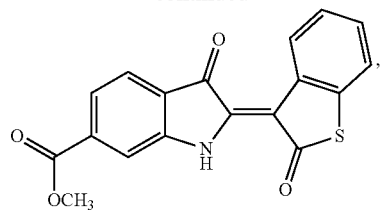
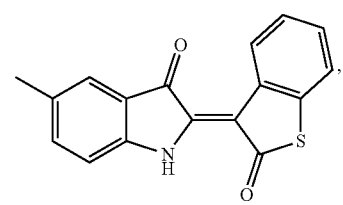
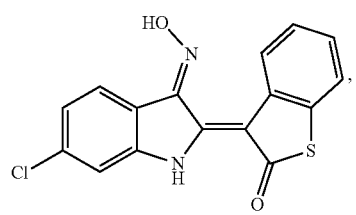
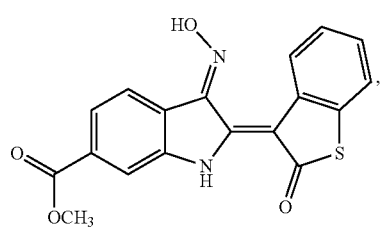
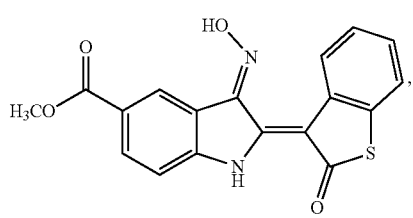
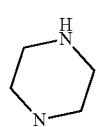
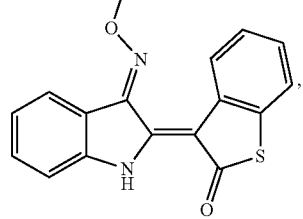
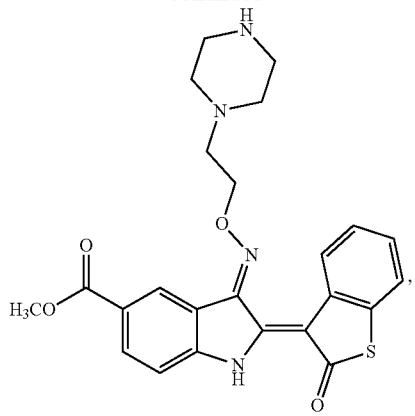
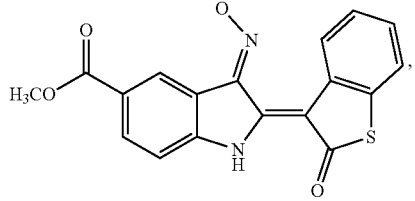
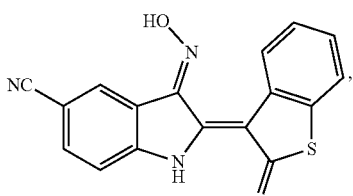
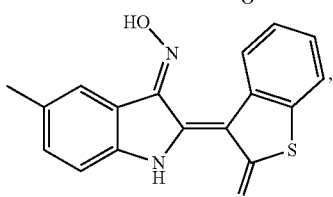
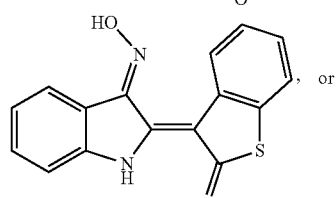, or
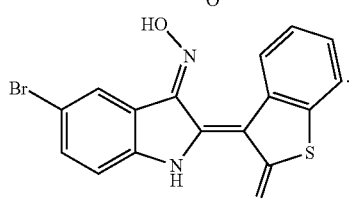

Embodiment 34

A pharmaceutical composition comprising a pharmaceutically acceptable excipient and a compound, or pharmaceutically acceptable salt thereof, having structural Formula (I):

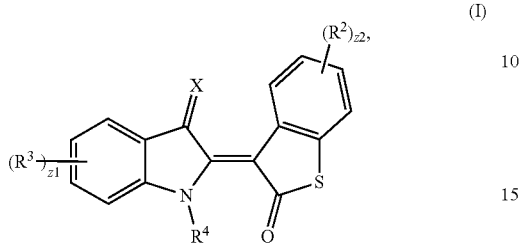

wherein:

n1, n2, n3 and n4 are independently an integer from 0 to 4;

m2, m3, v1, v2, v3 and v4 are independently 1 or 2;

z1 and z2 are independently an integer from 1 to 4;

X is =O, =S or =NR$^1$;

R$^1$ is hydrogen, halogen, —CX$^1_3$, —CHX$^1_2$, —CH$_2$X$^1$, —N$_3$, —CN, —SO$_n$1R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^4$ is hydrogen, halogen, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$ and R$^{4B}$ and R$^{4C}$ substituents bonded to the same nitrogen atom may optionally be joined to form a substituted or unsubstituted heterocycloalkyl or substituted or unsubstituted heteroaryl; and X$^1$, X$^2$, X$^3$ and X$^4$ are independently —Cl, —Br, —I or —F.

Embodiment 35

The pharmaceutical composition of Embodiment 34, wherein R$^2$ is hydrogen.

Embodiment 36

The pharmaceutical composition of Embodiment 34 or 35, wherein R$^4$ is hydrogen or substituted or unsubstituted alkyl.

Embodiment 37

The pharmaceutical composition of any one of Embodiments 34-36, wherein X is =O.

Embodiment 38

The pharmaceutical composition of any one of Embodiments 34-37 wherein the compound has structural Formula (I-A):

wherein:

n3.1 and n3.2 are independently an integer from 0 to 4;

m3.1, m3.2, v3.1 and v3.2 are independently 1 or 2;

R$^{3.1}$ is hydrogen, halogen, —CX$^{3.1}_3$, —CHX$^{3.1}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}_3$, —OCHX$^{3.1}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{3.2}$ is hydrogen, halogen, —CX$^{3.2}_3$, —CHX$^{3.2}_2$, —CH$_2$X$^{3.2}$, —N$_3$, —CN, —SO$_{n3.2}$R$^{3.2A}$, —$SO_{v3.2}NR^{3.2B}R^{3.2C}$, —$NHNR^{3.2B}R^{3.2C}$, —$ONR^{3.2B}R^{3.2C}$, —$NHC(O)NHNR^{3.2B}R^{3.2C}$, —$NHC(O)NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}_3$, —$OCHX^{3.2}_2$, —$OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$ and $R^{3.2B}$ and $R^{3.2C}$ substituents bonded to the same nitrogen atom may optionally be joined to form a substituted or unsubstituted heterocycloalkyl or substituted or unsubstituted heteroaryl; and $X^{3.1}$ and $X^{3.2}$ are independently —Cl, —Br, —I or —F.

Embodiment 39

The pharmaceutical composition of any one of Embodiments 34-36, wherein X is =$NR^1$.

Embodiment 40

The pharmaceutical composition of any one of Embodiments 34-36 and 39, wherein $R^1$ is —OH.

Embodiment 41

The pharmaceutical composition of Embodiment 34, wherein the compound has structural Formula (I-B):

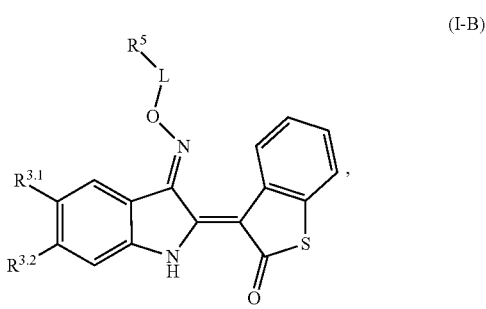

(I-B)

n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^{3.1}$ is hydrogen, halogen, —$CX^{3.1}_3$, —$CHX^{3.1}_2$, —$CH_2X^{3.1}$, —$N_3$, —CN, —$SO_{n3.1}R^{3.1A}$, —$SO_{v3.1}NR^{3.1B}R^{3.1C}$, —$NHNR^{3.1B}R^{3.1C}$, —$ONR^{3.1B}R^{3.1C}$, —$NHC(O)NHNR^{3.1B}R^{3.1C}$, —$NHC(O)NR^{3.1B}R^{3.1C}$, —$N(O)_{m3.1}$, —$NR^{3.1B}R^{3.1C}$, —$C(O)R^{3.1D}$, —$C(O)OR^{3.1D}$, —$C(O)NR^{3.1B}R^{3.1C}$, —$OR^{3.1A}$, —$NR^{3.1B}SO_2R^{3.1A}$, —$NR^{3.1B}C(O)R^{3.1D}$, —$NR^{3.1B}C(O)OR^{3.1D}$, —$NR^{3.1B}OR^{3.1D}$, —$OCX^{3.1}_3$, —$OCHX^{3.1}_2$, —$OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, —$CX^{3.2}_3$, —$CHX^{3.2}_2$, —$CH_2X^{3.2}$, —$N_3$, —CN, —$SO_{n3.2}R^{3.2A}$, —$SO_{v3.2}NR^{3.2B}R^{3.2C}$, —$NHNR^{3.2B}R^{3.2C}$, —$ONR^{3.2B}R^{3.2C}$, —$NHC(O)NHNR^{3.2B}R^{3.2C}$, —$NHC(O)NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}_3$, —$OCHX^{3.2}_2$, —$OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, —$CX^5_3$, —$CHX^5_2$, —$CH_2X^5$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^5_3$, —$OCHX^5_2$, —$OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently —Cl, —Br, —I or —F.

Embodiment 42

The pharmaceutical composition of Embodiment 41, wherein $R^{3.1}$ and $R^{3.2}$ are independently hydrogen, halogen, —CN, substituted or unsubstituted alkyl or substituted or unsubstituted heteroalkyl.

Embodiment 43

The pharmaceutical composition of Embodiment 41, wherein L is unsubstituted alkylene.

Embodiment 44

The pharmaceutical composition of Embodiment 41, wherein L is unsubstituted $C_1$-$C_8$ alkylene.

Embodiment 45

The pharmaceutical composition of Embodiment 41, wherein L is unsubstituted $C_1$-$C_4$ alkylene.

Embodiment 46

The pharmaceutical composition of Embodiment 41, wherein L is unsubstituted ethylene.

Embodiment 47

The pharmaceutical composition of Embodiment 41, wherein L is a bond.

Embodiment 48

The pharmaceutical composition of Embodiment 41, wherein $R^5$ is hydrogen, halogen, —$CX^5_3$, —$OCX^5_3$, —CN, —OH, —$NH_2$, —COOH, —C(O)$OR^{5D}$, —$CONH_2$, —$NO_2$, SH, —$NHNH_2$, —$NR^{5B}R^{5C}$, —$OR^{5A}$, —$SR^A$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 49

The pharmaceutical composition of Embodiment 47, wherein $R^5$ is hydrogen.

Embodiment 50

The pharmaceutical composition of Embodiment 49, wherein $R^{3.1}$ or $R^{3.2}$ is —Cl, —Br, —I or —F.

Embodiment 51

The pharmaceutical composition of Embodiment 41, wherein $R^5$ is —$NR^{5B}R^{5C}$.

Embodiment 52

The pharmaceutical composition of Embodiment 51, wherein $R^{5B}$ and $R^{5C}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 53

The pharmaceutical composition of Embodiment 52, wherein $R^{5B}$ and $R^{5C}$ are independently substituted or unsubstituted alkyl.

Embodiment 54

The pharmaceutical composition of Embodiment 52, wherein $R^{5B}$ and $R^{5C}$ are independently substituted or unsubstituted $C_1$-$C_8$ alkyl.

Embodiment 55

The pharmaceutical composition of Embodiment 52, wherein $R^{5B}$ and $R^{5C}$ are independently substituted or unsubstituted $C_1$-$C_4$ alkyl.

Embodiment 56

The pharmaceutical composition of Embodiment 52, wherein $R^{5B}$ and $R^{5C}$ are independently unsubstituted $C_1$-$C_4$ alkyl.

Embodiment 57

The pharmaceutical composition of Embodiment 51, wherein $R^{5B}$ and $R^{5C}$ are joined together to form a substituted or unsubstituted heterocycloalkyl or substituted or unsubstituted heteroaryl.

Embodiment 58

The pharmaceutical composition of Embodiment 57, wherein $R^{5B}$ and $R^{5C}$ are joined together to form a substituted or unsubstituted heterocycloalkyl.

Embodiment 59

The pharmaceutical composition of Embodiment 58, wherein $R^{5B}$ and $R^{5C}$ are joined together to form a substituted or unsubstituted $C_5$-$C_7$ heterocycloalkyl.

Embodiment 60

The pharmaceutical composition of Embodiment 59, wherein $R^{5B}$ and $R^{5C}$ are joined together to form a substituted $C_5$-$C_7$ heterocycloalkyl.

Embodiment 61

The pharmaceutical composition of Embodiment 60, wherein $R^{5B}$ and $R^{5C}$ are joined together to form a substituted or unsubstituted pyrrolidinyl.

Embodiment 62

The pharmaceutical composition of Embodiment 60, wherein $R^{5B}$ and $R^{5C}$ are joined together to form a substituted or unsubstituted piperazinyl.

Embodiment 63

The pharmaceutical composition of Embodiment 60, wherein $R^{5B}$ and $R^{5C}$ are joined together to form a substituted or unsubstituted morphorinyl.

Embodiment 64

The pharmaceutical composition of Embodiment 62, wherein the compound has structural formula (IV-A) or (IV-B):

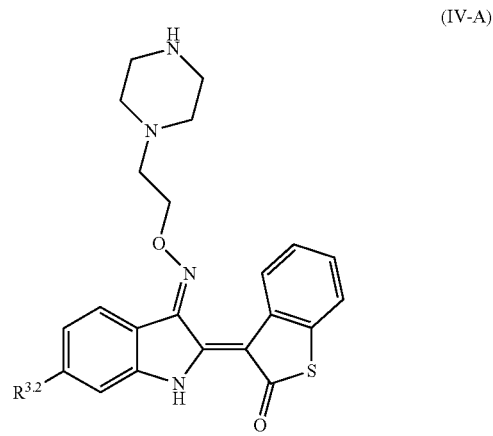

(IV-A)

-continued
(IV-B)
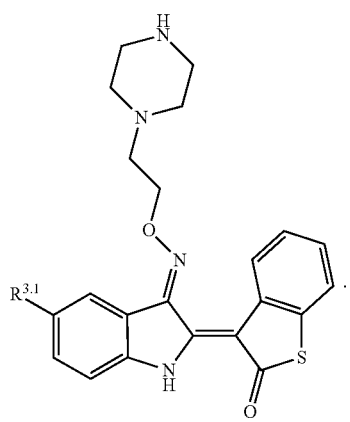
Embodiment 65
The pharmaceutical composition of Embodiment 64, wherein each $R^{3.1}$ and $R^{3.2}$ is independently —C(O)H, —C(O)CH$_3$, C(O)OH, or —C(O)OCH$_3$.
Embodiment 66
The pharmaceutical composition of Embodiment 34-65, wherein the compound is:
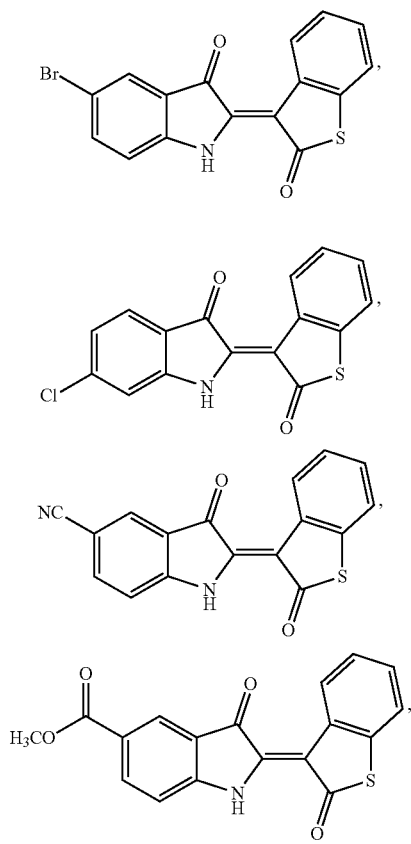
-continued
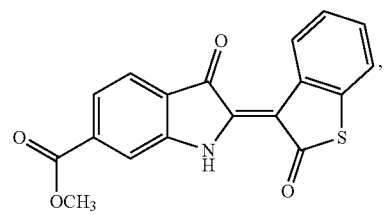
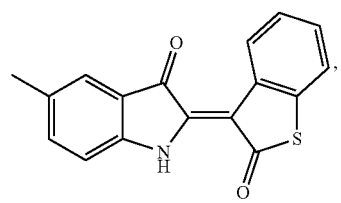
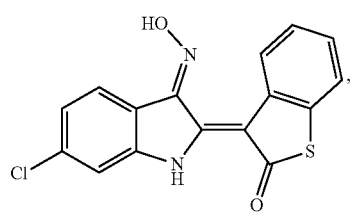
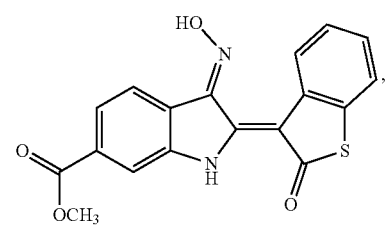
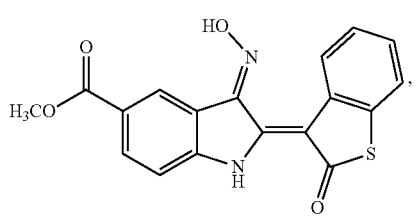
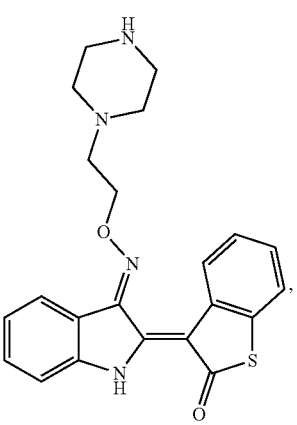

133
-continued

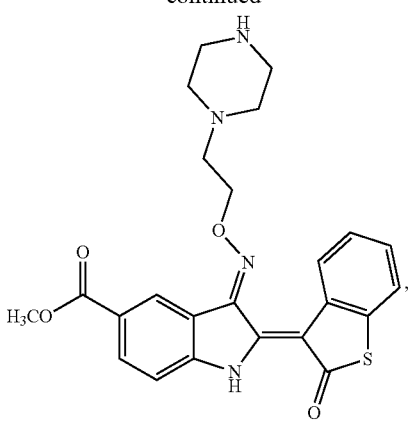

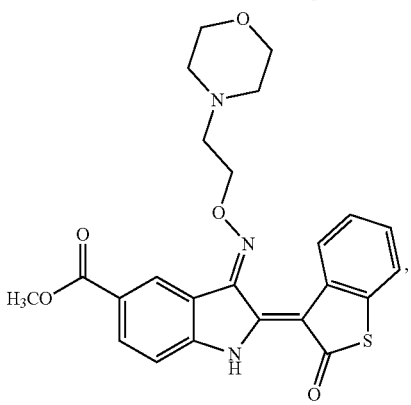

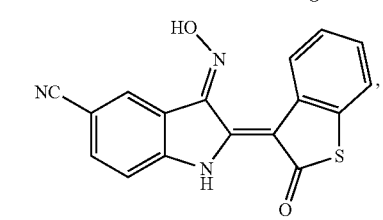

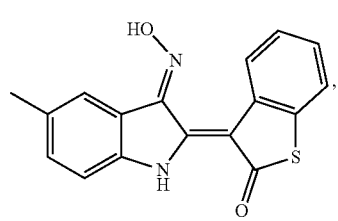

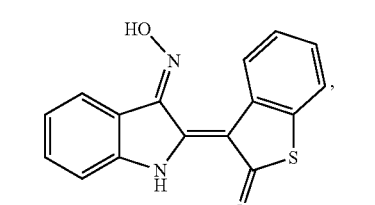

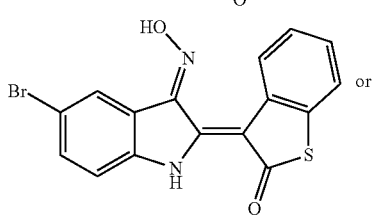 or

134
-continued

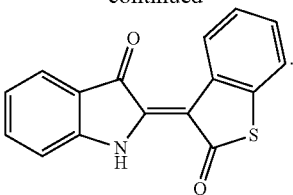

Embodiment 67

A pharmaceutical composition comprising a compound of any one of Embodiments 1-33.

Embodiment 68

A method of treating cancer, comprising administering to a subject in need thereof a therapeutically effective amount of a compound, or pharmaceutically acceptable salt thereof, having structural Formula (I):

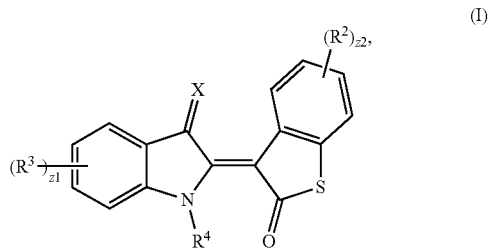

wherein:
n1, n2, n3 and n4 are independently an integer from 0 to 4;
m2, m3, m5, v1, v2, v3 and v4 are independently 1 or 2;
z1 and z2 are independently an integer from 1 to 4;
X is =O, =S or =NR';
$R^1$ is hydrogen, halogen, —$CX^1_3$, —$CHX^1_2$, —$CH_2X^1$, —$N_3$, —CN, —$SO_{n1}R^{1A}$, —$SO_{v1}NR^{1B}R^{1C}$, —$NR^{1B}R^{1C}$, —$C(O)R^{1D}$, —$C(O)OR^{1D}$, —$C(O)NR^{1B}R^{1C}$, —$OR^{1A}$, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^2$ is independently hydrogen, halogen, —$CX^2_3$, —$CHX^2_2$, —$CH_2X^2$, —$N_3$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^2_3$, —$OCHX^2_2$, —$OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, —$CX^3_3$, —$CHX^3_2$, —$CH_2X^3$, —$N_3$, —CN, —$SO_3R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3{}_3$, —OCHX$^3{}_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^4$ is hydrogen, halogen, —CX$^4{}_3$, —CHX$^4{}_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, OR$^{4A}$, —OCX$^4{}_3$, —OCHX$^4{}_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{1A}$, R$^{1B}$, R$^{1C}$, R$^{1D}$, R$^2$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^B$ and R$^C$, R$^{2B}$ and R$^{2C}$, R$^{3B}$ and R$^{3C}$ and R$^{4B}$ and R$^{4C}$ substituents bonded to the same nitrogen atom may optionally be joined to form a substituted or unsubstituted heterocycloalkyl or substituted or unsubstituted heteroaryl; and X$^1$, X$^2$, X$^3$ and X$^4$ are independently —Cl, —Br, —I or —F.

Embodiment 69

The method of Embodiment 68, wherein the compound has structural Formula (I-A):

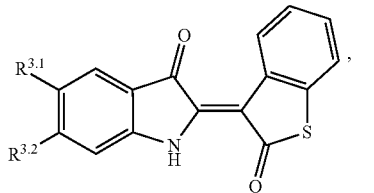

(I-A)

wherein:
n3.1 and n3.2 are independently an integer from 0 to 4;
m3.1, m3.2, v3.1 and v3.2 are independently 1 or 2;
R$^{3.1}$ is hydrogen, halogen, —CX$^1{}_3$, —CHX$^{3.1}{}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}{}_3$, —OCHX$^{3.1}{}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^{3.2}$ is hydrogen, halogen, —CX$^{3.2}{}_3$, —CHX$^{3.2}{}_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}{}_3$, —OCHX$^{3.2}{}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^{3.1A}$, R$^{3.1B}$, R$^{3.1C}$, R$^{3.1D}$, R$^{3.2A}$, R$^{3.2B}$, R$^{3.2C}$ and R$^{3.2D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.1B}$ and R$^{3.1C}$ and R$^{3.2B}$ and R$^{3.2C}$, substituents bonded to the same nitrogen atom may optionally be joined to form a substituted or unsubstituted heterocycloalkyl or substituted or unsubstituted heteroaryl; and
X$^{3.1}$ and X$^{3.2}$ are independently —Cl, —Br, —I or —F.

Embodiment 70

The method of Embodiment 68, wherein the compound has structural Formula (I-B):

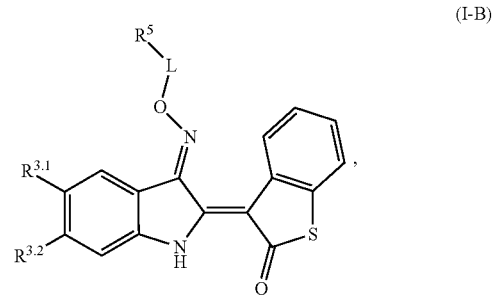

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
R$^{3.1}$ is hydrogen, halogen, —CX$^{3.1}{}_3$, —CHX$^{3.1}{}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}{}_3$, —OCHX$^{3.1}{}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^{3.2}$ is hydrogen, halogen, —CX$^{3.2}{}_3$, —CHX$^{3.2}{}_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^5$ is hydrogen, halogen, —CX$^5_3$, —CHX$^5_2$, —CH$_2$X$^5$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^5_3$, —OCHX$^5_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.1A}$, R$^{3.1B}$, R$^{3.1C}$, R$^{3.1D}$, R$^{3.2A}$, R$^{3.2B}$, R$^{3.2C}$, R$^{3.2D}$, R$^{5A}$, R$^{5B}$, R$^{5C}$ and R$^{5D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.1B}$ and R$^{3.1C}$, R$^{3.2B}$ and R$^{3.2C}$, and R$^{5B}$ and R$^{5C}$ substituents bonded to the same nitrogen atom may optionally be joined to form a substituted or unsubstituted heterocycloalkyl or substituted or unsubstituted heteroaryl; and X$^{3.1}$, X$^{3.2}$ and X$^5$ are independently —Cl, —Br, —I or —F.

Embodiment 71

The method of any one of Embodiments 69-70, wherein the cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer or prostate cancer.

Embodiment 72

The method of any one of Embodiments 68-71, wherein the cancer is a solid tumor or a blood tumor.

Embodiment 73

The method of any of Embodiments 68-72, wherein the compound is co-administered with an effective amount of an anti-cancer agent.

Embodiment 74

A method of modulating a kinase, comprising contacting the kinase with a compound, or pharmaceutically acceptable salt thereof, having structural Formula (I):

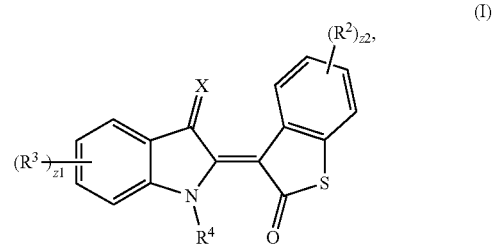

wherein:

n1, n2, n3 and n4 are independently an integer from 0 to 4;

m2, m3, v1, v2, v3 and v4 are independently 1 or 2;

z1 and z2 are independently an integer from 1 to 4;

X is =O, =S or =NR$^1$;

R$^1$ is hydrogen, halogen, —CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^2$ is independently hydrogen, halogen, —CX$^2_3$, —CHX$^2_2$, —CH$_2$X$^2$, —N$_3$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^4$ is hydrogen, halogen, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ are independently hydrogen, halogen, —CF$_3$, —CCl$_3$, —CBr$_3$, —C$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently —Cl, —Br, —I or —F.

Embodiment 75

The method of Embodiment 74, wherein the compound has structural Formula (I-A):

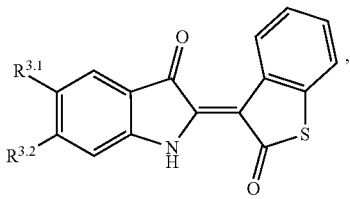

(I-A)

wherein:
n3.1 and n3.2 are independently an integer from 0 to 4;
m3.1, m3.2, v3.1 and v3.2 are independently 1 or 2;
$R^{3.1}$ is hydrogen, halogen, —CX$^{3.1}$$_3$, —CHX$^{3.1}$$_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}$$_3$, —OCHX$^{3.1}$$_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, —CX$^{3.2}$$_3$, —CHX$^{3.2}$$_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}$$_3$, —OCHX$^{3.2}$$_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$ and $R^{3.2B}$ and $R^{3.2C}$, substituents bonded to the same nitrogen atom may optionally be joined to form a substituted or unsubstituted heterocycloalkyl or substituted or unsubstituted heteroaryl; and $X^{3.1}$ and $X^{3.2}$ are independently —Cl, —Br, —I or —F.

Embodiment 76

The method of Embodiment 74, wherein the compound has structural Formula (I-B):

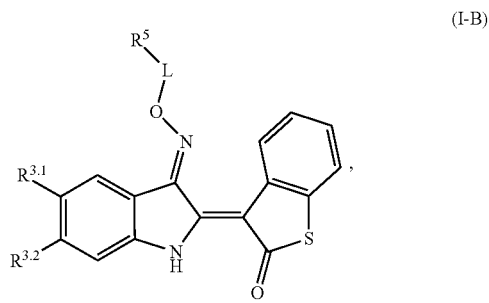

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^{3.1}$ is hydrogen, halogen, —CX$^{3.1}$$_3$, —CHX$^{3.1}$$_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}$$_3$, —OCHX$^{3.1}$$_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, —CX$^{3.2}$$_3$, —CHX$^{3.2}$$_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}$$_3$, —OCHX$^{3.2}$$_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^5$ is hydrogen, halogen, —CX$^5$$_3$, —CHX$^5$$_2$, —CH$_2$X$^5$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^5$$_3$, —OCHX$^5$$_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently —Cl, —Br, —I or —F.

Embodiment 77

The method of any one of Embodiments 74-76, wherein the kinase is JAK, JAK2, TYK2, Src, c-Src, ABL1, ABL1 T315I, an Aurora kinase, GSK-3b or a CDK.

Embodiment 78

The method of Embodiment 77, wherein the Aurora kinase is Aurora A.

Embodiment 79

A method of modulating STAT or STAT3, comprising contacting STAT or STAT3 with a compound, or pharmaceutically acceptable salt thereof, having structural Formula (I):

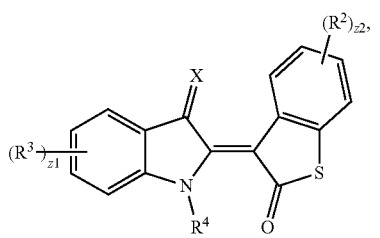

(I)

wherein:
n1, n2, n3 and n4 are independently an integer from 0 to 4;
m2, m3, v1, v2, v3 and v4 are independently 1 or 2;
z1 and z2 are independently an integer from 1 to 4;
X is =O, =S or =NR';
$R^1$ is hydrogen, halogen, —$CX^1_3$, —$CHX^1_2$, —$CH_2X^1$, —$N_3$, —CN, —$SO_{n1}R^{1A}$, —$SO_{v1}NR^{1B}R^{1C}$, —$NR^{1B}R^{1C}$, —$C(O)R^{1D}$, —$C(O)OR^{1D}$, —$C(O)NR^{1B}R^{1C}$, —$OR^{1A}$, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^2$ is independently hydrogen, halogen, —$CX^2_3$, —$CHX^2_2$, —$CH_2X^2$, —$N_3$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^2_3$, —$OCHX^2_2$, —$OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, —$CX^3_3$, —$CHX^3_2$, —$CH_2X^3$, —$N_3$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^3_3$, —$OCHX^3_2$, —$OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^4$ is hydrogen, halogen, —$CX^4_3$, —$CHX^4_2$, —$CH_2X^4$, —CN, —$SO_{n4}R^{4A}$, —$SO_{v4}NR^{4B}R^{4C}$, —$NR^{4B}R^{4C}$, —$C(O)R^{4D}$, —$C(O)OR^{4D}$, —$C(O)NR^{4B}R^{4C}$, $OR^{4A}$, —$OCX^4_3$, —$OCHX^4_2$, —$OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; RB and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently —Cl, —Br, —I or —F.

Embodiment 80

The method of Embodiment 79, wherein the compound has structural Formula (I-A):

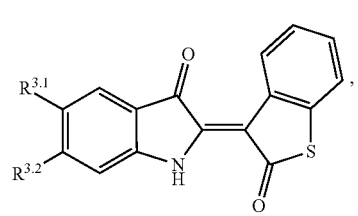

(I-A)

wherein:
n3.1 and n3.2 are independently an integer from 0 to 4;
m3.1, m3.2, v3.1 and v3.2 are independently 1 or 2;
$R^{3.1}$ is hydrogen, halogen, —$CX^{3.1}_3$, —$CHX^{3.1}_2$, —$CH_2X^{3.1}$, —$N_3$, —CN, —$SO_{n3.1}R^{3.1A}$, —$SO_{v3.1}NR^{3.1B}R^{3.1C}$, —$NHNR^{3.1B}R^{3.1C}$, —$ONR^{3.1B}R^{3.1C}$, —NHC(O)NHNR$^{3.1B}R^{3.1C}$, —NHC(O)

$NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$ and $R^{3.2B}$ and $R^{3.2C}$, substituents bonded to the same nitrogen atom may optionally be joined to form a substituted or unsubstituted heterocycloalkyl or substituted or unsubstituted heteroaryl; and $X^{3.1}$ and $X^{3.2}$ are independently $-Cl$, $-Br$, $-I$ or $-F$.

Embodiment 81

The method of Embodiment 79, wherein the compound has structural Formula (I-B):

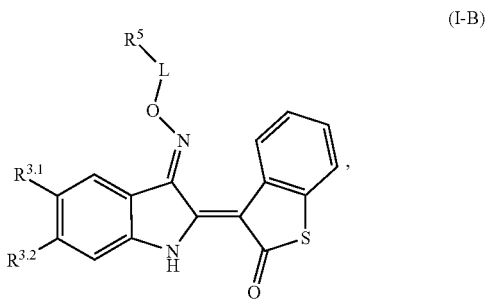

(I-B)

wherein:

n3.1, n3.2 and n5 are independently an integer from 0 to 4;

m3.1, m3.2, m5, v3.1, v3.2 and v5 are independently 1 or 2;

L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^{3.1}$ is hydrogen, halogen, $-CX^{3.1}_3$, $-CHX^{3.1}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, $-CX^5_3$, $-CHX^5_2$, $-CH_2X^5$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, $-CF_3$, $-CCl_3$, $-CBr_3$, $-C_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently $-Cl$, $-Br$, $-I$ or $-F$.

Embodiment 82

The method of any of Embodiments 68-81, wherein the compound is:

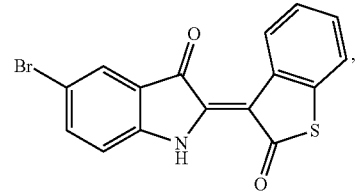

145
-continued
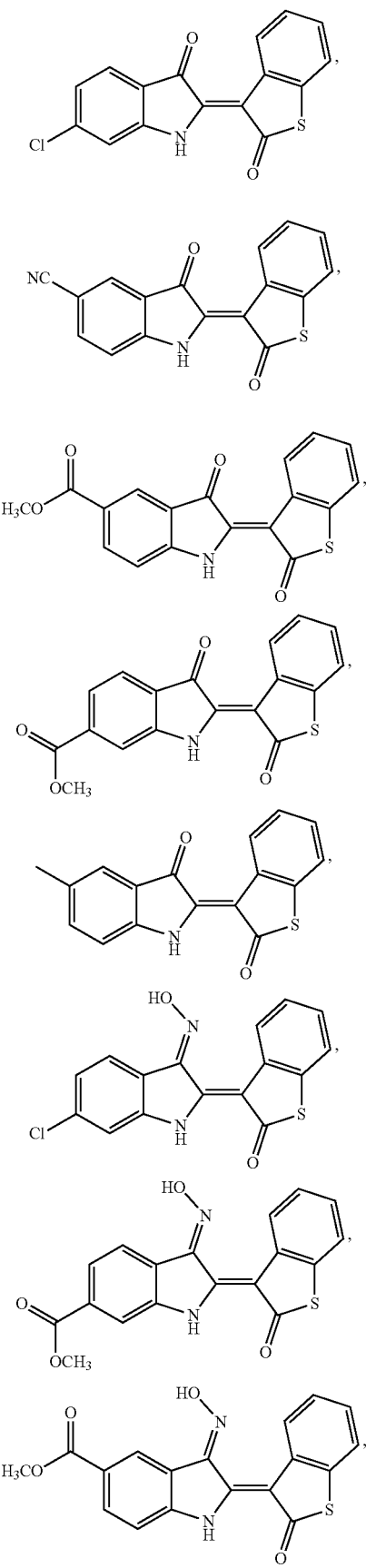
146
-continued
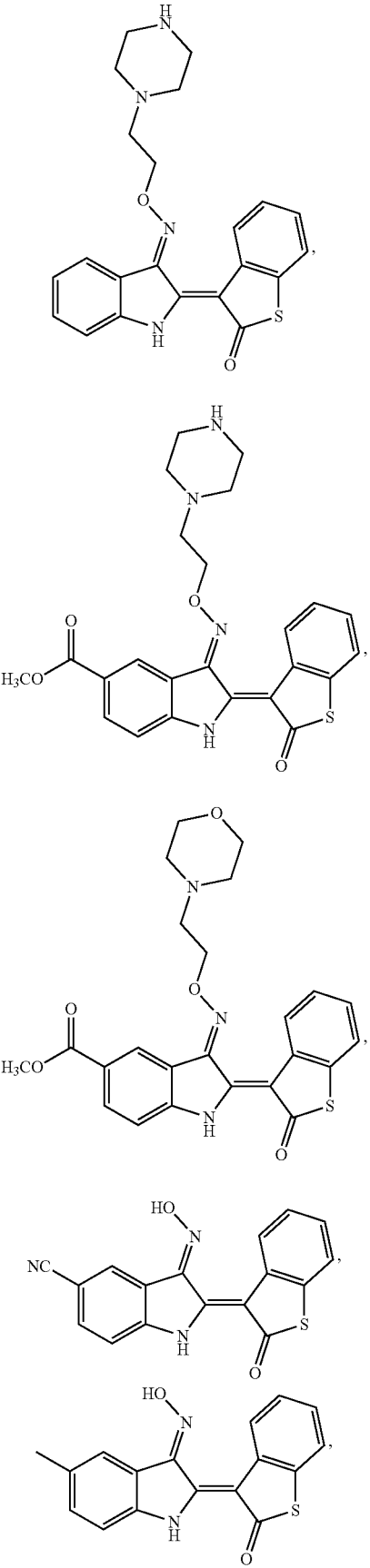

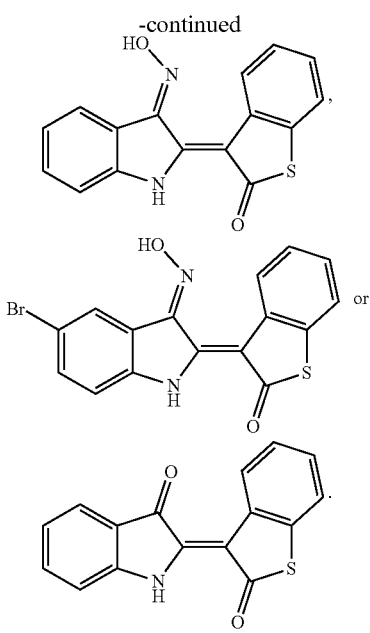

Embodiment 83

The method of any of Embodiments 68-82, wherein the compound is in a pharmaceutical composition comprising a pharmaceutically acceptable excipient.

V. EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Seventeen novel thioindirubin derivatives were synthesized and fifteen of them were tested with A2058 melanoma and DU145 prostate cancer cell lines using a cell-based assay. Compounds having a formula (II) are listed in Table 1 and compounds having a formula (I-B) are listed in Table 2.

TABLE 1

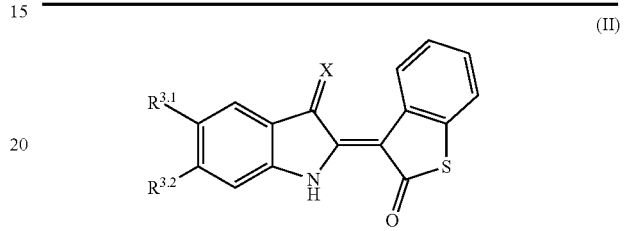

(II)

| | | | | Cell viability (% control) | | | |
|---|---|---|---|---|---|---|---|
| | | | | A2058 | | DU145 | |
| Compound | $R^{3.1}$ | $R^{3.2}$ | X | 1 μM | 10 μM | 1 μM | 10 μM |
| 6a (1573) | H | H | O | 99 | 77 | >100 | 90 |
| 6b (1574) | Br | H | O | 97 | 100 | >100 | >100 |
| 6c (1579) | H | Cl | O | 84 | 96 | 80 | 82 |
| 6d (1583) | CN | H | O | 95 | 87 | >100 | 95 |
| 6e (1575) | COOCH$_3$ | H | O | 92 | 94 | >100 | >100 |
| 6f (1581) | H | COOCH$_3$ | O | 93 | >100 | 99 | 93 |
| 6g (1577) | CH$_3$ | H | O | >100 | 97 | 94 | >100 |
| 7c (1580) | H | Cl | NOH | 86 | 27 | >100 | 33 |
| 7d (1584) | CN | H | NOH | 89 | 99 | >100 | 93 |
| 7e (1576) | COOCH$_3$ | H | NOH | 90 | 68 | >100 | 88 |
| 7f (1582) | H | COOCH$_3$ | NOH | 92 | >100 | >100 | >100 |
| 7g (1578) | CH$_3$ | H | NOH | 84 | 88 | 88 | 79 |

TABLE 2

(I-B)

| | | | | | Cell viability at 10 μM (% control) | |
|---|---|---|---|---|---|---|
| Compound | $R^{3.1}$ | $R^{3.2}$ | L | $R^5$ | A2058 | DU145 |
| 9a (1852) | H | H | —CH$_2$CH$_2$— | HN⟨piperazine⟩N— | 91 | 82 |
| 9b (1853) | COOCH$_3$ | H | —CH$_2$CH$_2$— | HN⟨piperazine⟩N— | 8 | 17 |

TABLE 2-continued

| 9c (1854) | COOCH₃ | H | —CH₂CH₂— | 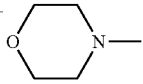 | 70 | 101 |

Example 2

A novel synthetic small molecules thioindirubin compound 9b extremely reduced viabilities of these cells at 10 µM concentration. $IC_{50}$ values (µM) of compound 9b were determined using lung cancer cell lines including non-small lung cancer cell lines (Table 3: A549, H513, H2461, H358, ad H2596) and small lung cancer cell lines (Table 4: DMS273, H69, H526, and DMS114), prostate cancer (Table 5: DU145), melanoma (Table 5: A2058). Compound 9b demonstrated strong antitumor activities with $IC_{50}$ of approximately 1 µM against some cell lines.

TABLE 3

$IC_{50}$ values (µM) against non-small lung cancer

| Compound | A549 | H513 | H2461 | H358 | H2596 |
|---|---|---|---|---|---|
| 9b | 4.6 | 1.6 | 1 | 2.4 | 1.02 |
| 7e | >10 | >10 | >10 | 7.7 | >10 |

TABLE 4

$IC_{50}$ values (µM) against small lung cancer

| Compound | DMS273 | H69 | H526 | DMS114 |
|---|---|---|---|---|
| 9b | 6.1 | 0.78 | 1.7 | 1.13 |
| 7e | >10 | >10 | >10 | >10 |

TABLE 5

$IC_{50}$ values (µM) against prostate cancer and melanoma

| Compound | DU145 (prostate cancer) | A2058 (melanoma) |
|---|---|---|
| 9b | 2.53 | 1.07 |
| 7e | >10 | >10 |

Example 3: Synthesis

General information: ¹H NMR spectra were recorded on a Bruker Avance III600 instrument, in deuterated solvents and were referenced to TMS (δ scale). Flash chromatography was performed on Merck silica gel 60 (0.040-0.063 mm). Analytical thin layer chromatography (TLC) was carried out on precoated (0.25 mm) Merck silica gel F-254 plates. Mass spectra were recorded with a LTQ Orbitrap Discovery instrument, possessing an Ionmax ionization source. 3-Acetoxyindole, 5-bromoindole, 6-chloroindole, 5-cyanoindole, methyl indole-5-carboxylate, methyl indole-6-carboxylate, 5-methylindole, iodine, potassium iodide, thiophenol, oxalyl chloride, anhydrous aluminum chloride, hydroxylamine hydrochloride, anhydrous pyridine, triethylamine, 1,2-dibromoethane, piperazine and morpholine were purchased from Sigma-Aldrich. Anhydrous dichloromethane and anhydrous N,N-dimethylformamide were purchased from Acros organics.

Example 3.1: Synthesis of Substituted Thioindiroubins 6a-2 (Scheme 1)

Step 1: General Procedure for the Synthesis of Substituted 3-iodoindoles 2b-g

Sodium hydroxide (80 mg, 2 mmol), iodine (508 mg, 2 mmol) and an aqueous solution of potassium iodide (332 mg, 2 mmol, dissolved in 2 mL of water) were added into a solution of the appropriate substituted indole (1b-g, 2 mmol) in 20 mL of methanol, and this reaction mixture was stirred at room temperature, protected from light, for 3 h. Upon completion of the reaction, an aqueous solution of $Na_2S_2O_3$ (150 mg, in 40 mL of water) was added into the flask and the mixture was left at vigorous stirring for 10 min. Then it was cooled at 0° C. for 30 min and the precipitate was filtered, washed with water and left air-dried to provide the corresponding iodo derivatives in almost quantitative yield. The resulting 3-iodoindoles 2b-g were used to the next step without further purification.

Step 2: General Procedure for the Synthesis of Substituted 3-acetoxyindoles 3b-3g Silver acetate (501 mg, 3 mmol) was added into a suspension of iodocompound 2b-g (2 mmol) in 10 mL of acetic acid and this mixture was heated at 95° C. for 90 min, under argon. Upon completion of the reaction, the mixture was allowed to reach room temperature and was filtered under vacuum. The inorganic solid was washed with ethyl acetate (40 mL) and the filtrate was evaporated under reduced pressure. The crude product was purified with flash chromatography to provide the pure 3-acetoxyindoles 3b-g.

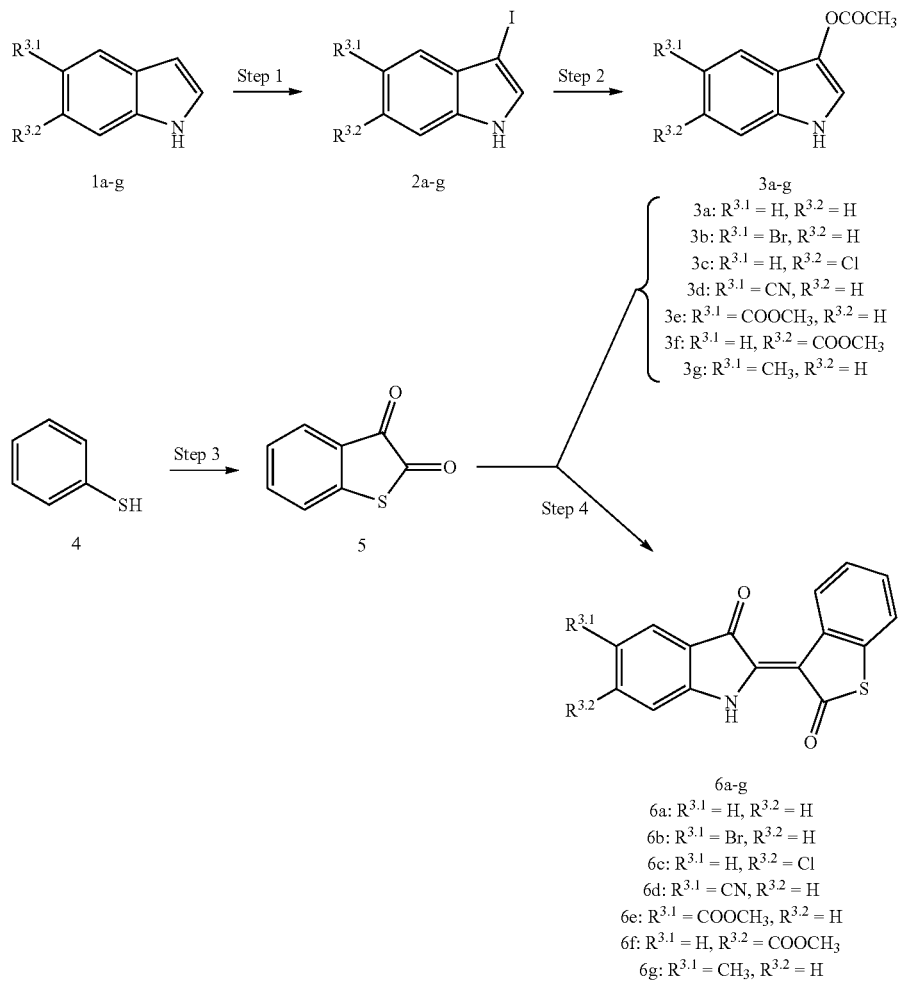

Scheme 1

5-Bromo-1H-indol-3-yl acetate (3b)

This compound was synthesized according to the general procedure described above, starting from iodocompound 2b, in 63% yield. $^1$H-NMR (600 MHz, CDCl$_3$) δ 2.38 (3H, s, OCOCH$_3$), 7.23 (1H, d, J=8.9 Hz, H-7), 7.32 (1H, dd, J=8.9, 1.7 Hz, H-6), 7.40 (1H, d, J=2.7 Hz, H-2), 7.72 (1H, d, J=1.7 Hz, H-4), 7.92 (1H, brs, N—H). HRMS (ESI) m/z: cald. for C$_{10}$H$_9$BrNO$_2$: [M1+H]$^+$=253.9811, 255.9791, found 253.9807, 255.9787.

6-Chloro-1H-indol-3-yl acetate (3c)

This compound was synthesized according to the general procedure described above, starting from iodocompound 2c, in 74% yield. $^1$H-NMR (600 MHz, CDCl$_3$) δ 2.36 (3H, s, OCOCH$_3$), 7.11 (1H, dd, J=8.5, 1.6 Hz, H-5), 7.34 (1H, d, J=1.6 Hz, H-7), 7.38 (1H, d, J=2.4 Hz, H-2), 7.47 (1H, d, J=8.5, H-4), 7.84 (1H, brs, N—H). HRMS (ESI) m/z: calcd. for C$_{10}$H$_9$ClNO$_2$: [M1+H]$^+$=210.0316, found 210.0311.

5-Cyano-1H-indol-3-yl acetate (3d)

This compound was synthesized according to the general procedure described above, starting from iodocompound 2d, in 69% yield. $^1$H-NMR (600 MHz, CDCl$_3$) δ 2.39 (3H, s, OCOCH$_3$), 7.39 (1H, d, J=8.5 Hz, H-7), 7.44 (1H, dd, J=8.5, 1.4 Hz, H-6), 7.51 (1H, d, J=2.7 Hz, H-2), 7.95 (1H, d, J=1.4 Hz, H-4), 8.28 (1H, brs, N—H). HRMS (ESI) m/z: calcd. for C$_{11}$H$_9$N$_2$O$_2$: [M1+H]$^+$=201.0659, found 201.0656.

Methyl 3-acetoxy-1H-indole-5-carboxylate (3e)

This compound was synthesized according to the general procedure described above, starting from iodocompound 2e, in 90% yield. $^1$H-NMR (600 MHz, CDCl$_3$) δ 2.39 (3H, s, OCOCH$_3$), 3.94 (3H, s, COOCH$_3$), 7.35 (1H, d, J=8.5 Hz, H-7), 7.45 (1H, d, J=2.4 Hz, H-2), 7.93 (1H, dd, J=8.5, 1.5 Hz, H-6), 8.04 (1H, brs, N—H), 8.35 (1H, d, J=1.5 Hz, H-4). HRMS (ESI) m/z: calcd. for C$_{12}$H$_{12}$NO$_4$: [M1+H]$^+$=234.0761, found 234.0757.

Methyl 3-acetoxy-1H-indole-6-carboxylate (3f)

This compound was synthesized according to the general procedure described above, starting from iodocompound 2f, in 76% yield. $^1$H-NMR (600 MHz, CDCl$_3$) δ 2.38 (3H, s, OCOCH$_3$), 3.94 (3H, s, COOCH$_3$), 7.56 (1H, d, J=2.7 Hz, H-2), 7.59 (1H, d, J=8.4 Hz, H-4), 7.83 (1H, dd, J=8.4, 1.0

Hz, H-5), 8.11 (2H, m, N—H, H-7). HRMS (ESI) m/z: calcd. for $C_{12}H_{12}NO_4$: [M1+H]$^+$=234.0761, found 234.0754.

5-Methyl-1H-indol-3-yl acetate (3g)

This compound was synthesized according to the general procedure described above, starting from iodocompound 2g, in 61% yield. $^1$H-NMR (600 MHz, CDCl$_3$) δ 2.38 (3H, s, OCOCH$_3$), 2.47 (3H, s, CH$_3$), 7.06 (1H, d, J=8.4 Hz, H-7), 7.25 (1H, d, J=8.4 Hz, H-6), 7.33 (1H, d, J=2.4 Hz, H-2), 7.35 (1H, s, H-4), 7.77 (1H, brs, N—H). HRMS (ESI) m/z: calcd. for $CH_{12}NO_2$: [M1+H]$^+$=190.0863, found 190.0856.

Step 3: Synthesis of Thioisatine (benzo[b]thiophene-2,3-dione, 5)

A solution of thiophenol (4, 4 mL, 39 mmol) in anhydrous dichloromethane (10 mL) was added dropwise into a solution of oxalyl chloride (10.16 mL, 120 mmol) in 50 mL of anhydrous dichloromethane and this mixture was refluxed for 45 min. Upon cooling, solvents were evaporated, the residue was dissolved in 65 mL of anhydrous dichloromethane, followed by addition of anhydrous AlCl$_3$ (10.67 g, 80 mmol) in three portions, and this mixture was refluxed for 90 min. Upon completion of the reaction, the crude mixture was left to reach room temperature and then it was poured carefully in crashed ice (300 mL) and was extracted with dichloromethane (3×300 mL). The combined organic layers were dried over sodium sulfate and evaporated. The crude product was purified by column chromatography using a mixture of cyclohexane/ethyl acetate (from 100/5 up to 100/15, v/v) as the eluent to provide the pure thioisatine 5 (4.48 g, yield 70%). $^1$H-NMR (600 MHz, CDCl$_3$) δ 7.37 (1H, t, J=7.6 Hz, H-5), 7.42 (1H, d, J=7.8 Hz, H-7), 7.68 (1H, t, J=7.7 Hz, H-6), 7.82 (1H, d, J=7.6 Hz, H-4).

Step 4: General Procedure for the Synthesis of Thioindirubins 6a-g

The appropriate substituted 3-acetoxyindole 3a-g (2 mmol) was added into a solution of thioisatine (5, 328 mg, 2 mmol) in acetic acid (12 mL), followed by dropwise addition of HCl 36% (0.2 mL). The reaction was stirred at room temperature for 18 hrs, under light protection. Then it was diluted with water (100 mL), sodium bicarbonate (250 mg) was added and the mixture was stirred for 5 min, followed by extraction with dichloromethane (3×100 mL). The combined organic layers were washed twice with water (250 mL) and once with brine (250 mL), dried over sodium sulfate and evaporated. The crude product was purified by column chromatography to provide the pure thioindirubins 6a-g.

(2'Z)-Thioindirubin (6a)

This compound was synthesized according to the general procedure described above, upon reaction of thioisatine 5 with indole 3a. The product was purified by column chromatography, using a mixture of cyclohexane/dichloromethane (from 50/50 up to 0/100, v/v) as the eluent, to provide the pure thioindirubin 6a in 82% yield. $^1$H-NMR (600 MHz, DMSO-d$_6$) δ 7.12 (1H, t, J=7.5 Hz, H-5'), 7.33 (1H, t, J=7.5 Hz, H-5), 7.37 (1H, t, J=7.5 Hz, H-6'), 7.47 (1H, d, J=7.5 Hz, H-7), 7.58-7.63 (2H, m, H-6, H-7'), 7.69 (1H, d, J=7.6 Hz, H-4'), 9.16 (1H, d, J=7.5 Hz, H-4), 11.72 (1H, s, N'—H). HRMS (ESI) m/z: calcd. for $C_{16}H_{10}NO_2S$: [M1+H]$^+$= 280.0427, found 280.0423.

(2'Z)-5'-Bromothioindirubin (6b)

This compound was synthesized according to the general procedure described above, upon reaction of thioisatine 5 with indole 3b. The product was purified by column chromatography, using a mixture of cyclohexane/dichloromethane (from 50/50 up to 20/80, v/v) as the eluent, to provide the pure thioindirubin 6b in 56% yield. $^1$H-NMR (600 MHz, DMSO-d$_6$) δ 7.35 (1H, t, J=7.5 Hz, H-5), 7.40 (1H, t, J=7.5 Hz, H-6), 7.45 (1H, d, J=7.5 Hz, H-7), 7.62 (1H, d, J=7.0 Hz, H-7'), 7.79 (1H, d, J=7.0 Hz, H-6'), 7.82 (1H, s, H-4'), 9.13 (1H, d, J=7.5 Hz, H-4), 11.76 (1H, s, —N'—H). HRMS (ESI) m/z: calcd. for $C_{16}H_9BrNO_2S$: [M1+H]$^+$=357.9532, 359.9511, found 357.9526, 359.9505.

(2'Z)-6'-Chlorothioindirubin (6c)

This compound was synthesized according to the general procedure described above, upon reaction of thioisatine 5 with indole 3c. The product was purified by column chromatography, using a mixture of cyclohexane/dichloromethane (50/50, v/v) as the eluent, to provide the pure thioindirubin 6c in 61% yield. $^1$H-NMR (600 MHz, DMSO-d$_6$) δ 7.15 (1H, d, J=7.3 Hz, H-7), 7.38 (2H, m, H-5, H-6), 7.55 (1H, s, H-7'), 7.61 (1H, d, J=7.2 Hz, H-5'), 7.70 (1H, d, J=7.2 Hz, H-4'), 9.15 (1H, d, J=7.3 Hz, H-4), 11.74 (1H, s, N'—H). HRMS (ESI) m/z: calcd. for $C_{16}H_9ClNO_2S$: [M1+H]$^+$=314.0037, found 314.0033.

(2'Z)-5'-Cyanothioindirubin (6d)

This compound was synthesized according to the general procedure described above, upon reaction of thioisatine 5 with indole 3d. The product was purified by column chromatography, using a mixture of cyclohexane/dichloromethane (from 50/50 up to 30/70, v/v) as the eluent, to provide the pure thioindirubin 6d in 68% yield. $^1$H-NMR (600 MHz, DMSO-d$_6$) δ 7.36 (1H, t, J=7.3 Hz, H-5), 7.42 (1H, t, J=7.3 Hz, H-6), 7.62 (2H, m, H-7, H-7'), 8.02 (1H, d, J=7.0 Hz, H-6'), 8.18 (1H, s, H-4'), 9.15 (1H, d, J=7.3 Hz, H-4), 11.94 (1H, s, N'—H). HRMS (ESI) m/z: calcd. for $C_{17}H9N_2O_2S$: [M1+H]$^+$=305.0379, found 305.0376.

(2'Z)-5'-(Methoxycarbonyl)thioindirubin (6e)

This compound was synthesized according to the general procedure described above, upon reaction of thioisatine 5 with indole 3e. The product was purified by column chromatography, using a mixture of cyclohexane/dichloromethane (from 50/50 up to 0/100, v/v) as the eluent, to provide the pure thioindirubin 6e in 76% yield. $^1$H-NMR (600 MHz, DMSO-d$_6$) δ 3.87 (3H, s, COOCH$_3$), 7.37 (1H, t, J=7.6 Hz, H-5), 7.42 (1H, t, J=7.6 Hz, H-6), 7.58 (1H, d, J=7.6 Hz, H-7), 7.63 (1H, d, J=7.5 Hz, H-7'), 8.14 (1H, s, H-4'), 8.19 (1H, d, J=7.5 Hz, H-6'), 9.18 (1H, d, J=7.6 Hz, H-4), 11.92 (1H, s, N'—H). HRMS (ESI) m/z: calcd. for $C_{18}H_{12}NO_4S$: [M1+H]$^+$=338.0482, found 338.0479.

(2'Z)-6'-(Methoxycarbonyl)thioindirubin (6f)

This compound was synthesized according to the general procedure described above, upon reaction of thioisatine 5 with indole 3f. The product was purified by column chromatography, using a mixture of cyclohexane/dichloromethane (from 50/50 up to 20/80, v/v) as the eluent, to provide the pure thioindirubin 6f in 72% yield. $^1$H-NMR (600 MHz, DMSO-$d_6$) δ 3.91 (3H, s, COOCH$_3$), 7.38 (2H, m, H-5, H-6), 7.62 (1H, d, J=7.0 Hz, H-7), 7.66 (1H, d, J=7.2 Hz, H-4'), 7.80 (1H, d, J=7.2 Hz, H-5'), 8.08 (1H, s, H-7'), 9.14 (1H, d, J=7.0 Hz, H-4), 11.85 (1H, s, N'—H). HRMS (ESI) m/z: calcd. for $C_{18}H_{12}NO_4S$: [M1+H]$^+$=338.0482, found 338.0476.

(2'Z)-5'-Methylthioindirubin (6g)

This compound was synthesized according to the general procedure described above, upon reaction of thioisatine 5 with indole 3g. The product was purified by column chromatography, using a mixture of cyclohexane/dichloromethane (50/50, v/v) as the eluent, to provide the pure thioindirubin 6g in 48% yield. $^1$H-NMR (600 MHz, DMSO-$d_6$) δ 2.33 (3H, s, CH$_3$), 7.36 (3H, m, H-5, H-6, H-7), 7.45 (1H, d, J=7.0 Hz, H-7'), 7.50 (1H, s, H-4'), 7.60 (1H, d, J=7.0 Hz, H-6'), 9.14 (1H, d, J=7.3 Hz, H-4), 11.66 (1H, s, N'—H). HRMS (ESI) m/z: calcd. for $C_{17}H_{12}NO_2S$: [M1+H]$^+$= 294.0583, found 294.0577.

Example 3.2: Synthesis of the Oximes of Thioindiroubins 7a-g (Scheme 2)

Step 1: General Procedure for the Synthesis of the 3'-oximes of thioindirubins 7a-g Hydroxylamine hydrochloride (347 mg, 5 mmol) was added into a solution of the appropriate thioindirubin 6a-g (0.5 mmol) in anhydrous pyridine (10 mL) and this mixture was refluxed for 45-60 min, under argon. Upon cooling, water (100 mL) was added, followed by extraction with dichloromethane (3×100 mL). The combined organic layers were dried over sodium sulfate and evaporated. The crude product was purified by column chromatography to provide the pure thioindirubin oximes 7a-g.

Scheme 2

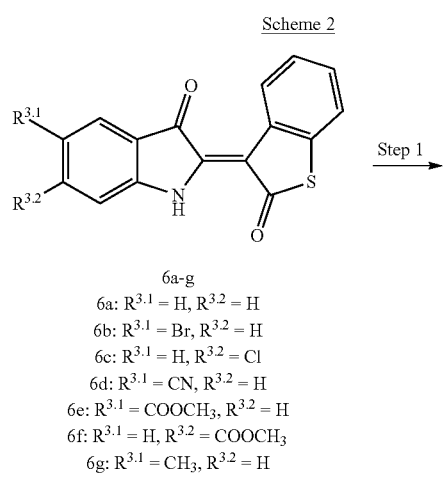

6a-g
6a: $R^{3.1}$ = H, $R^{3.2}$ = H
6b: $R^{3.1}$ = Br, $R^{3.2}$ = H
6c: $R^{3.1}$ = H, $R^{3.2}$ = Cl
6d: $R^{3.1}$ = CN, $R^{3.2}$ = H
6e: $R^{3.1}$ = COOCH$_3$, $R^{3.2}$ = H
6f: $R^{3.1}$ = H, $R^{3.2}$ = COOCH$_3$
6g: $R^{3.1}$ = CH$_3$, $R^{3.2}$ = H

-continued

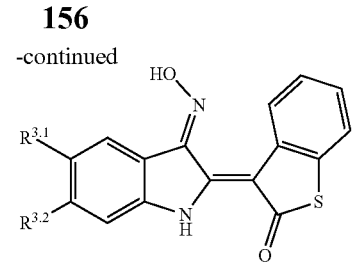

7a-g
7a: $R^{3.1}$ = H, $R^{3.2}$ = H
7b: $R^{3.1}$ = Br, $R^{3.2}$ = H
7c: $R^{3.1}$ = H, $R^{3.2}$ = Cl
7d: $R^{3.1}$ = CN, $R^{3.2}$ = H
7e: $R^{3.1}$ = COOCH$_3$, $R^{3.2}$ = H
7f: $R^{3.1}$ = H, $R^{3.2}$ = COOCH$_3$
7g: $R^{3.1}$ = CH$_3$, $R^{3.2}$ = H (2'Z,3'E)-Thioindirubin-3'-oxime (7a)

This compound was synthesized according to the general procedure described above, starting from 6a. The product was purified by column chromatography, using a mixture of cyclohexane/ethyl acetate (100/15, v/v) as the eluent, to provide the pure oxime 7a in 26% yield. $^1$H-NMR (600 MHz, DMSO-$d_6$) δ 7.16 (1H, t, J=7.5 Hz, H-5'), 7.24 (2H, m, H-5, H-6), 7.47 (1H, t, J=7.5 Hz, H-6'), 7.53 (2H, m, H-7, H-7'), 8.28 (1H, d, J=7.7 Hz, H-4'), 9.04 (1H, m, H-4), 12.45 (1H, s, N'—H), 14.01 (1H, s, NOH). HRMS (ESI) m/z: calcd. for $C_{16}H_{11}N_2O_2S$: [M1+H]$^+$=295.0536, found 295.0531.

(2'Z,3'E)-5'-Bromothioindirubin-3'-oxime (7b)

This compound was synthesized according to the general procedure described above, starting from 6b. The product was purified by column chromatography, using a mixture of cyclohexane/ethyl acetate (100/10, v/v) as the eluent, to provide the pure oxime 7b in 23% yield. $^1$H-NMR (600 MHz, DMSO-$d_6$) δ 7.24 (2H, m, H-5, H-6), 7.52 (2H, m, H-7, H-7'), 7.63 (1H, d, J=8.1 Hz, H-6'), 8.39 (1H, s, H-4'), 9.13 (1H, d, J=8.8 Hz, H-4), 12.48 (1H, s, N'—H), 14.27 (1H, s, NOH). HRMS (ESI) m/z: calcd. for $C_{16}H_{10}BrN_2O_2S$: [M1+H]$^+$=372.9641, 374.9620, found 372.9633, 374.9612.

(2'Z,3'E)-6'-Chlorothioindirubin-3'-oxime (7c)

This compound was synthesized according to the general procedure described above, starting from 6c. The product was purified by column chromatography, using a mixture of cyclohexane/ethyl acetate (100/10, v/v) as the eluent, to provide the pure oxime 7c in 35% yield. $^1$H-NMR (600 MHz, DMSO-$d_6$) δ 7.19 (1H, d, J=7.5 Hz, H-7), 7.26 (2H, m, H-5, H-6), 7.56 (1H, d, J=7.6 Hz, H-5'), 7.64 (1H, s, H-7'), 8.26 (1H, d, J=7.6 Hz, H-4'), 9.05 (1H, d, J=7.5 Hz, H-4), 12.42 (1H, s, —N'—H), 14.10 (1H, brs, NOH). HRMS (ESI) m/z: calcd. for $C_{16}H_{10}ClN_2O_2S$: [M1+H]$^+$=329.0146, found 329.0140.

(2'Z,3'E)-5'-Cyanothioindirubin-3'-oxime (7d)

This compound was synthesized according to the general procedure described above, starting from 6d. The product was purified by column chromatography, using a mixture of cyclohexane/ethyl acetate (100/15, v/v) as the eluent, to provide the pure oxime 7d in 27% yield. $^1$H-NMR (600 MHz, DMSO-$d_6$) δ 7.27 (2H, m, H-5, H-6), 7.56 (1H, d, J=7.3 Hz, H-7), 7.68 (1H, d, J=8.3 Hz, H-7'), 7.90 (1H, d, J=8.3 Hz, H-6'), 8.59 (1H, s, H-4'), 9.04 (1H, d, J=7.3 Hz, H-4), 12.57 (1H, s, —N'—H), 14.26 (1H, s, NOH). HRMS (ESI) m/z: calcd. for $C_{17}H_{10}N_3O_2S$: $[M1+H]^+$=320.0488, found 320.0481.

(2'Z,3'E)-5'-(Methoxycarbonyl)thioindirubin-3'-oxime (7e)

This compound was synthesized according to the general procedure described above, starting from 6e. The product was purified by column chromatography, using a mixture of cyclohexane/ethyl acetate (100/15, v/v) as the eluent, to provide the pure oxime 7e in 3$_3$% yield. $^1$H-NMR (600 MHz, DMSO-$d_6$) δ 3.87 (3H, s, COOCH$_3$), 7.27 (2H, m, H-5, H-6), 7.56 (1H, d, J=8.1 Hz, H-7), 7.61 (1H, d, J=8.3 Hz, H-7'), 8.06 (1H, d, J=8.3 Hz, H-6'), 8.85 (1H, s, H-4'), 9.06 (1H, d, J=8.1 Hz, H-4), 12.56 (1H, s, N'—H), 14.23 (1H, s, NOH). HRMS (ESI) m/z: calcd. for $C_{18}H_{13}N_2O_4S$: $[M1+H]^+$=353.0591, found 353.0587.

(2'Z,3'E)-6'-(Methoxycarbonyl)thioindirubin-3'-oxime (7f)

This compound was synthesized according to the general procedure described above, starting from 6f. The product was purified by column chromatography, using a mixture of cyclohexane/ethyl acetate (100/12, v/v) as the eluent, to provide the pure oxime 7f in 34% yield. $^1$H-NMR (600 MHz, DMSO-$d_6$) δ 3.89 (3H, s, COOCH$_3$), 7.21 (2H, m, H-5, H-6), 7.51 (1H, H-7), 7.75 (1H, d, J=7.5 Hz, H-5'), 8.12 (1H, s, H-7'), 8.39 (1H, d, J=7.5 Hz, H-4'), 9.01 (1H, d, J=7.3 Hz, H-4), 12.60 (1H, s, N'—H), 14.31 (1H, brs, NOH). HRMS (ESI) m/z: calcd. for $C_{18}H_{13}N_2O_4S$: $[M1+H]^+$=353.0591, found 353.0583.

(2'Z,3'E)-5'-Methylthioindirubin-3'-oxime (7g)

This compound was synthesized according to the general procedure described above, starting from 6g. The product was purified by column chromatography, using a mixture of cyclohexane/ethyl acetate (100/10, v/v) as the eluent, to provide the pure oxime 7g in 29% yield. $^1$H-NMR (600 MHz, DMSO-$d_6$) δ 2.35 (3H, s, CH$_3$), 7.24 (2H, m, H-5, H-6), 7.29 (1H, d, J=7.5 Hz, H-7), 7.41 (1H, d, J=7.3 Hz, H-7'), 7.53 (1H, d, J=7.3 Hz, H-6'), 8.12 (1H, s, H-4'), 9.03 (1H, d, J=7.5 Hz, H-4), 12.43 (1H, s, N'—H), 13.98 (1H, brs, NOH). HRMS (ESI) m/z: calcd. for $C_{17}H_{13}N_2O_2S$: $[M1+H]^+$=309.0692, found 309.0688.

Example 3.3: Synthesis of the Aminoalkylethers of the Oximes of Thioindiroubins 9a-c (Scheme 3)

Step 1: General Procedure for the Synthesis of 3'-[O-(2-Bromoethyl)] Derivatives of the Thioindirubin-3'-Oximes 8a, 8e Triethylamine (42 µL, 0.3 mmol) and 1,2-dibromoethane (78 µL, 0.9 mmol) were added into a solution of the appropriate oxime 7a or 7e (0.3 mmol) in anhydrous N N-dimethylformamide (4 mL) and this mixture was stirred under argon for 5 hrs. Upon completion of the reaction, water (50 mL) was added and it was extracted with ethyl acetate (3×50 mL). The combined organic layers were dried over sodium sulfate and evaporated. The crude product was purified by column chromatography to provide the pure derivatives 8a and 8e.

(2'Z,3'E)-Thioindirubin-3'-[O-(2-bromoethyl)]oxime (8a)

This compound was synthesized according to the general procedure described above, starting from 7a. The product was purified by column chromatography, using a mixture of cyclohexane/ethyl acetate (100/10, v/v) as the eluent, to provide the pure derivative 8a in 40% yield. $^1$H-NMR (600 MHz, DMSO-$d_6$) δ 3.96 (2H, t, J=5.5 Hz, H-2"), 4.88 (2H, t, J=5.5 Hz, H-1"), 7.16 (1H, t, J=7.8 Hz, H-5'), 7.26 (2H, m, H-5, H-6), 7.52 (3H, m, H-7, H-6', H-7'), 8.22 (1H, d, J=7.6 Hz, H-4'), 8.93 (1H, m, H-4), 12.24 (1H, s, N'—H). HRMS (ESI) m/z: calcd. for $C_{18}H_{14}BrN_2O_2S$: $[M1+H]^+$=400.9954, 402.9933, found 400.9951, 402.9930.

Scheme 3

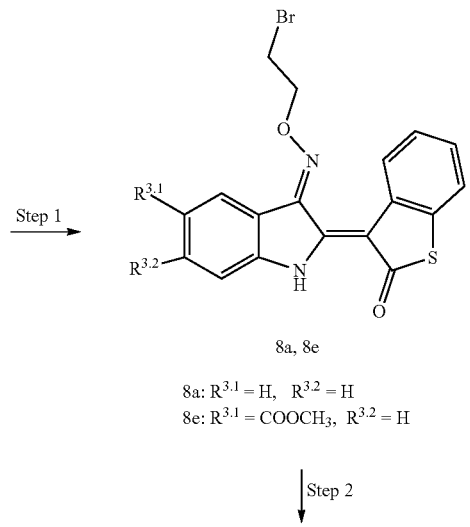

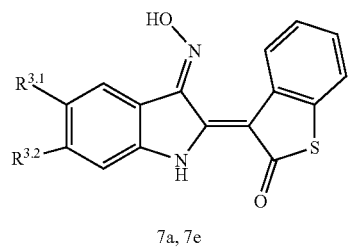

7a, 7e

7a: $R^{3.1}$ = H, $R^{3.2}$ = H
7e: $R^{3.1}$ = COOCH$_3$, $R^{3.2}$ = H 8a, 8e

8a: $R^{3.1}$ = H, $R^{3.2}$ = H
8e: $R^{3.1}$ = COOCH$_3$, $R^{3.2}$ = H

Step 2

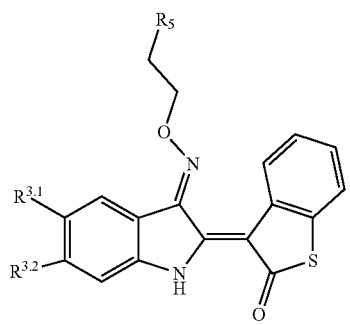

9a-c

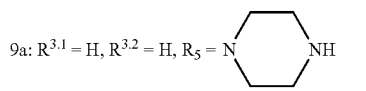

9a: $R^{3.1}$ = H, $R^{3.2}$ = H, $R_5$ =

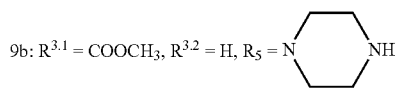

9b: $R^{3.1}$ = COOCH$_3$, $R^{3.2}$ = H, $R_5$ =

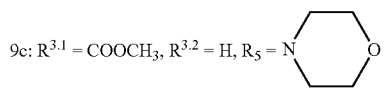

9c: $R^{3.1}$ = COOCH$_3$, $R^{3.2}$ = H, $R_5$ =

(2'Z,3'E)-5'-(Methoxycarbonyl)thioindirubin-3'-[O-(2-bromoethyl)]oxime (8e)

This compound was synthesized according to the general procedure described above, starting from 7e. The product was purified by column chromatography, using a mixture of cyclohexane/ethyl acetate (100/10, v/v) as the eluent, to provide the pure derivative 8e in 48% yield. $^1$H-NMR (600 MHz, CDCl$_3$) δ 3.82 (2H, t, J=6.2 Hz, H-2"), 3.94 (3H, s, COOCH$_3$), 4.92 (2H, t, J=6.2 Hz, H-1"), 7.08 (1H, d, J=8.3 Hz, H-7'), 7.28 (2H, m, H-5, H-6), 7.44 (1H, m, H-7), 8.16 (1H, dd, J=8.3, 1.7 Hz, H-6'), 8.92 (1H, s, H-4'), 9.05 (1H, m, H-4), 12.46 (1H, s, N'—H). HRMS (ESI) m/z: calcd. for C$_{20}$H$_{16}$BrN$_2$O$_4$S: [M1+H]$^+$=459.0009, 460.9988, found 459.0002, 460.9981.

Step 2: General Procedure for the Synthesis of 3'-[O-(2-aminoethyl)] derivatives of the thioindirubin-3'-oximes 9a-c Piperazine or morpholine (1 mmol) was added into a solution of the derivative 8a or 8e (0.1 mmol) in anhydrous N,N-dimethylformamide (2 mL) and this mixture was stirred under argon for 2 hrs. Upon completion of the reaction, water (30 mL) was added, followed by extraction with ethyl acetate (3×30 mL). The combined organic layers were washed with water (100 mL) and with brine (100 mL), dried over sodium sulfate and evaporated. The crude product was purified by column chromatography to provide the pure target derivatives 9a-c.

(2'Z,3'E)-Thioindirubin-3'-[O-(2-(piperazin-1-yl)ethyl)]oxime (9a)

This compound was synthesized according to the general procedure described above, upon reaction of 8a with piperazine. The product was purified by column chromatography, using a mixture of dichloromethane/methanol (from 100/10 up to 100/20, v/v) as the eluent, to provide the pure target derivative 9a in 48% yield. $^1$H-NMR (600 MHz, DMSO-d$_6$) δ 2.66 (4H, br s, piperazine H), 2.90 (2H, t, J=5.7 Hz, H-2"), 2.97 (4H, br s, piperazine H), 4.69 (2H, t, J=5.7 Hz, H-1"), 7.15 (1H, t, J=7.8 Hz, H-5'), 7.27 (2H, m, H-5, H-6), 7.51 (3H, m, H-7, H-6', H-7'), 8.19 (1H, d, J=7.7 Hz, H-4'), 8.98 (1H, m, H-4), 12.30 (1H, br s, N'—H). HRMS (ESI) m/z: calcd. for C$_{22}$H$_{23}$N$_4$O$_2$S: [M1+H]$^+$=407.1536, found 407.1530.

(2'Z,3'E)-5'-(Methoxycarbonyl)thioindirubin-3'-[O-(2-(piperazin-1-yl)ethyl)]oxime (9b)

This compound was synthesized according to the general procedure described above, upon reaction of 8e with piperazine. The product was purified by column chromatography, using a mixture of dichloromethane/methanol (from 100/10 up to 100/18, v/v) as the eluent, to provide the pure target derivative 9b in 56% yield. $^1$H-NMR (600 MHz, DMSO-d$_6$) δ 2.71 (4H, br s, piperazine H), 2.93 (2H, t, J=5.5 Hz, H-2"), 3.04 (4H, br s, piperazine H), 3.87 (3H, s, COOCH$_3$), 4.74 (2H, t, J=5.5 Hz, H-1"), 7.30 (2H, m, H-5, H-6), 7.56 (1H, m, H-7), 7.60 (1H, d, J=8.3 Hz, H-7'), 8.09 (1H, dd, J=8.3, 1.7 Hz, H-6'), 8.71 (1H, d, J=1.7 Hz, H-4'), 8.99 (1H, m, H-4), 12.40 (1H, br s, N'—H). HRMS (ESI) m/z: calcd. for C$_{24}$H$_{25}$N$_4$O$_4$S: [M1+H]$^+$=465.1591, found 465.1585.

(2'Z,3'E)-5'-(Methoxycarbonyl)thioindirubin-3'-[O-(2-(morpholino)ethyl)]oxime (9c)

This compound was synthesized according to the general procedure described above, upon reaction of 8e with morpholine. The product was purified by column chromatography, using a mixture of dichloromethane/methanol (from 100/1 up to 100/3, v/v) as the eluent, to provide the pure target derivative 9c in 4$_3$% yield. $^1$H-NMR (600 MHz, CDCl$_3$) δ 2.69 (4H, br s, morpholine H), 3.01 (2H, t, J=5.5 Hz, H-2"), 3.78 (4H, br s, morpholine H), 3.94 (3H, s, COOCH$_3$), 4.82 (2H, t, J=5.5 Hz, H-1"), 7.08 (1H, d, J=8.3

Hz, H-7'), 7.29 (2H, m, H-5, H-6), 7.42 (1H, m, H-7), 8.12 (1H, dd, J=8.3, 1.7 Hz, H-6'), 8.88 (1H, d, J=1.7 Hz, H-4'), 9.11 (1H, m, H-4), 12.54 (1H, s, N'—H). HRMS (ESI) m/z: calcd. for $C_{24}H_{24}N_3O_5S$: $[M1+H]^+=466.1431$, found 466.1422.

Example 4: Viability Assay

To determine if novel synthetic thioindirubins have antitumor activities, we performed an MTS cell viability assay. Initially, we screened them at 10 M final concentration with A2058 melanoma and DU145 prostate cancer cell lines. Then, compound 9b and compound 7e were selected to determine $IC_{50}$ values against prostate cancer, melanoma and lung cancer cells, including DU145, A2058, A549, H513, H2461, H358, DMS114, H2596, DMS273, H69, H526 and DMS114 cell lines. For the viability assay, 5000 cells/well were seeded in 96-well plates, incubated overnight at 37° C. in 5% $CO_2$ and then exposed to 10 M of compounds or in a dose-dependent manner for 48 h. After 48 h treatment with compounds, MTS dye (20 μL/well) was added to 96-well plates. Viable cell numbers were determined by tetrazolium conversion to its formazan dye. Absorbance was measured at 490 nm using the BMG LABTECH plate reader. Dimethyl sulfoxide (DMSO) was used as the vehicle control. Each experiment was conducted in triplicate. $IC_{50}$ values were determined using CalcuSyn software (Biosoft).

Example 5

The structure activity relationship (SAR) study is carried out for development of anticancer therapeutic agents. Previously, we demonstrated that several indirubin derivatives (IRDs) molecularly target multi kinases. As the structures of these thioindirubins are similar with IRDs, a kinase profiling experiment can be performed using the PamGene array platform for molecular target identification and specificity of the compounds of the invention (e.g. compound 9b). Next, in order to understand the pharmacological action of the active compounds of the invention (e.g. compound 9b), the molecular mechanism of action is studied in both solid and blood tumor cells. In addition, in vivo efficacy can be measured using a mouse model study.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or pharmaceutically acceptable salt thereof, having structural Formula (I):

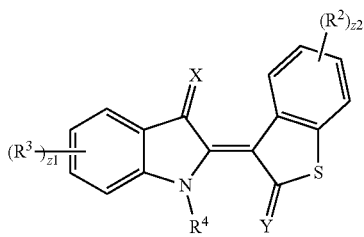

(I)

wherein:

n1, n2, n3, n4 and n6 are independently an integer from 0 to 4;

m2, m3, v1, v2, v3, v4 and v6 are independently 1 or 2;

z1 and z2 are independently an integer from 1 to 4;

X is =O, =S or =$NR^1$;

Y is =O, =S or =$NR^6$;

$R^1$ is hydrogen, halogen, oxo, —$CX^1_3$, —$CHX^1_2$, —$CH_2X^1$, —$N_3$, —CN, —$SO_{n1}R^{1A}$, —$SO_{v1}NR^{1B}R^{1C}$, —$NR^{1B}R^{1C}$, —$C(O)R^{1D}$, —$C(O)OR^{1D}$, —$C(O)NR^{1B}R^{1C}$, —$OR^{1A}$, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^2$ is hydrogen;

$R^3$ is independently hydrogen, halogen, —$CX^3_3$, —$CHX^3_2$, —$CH_2X^3$, —$N_3$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^3_3$, —$OCHX^3_2$, —$OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, at least one of $R^3$ is not hydrogen;

$R^4$ is hydrogen, halogen, oxo, —$CX^4_3$, —$CHX^4_2$, —$CH_2X^4$, —CN, —$SO_{n4}R^{4A}$, —$SO_{v4}NR^{4B}R^{4C}$, —$NR^{4B}R^{4C}$, —$C(O)R^{4D}$, —$C(O)OR^{4D}$, —$C(O)NR^{4B}R^{4C}$, —$OR^{4A}$, —$OCX^4_3$, —$OCHX^4_2$, —$OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is hydrogen, halogen, oxo, —$CX^6_3$, —$CHX^6_2$, —$CH_2X^6$, —$N_3$, —CN, —$SO_{n6}R^{6A}$, —$SO_{v6}NR^{6B}R^{6C}$, —$NR^{6B}R^{6C}$, —$C(O)R^{6D}$, —$C(O)OR^{6D}$, —$C(O)NR^{6B}R^{6C}$, —$OR^{6A}$, —$OCX^6_3$, —$OCHX^6_2$, —$OCH_2X^6$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$ and $R^{6D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$ and $R^{6B}$ and $R^{6C}$ substituents bonded to the same nitrogen atom may optionally be joined to form a substituted or unsubstituted heterocycloalkyl or substituted or unsubstituted heteroaryl; and $X^1$, $X^2$, $X^3$, $X^4$ and $X^6$ are independently —Cl, —Br, —I or —F, provided that when X is =O and Y is =O, then at least one of $R^2$, $R^3$ and $R^4$ is not hydrogen.

2. The compound of claim 1, wherein:
R⁴ is hydrogen or substituted or unsubstituted alkyl; and
X is =O.

3. The compound of claim 2, wherein the compound has structural Formula (I-A):

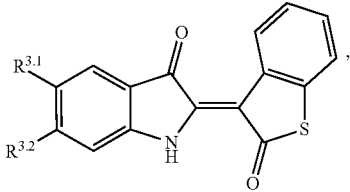

(I-A)

wherein:
n3.1 and n3.2 are independently an integer from 0 to 4;
m3.1, m3.2, v3.1 and v3.2 are independently 1 or 2;
$R^{3.1}$ is hydrogen, halogen, —$CX^{3.1}_3$, —$CHX^{3.1}_2$, —$CH_2X^{3.1}$, —$N_3$, —CN, —$SO_{n3.1}R^{3.1A}$, —$SO_{v3.1}NR^{3.1B}R^{3.1C}$, —$NHNR^{3.1B}R^{3.1C}$, —$ONR^{3.1B}R^{3.1C}$, —$NHC(O)NHNR^{3.1B}R^{3.1C}$, —$NHC(O)NR^{3.1B}R^{3.1C}$, —$N(O)_{m3.1}$, —$NR^{3.1B}R^{3.1C}$, —$C(O)R^{3.1D}$, —$C(O)OR^{3.1D}$, —$C(O)NR^{3.1B}R^{3.1C}$, —$OR^{3.1A}$, —$NR^{3.1B}SO_2R^{3.1A}$, —$NR^{3.1B}C(O)R^{3.1D}$, —$NR^{3.1B}C(O)OR^{3.1D}$, —$NR^{3.1B}OR^{3.1D}$, —$OCX^{3.1}_3$, —$OCHX^{3.1}_2$, —$OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, —$CX^{3.2}_3$, —$CHX^{3.2}_2$, —$CH_2X^{3.2}$, —$N_3$, —CN, —$SO_{n3.2}R^{3.2A}$, —$SO_{v3.2}NR^{3.2B}R^{3.2C}$, —$NHNR^{3.2B}R^{3.2C}$, —$ONR^{3.2B}R^{3.2C}$, —$NHC(O)NHNR^{3.2B}R^{3.2C}$, —$NHC(O)NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}_3$, —$OCHX^{3.2}_2$, —$OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^{3.1}$ and $R^{3.2}$ is not hydrogen;
$R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, —$CF_3$, —$CCl_3$, —$CBr_3$, —$CI_3$—COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$ and $R^{3.2B}$ and $R^{3.2C}$ substituents bonded to the same nitrogen atom may optionally be joined to form a substituted or unsubstituted heterocycloalkyl or substituted or unsubstituted heteroaryl; and
$X^{3.1}$ and $X^{3.2}$ are independently —Cl, —Br, —I or —F.

4. The compound of claim 1, wherein X is =NR¹ and wherein R¹ is —OH.

5. The compound of claim 1, or a pharmaceutically acceptable salt thereof, wherein the compound has structural Formula (I-B):

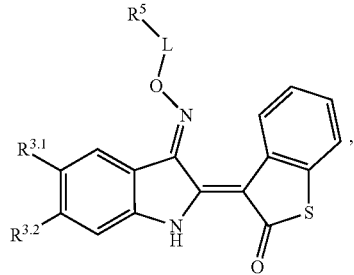

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^{3.1}$ is hydrogen, halogen, —$CX^{3.1}_3$, —$CHX^{3.1}_2$, —$CH_2X^{3.1}$, —$N_3$, —CN, —$SO_{n3.1}R^{3.1A}$, —$SO_{v3.1}NR^{3.1B}R^{3.1C}$, —$NHNR^{3.1B}R^{3.1C}$, —$ONR^{3.1B}R^{3.1C}$, —$NHC(O)NHNR^{3.1B}R^{3.1C}$, —$NHC(O)NR^{3.1B}R^{3.1C}$, —$N(O)_{m3.1}$, —$NR^{3.1B}R^{3.1C}$, —$C(O)R^{3.1D}$, —$C(O)OR^{3.1D}$, —$C(O)NR^{3.1B}R^{3.1C}$, —$OR^{3.1A}$, —$NR^{3.1B}SO_2R^{3.1A}$, —$NR^{3.1B}C(O)R^{3.1D}$, —$NR^{3.1B}C(O)OR^{3.1D}$, —$NR^{3.1B}OR^{3.1D}$, —$OCX^{3.1}_3$, —$OCHX^{3.1}_2$, —$OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, —$CX^{3.2}_3$, —$CHX^{3.2}_2$, —$CH_2X^{3.2}$, —$N_3$, —CN, —$SO_{n3.2}R^{3.2A}$, —$SO_{v3.2}NR^{3.2B}R^{3.2C}$, —$NHNR^{3.2B}R^{3.2C}$, —$ONR^{32B}R^{32C}$, —$NHC(O)NHNR^{3.2B}R^{3.2C}$, —$NHC(O)NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}_3$, —$OCHX^{3.2}_2$, —$OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^{3.1}$ and $R^{3.2}$ is not hydrogen;
$R^5$ is hydrogen, halogen, —$CX^5_3$, —$CHX^5_2$, —$CH_2X^5$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^5_3$, —$OCHX^5_2$, —$OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —$CF_3$, —$CCl_3$, —$CBr_3$, —$CI_3$—COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently —Cl, —Br, —I or —F.

6. The compound of claim 3, wherein $R^{3.1}$ and $R^{3.2}$ are independently hydrogen, halogen, —CN, substituted or unsubstituted alkyl or substituted or unsubstituted heteroalkyl.

7. The compound of claim 5, wherein $R^{3.1}$ and $R^{3.2}$ are independently hydrogen, halogen, —CN, substituted or unsubstituted alkyl or substituted or unsubstituted heteroalkyl; and L is unsubstituted alkylene or a bond.

8. The compound of claim 5, wherein:

$R^5$ is hydrogen, halogen, —$CX^5{}_3$, —$OCX^5{}_3$, —CN, —OH, —$NH_2$, —COOH, —$C(O)OR^{5D}$, —$CONH_2$, —$NO_2$, SH, —$NHNH_2$, —$NR^{5B}R^{5C}$, —$OR^{5A}$, —$SR^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.1}$ or $R^{3.2}$ is —Cl, —Br, —I or —F; and $R^{5B}$ and $R^{5C}$ are independently substituted or unsubstituted alkyl, substituted or I unsubstituted heteroalkyl, substituted or unsubstituted cycloalkyl, substituted or unsubstituted heterocycloalkyl, substituted or unsubstituted aryl or substituted or unsubstituted heteroaryl; or $R^{5B}$ and $R^{5C}$ are joined together to form a substituted or unsubstituted heterocycloalkyl or I substituted or unsubstituted heteroaryl.

9. The compound of claim 8, wherein $R^{5B}$ and $R^{5C}$ are joined together to form a substituted or unsubstituted pyrrolidinyl, a substituted or unsubstituted piperazinyl, or a substituted or unsubstituted morphorinyl.

10. The compound of claim 9, wherein the compound has structural formula (IV-A) or (IV-B):

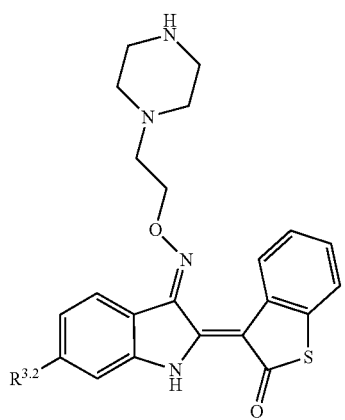

(IV-A)

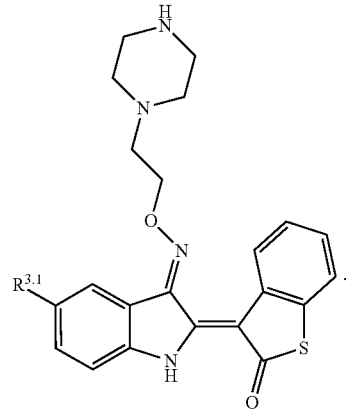

(IV-B)

11. The compound of claim 10, wherein each $R^{3.1}$ and $R^{3.2}$ is independently —C(O)H, —$C(O)CH_3$, C(O)OH, or —$C(O)OCH_3$.

12. The compound of claim 1, wherein the compound is:

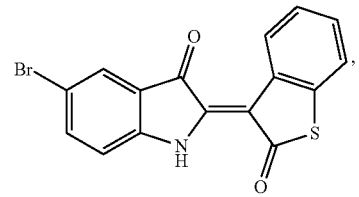

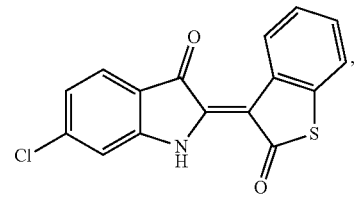

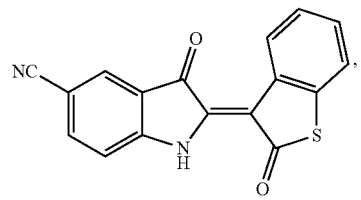

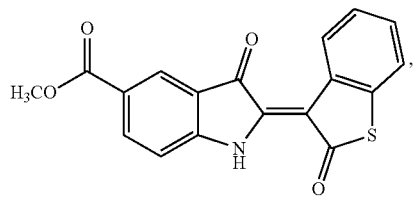

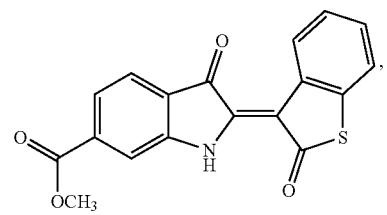

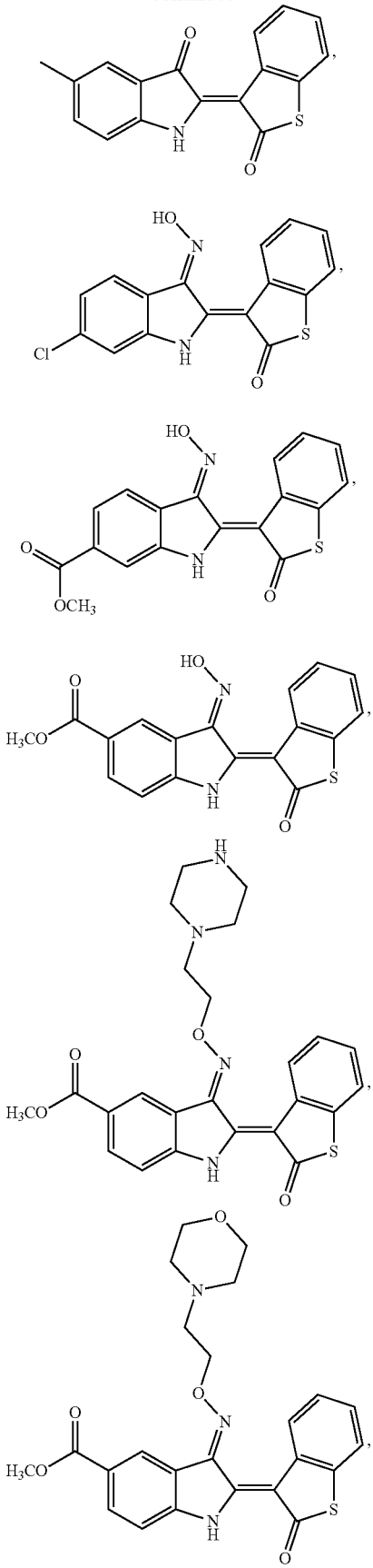

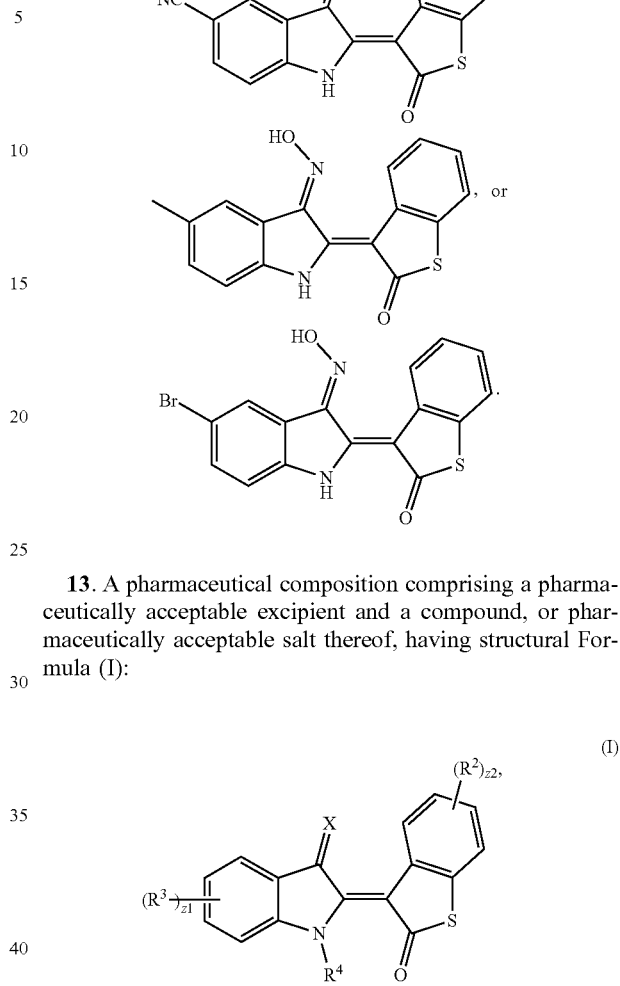

13. A pharmaceutical composition comprising a pharmaceutically acceptable excipient and a compound, or pharmaceutically acceptable salt thereof, having structural Formula (I):

wherein:
n1, n2, n3 and n4 are independently an integer from 0 to 4;
m2, m3, v1, v2, v3 and v4 are independently 1 or 2;
z1 and z2 are independently an integer from 1 to 4;
X is =O, =S or =NR$^1$;
R$^1$ is hydrogen, halogen, —CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^2$ is hydrogen;
R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^3$ is not hydrogen;

$R^4$ is hydrogen, halogen, $-CX^4{}_3$, $-CHX^4{}_2$, $-CH_2X^4$, $-CN$, $-SO_{n4}R^{4A}$, $-SO_{v4}NR^{4B}R^{4C}$, $-NR^{4B}R^{4C}$, $-C(O)R^{4D}$, $-C(O)OR^{4D}$, $-C(O)NR^{4B}R^{4C}$, $-OR^{4A}$, $-OCX^4{}_3$, $-OCHX^4{}_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently $-Cl$, $-Br$, $-I$ or $-F$.

14. The pharmaceutical composition of claim 13, wherein:
$R^4$ is hydrogen or substituted or unsubstituted alkyl; and
X is =O.

15. The pharmaceutical composition of claim 14 wherein the compound has structural Formula (I-A):

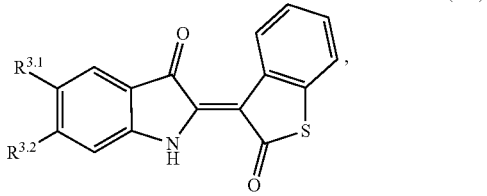

(I-A)

wherein:
n3.1 and n3.2 are independently an integer from 0 to 4;
m3.1, m3.2, v3.1 and v3.2 are independently 1 or 2;
$R^{3.1}$ is hydrogen, halogen, $-CX^{3.1}{}_3$, $-CHX^{3.1}{}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}{}_3$, $-OCHX^{3.1}{}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}{}_3$, $-CHX^{3.2}{}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}{}_3$, $-OCHX^{3.2}{}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^{3.1}$ and $R^{3.2}$ is not hydrogen;

$R^{3.1A}$, $R^{3.1B}$, $R^{3.1C}$, $R^{3.1D}$, $R^{3.2A}$, $R^{3.2B}$, $R^{3.2C}$ and $R^{3.2D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$ and $R^{3.2B}$ and $R^{3.2C}$ substituents bonded to the same nitrogen atom may optionally be joined to form a substituted or unsubstituted heterocycloalkyl or substituted or unsubstituted heteroaryl; and $X^{3.1}$ and $X^{3.2}$ are independently $-Cl$, $-Br$, $-I$ or $-F$.

16. The pharmaceutical composition of claim 13, wherein X is $=NR^1$ and $R^1$ is $-OH$.

17. The pharmaceutical composition of claim 13, wherein the compound has structural Formula (I-B):

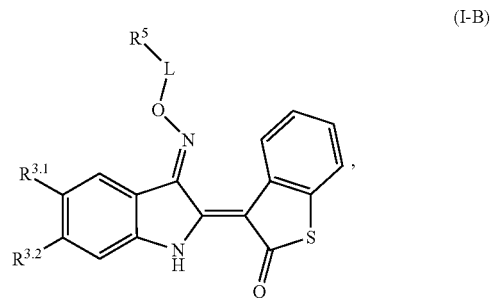

(I-B)

wherein:
n3.1, n3.2 and n5 are independently an integer from 0 to 4;
m3.1, m3.2, m5, v3.1, v3.2 and v5 are independently 1 or 2;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^{3.1}$ is hydrogen, halogen, $-CX^{3.1}{}_3$, $-CHX^{3.1}{}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}{}_3$, $-OCHX^{3.1}{}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}{}_3$, $-CHX^{3.2}{}_2$, $-CH_2X^{3.2}$, $-N_3$, $-CN$, $-SO_{n3.2}R^{3.2A}$, —SO$_{v3.2}$NR$^{3.2B}$R$^{3.2C}$, —NHNR$^{3.2B}$R$^{3.2C}$, —ONR$^{32B}$R$^{32C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of R$^{3.1}$ and R$^{3.2}$ is not hydrogen;

R$^5$ is hydrogen, halogen, —CX$^5_3$, —CHX$^5_2$, —CH$_2$X$^5$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^5_3$, —OCHX$^5_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.1A}$, R$^{3.1B}$, R$^{3.1C}$, R$^{3.1D}$, R$^{3.2A}$, R$^{3.2B}$, R$^{3.2C}$, R$^{3.2D}$, R$^{5A}$, R$^{5B}$, R$^{5C}$ and R$^{5D}$ are independently hydrogen, halogen, —CF$_3$, —CCl$_3$, —CBr$_3$, —CI$_3$—COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.1B}$ and R$^{3.1C}$, R$^{3.2B}$ and R$^{3.2C}$, and R$^{5B}$ and R$^{5C}$ substituents bonded to the same nitrogen atom may optionally be joined to form a substituted or unsubstituted heterocycloalkyl or substituted or unsubstituted heteroaryl; and X$^{3.1}$, X$^{3.2}$ and X$^5$ are independently —Cl, —Br, —I or —F.

18. The pharmaceutical composition of claim 17, wherein R$^{3.1}$ and R$^{3.2}$ are independently hydrogen, halogen, —CN, substituted or unsubstituted alkyl or substituted or unsubstituted heteroalkyl; and L is unsubstituted alkylene or a bond.

19. The pharmaceutical composition of claim 17, wherein:

R$^5$ is hydrogen, halogen, —CX$^5_3$, —OCX$^5_3$, —CN, —OH, —NH$_2$, —COOH, —C(O)OR$^{5D}$, —CONH$_2$, —NO$_2$, SH, —NHNH$_2$, —NR$^{5B}$R$^{5C}$, —OR$^{5A}$, —SR$^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{3.1}$ or R$^{3.2}$ is —Cl, —Br, —I or —F; and

R$^{5B}$ and R$^{5C}$ are independently substituted or unsubstituted alkyl, substituted or I unsubstituted heteroalkyl, substituted or unsubstituted cycloalkyl, substituted or unsubstituted heterocycloalkyl, substituted or unsubstituted aryl or substituted or unsubstituted heteroaryl; or R$^{5B}$ and R$^{5C}$ are joined together to form a substituted or unsubstituted heterocycloalkyl or I substituted or unsubstituted heteroaryl.

20. The pharmaceutical composition of claim 19, wherein R$^{5B}$ and R$^{5C}$ are joined together to form a substituted or unsubstituted pyrrolidinyl, wherein L is unsubstituted alkylene, or a substituted or unsubstituted morphorinyl.

21. The pharmaceutical composition of claim 20, wherein the compound has structural formula (IV-A) or (IV-B):

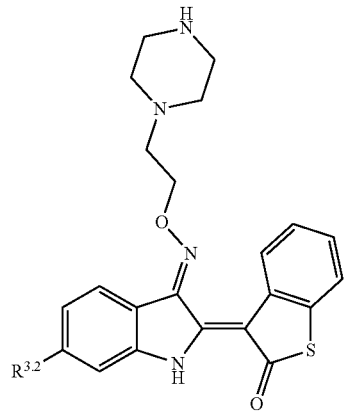

(IV-A)

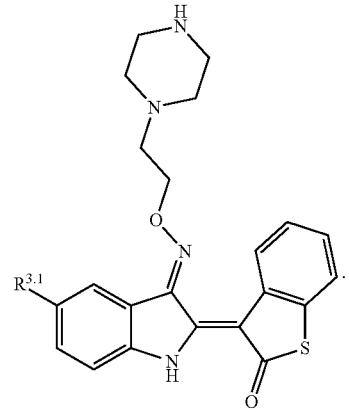

(IV-B)

22. The pharmaceutical composition of claim 21, wherein each R$^{3.1}$ and R$^{3.2}$ is independently —C(O)H, —C(O)CH$_3$, C(O)OH, or —C(O)OCH$_3$.

23. The pharmaceutical composition of claim 13, wherein the compound is:

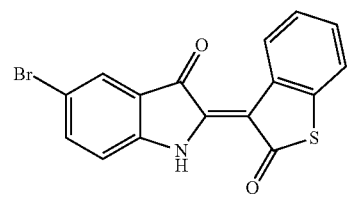

,

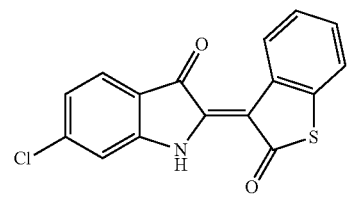

,

-continued
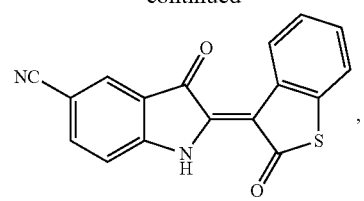,
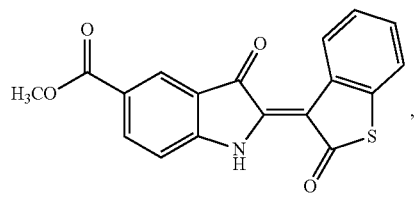,
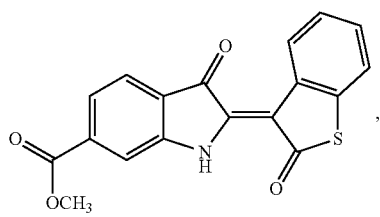,
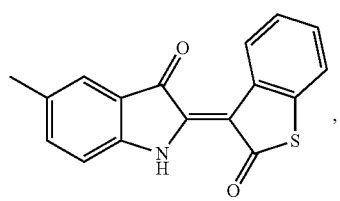,
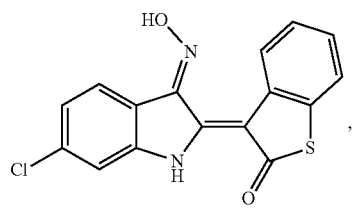,
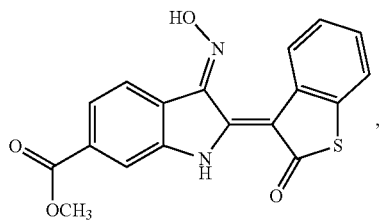,
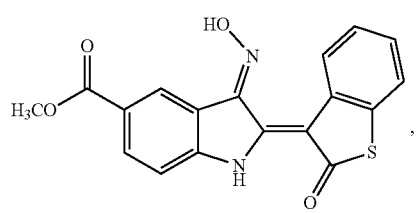,
-continued
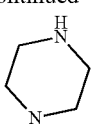
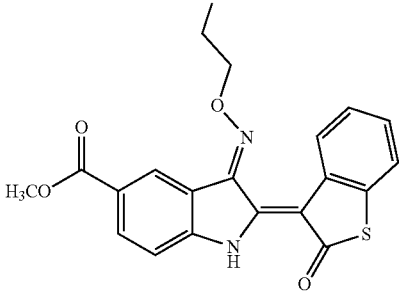,
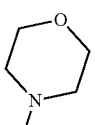
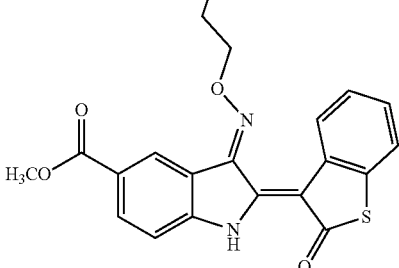,
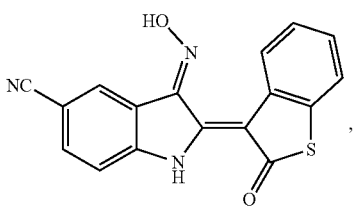,
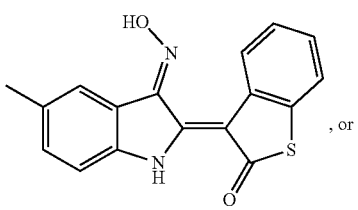, or
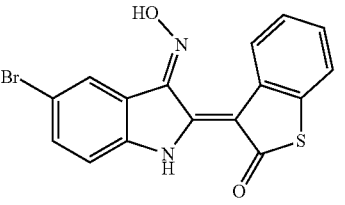.
24. A method of treating cancer, comprising administering to a subject in need thereof a therapeutically effective amount of a compound, or pharmaceutically acceptable salt thereof, having structural Formula (I):

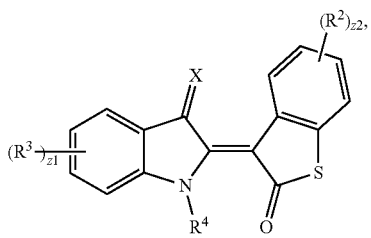

(I)

wherein:
n1, n2, n3 and n4 are independently an integer from 0 to 4;
m2, m3, m5, v1, v2, v3 and v4 are independently 1 or 2;
z1 and z2 are independently an integer from 1 to 4;
X is =O, =S or =NR$^1$;
R$^1$ is hydrogen, halogen —CX$^1_3$, —CHX$^1_2$, —CH$_2$X$^1$, —N$_3$, —CN, —SO$_{n1}$R$^{1A}$, —SO$_{v1}$NR$^{1B}$R$^{1C}$, —NR$^{1B}$R$^{1C}$, —C(O)R$^{1D}$, —C(O)OR$^{1D}$, —C(O)NR$^{1B}$R$^{1C}$, —OR$^{1A}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^2$ is hydrogen;
R$^3$ is independently hydrogen, halogen, —CX$^3_3$, —CHX$^3_2$, —CH$_2$X$^3$, —N$_3$, —CN, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of R$^3$ is not hydrogen;
R$^4$ is hydrogen, halogen, —CX$^4_3$, —CHX$^4_2$, —CH$_2$X$^4$, —CN, —SO$_{n4}$R$^{4A}$, —SO$_{v4}$NR$^{4B}$R$^{4C}$, —NR$^{4B}$R$^{4C}$, —C(O)R$^{4D}$, —C(O)OR$^{4D}$, —C(O)NR$^{4B}$R$^{4C}$, —OR$^{4A}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$ and R$^{4B}$ and R$^{4C}$ substituents bonded to the same nitrogen atom may optionally be joined to form a substituted or unsubstituted heterocycloalkyl or substituted or unsubstituted heteroaryl; and
X$^1$, X$^2$, X$^3$ and X$^4$ are independently —Cl, —Br, —I or —F,
wherein the subject in need thereof has cancer.

25. The method of claim 24, wherein the compound has structural Formula (I-A) or (I-B):

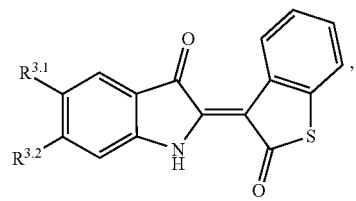

(I-A)

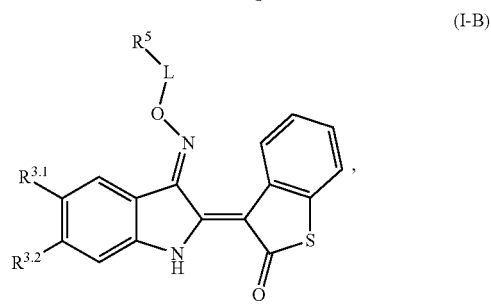

(I-B)

wherein:
n3.1, n3.2, and n5 are independently an integer from 0 to 4;
m3.1, m3.2, m5, v3.1, v3.2, and v5 are independently 1 or 2;
R$^{3.1}$ is hydrogen, halogen, —CX$^{3.1}_3$, —CHX$^{3.1}_2$, —CH$_2$X$^{3.1}$, —N$_3$, —CN, —SO$_{n3.1}$R$^{3.1A}$, —SO$_{v3.1}$NR$^{3.1B}$R$^{3.1C}$, —NHNR$^{3.1B}$R$^{3.1C}$, —ONR$^{3.1B}$R$^{3.1C}$, —NHC(O)NHNR$^{3.1B}$R$^{3.1C}$, —NHC(O)NR$^{3.1B}$R$^{3.1C}$, —N(O)$_{m3.1}$, —NR$^{3.1B}$R$^{3.1C}$, —C(O)R$^{3.1D}$, —C(O)OR$^{3.1D}$, —C(O)NR$^{3.1B}$R$^{3.1C}$, —OR$^{3.1A}$, —NR$^{3.1B}$SO$_2$R$^{3.1A}$, —NR$^{3.1B}$C(O)R$^{3.1D}$, —NR$^{3.1B}$C(O)OR$^{3.1D}$, —NR$^{3.1B}$OR$^{3.1D}$, —OCX$^{3.1}_3$, —OCHX$^{3.1}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R$^{3.2}$ is hydrogen, halogen, —CX$^{3.2}_3$, —CHX$^{3.2}_2$, —CH$_2$X$^{3.2}$, —N$_3$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of R$^{3.1}$ and R$^{3.2}$ is not hydrogen;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
R$^5$ is hydrogen, halogen, —CX$^5_3$, —CHX$^5_2$, —CH$_2$X$^5$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)

$NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^5{}_3$, —$OCHX^5{}_2$, —$OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently —Cl, —Br, —I or —F.

26. The method of claim 24, wherein the cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, a solid tumor or a blood tumor.

27. The method of claim 24, wherein the compound is co-administered with an effective amount of an anti-cancer agent.

28. A method of modulating a kinase, comprising contacting the kinase with a compound, or pharmaceutically acceptable salt thereof, having structural Formula (I):

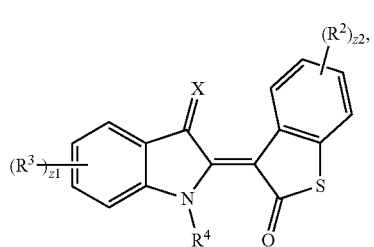

(I)

wherein:
n1, n2, n3 and n4 are independently an integer from 0 to 4;
m2, m3, v1, v2, v3 and v4 are independently 1 or 2;
z1 and z2 are independently an integer from 1 to 4;
X is =O, =S or =$NR^1$;
$R^1$ is hydrogen, halogen, —$CX^1{}_3$, —$CHX^1{}_2$, —$CH_2X^1$, —$N_3$, —CN, —$SO_{n1}R^{1A}$, —$SO_{v1}NR^{1B}R^{1C}$, —$NR^{1B}R^{1C}$, —$C(O)R^{1D}$, —$C(O)OR^{1D}$, —$C(O)NR^{1B}R^{1C}$, —$OR^{1A}$, —$OCX^1{}_3$, —$OCHX^1{}_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^2$ is hydrogen;
$R^3$ is independently hydrogen, halogen, —$CX^3{}_3$, —$CHX^3{}_2$, —$CH_2X^3$, —$N_3$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^3{}_3$, —$OCHX^3{}_2$, —$OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^3$ is not hydrogen;

$R^4$ is hydrogen, halogen, —$CX^4{}_3$, —$CHX^4{}_2$, —$CH_2X^4$, —CN, —$SO_{n4}R^{4A}$, —$SO_{v4}NR^{4B}R^{4C}$, —$NR^{4B}R^{4C}$, —$C(O)R^{4D}$, —$C(O)OR^{4D}$, —$C(O)NR^{4B}R^{4C}$, —$OR^{4A}$, —$OCX^4{}_3$, —$OCHX^4{}_2$, —$OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently —Cl, —Br, —I or —F.

29. The method of claim 28, wherein the compound has structural Formula (I-A) or (I-B):

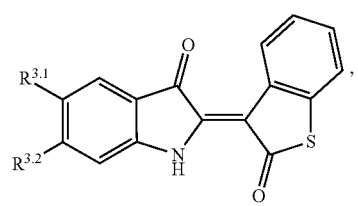

(I-A)

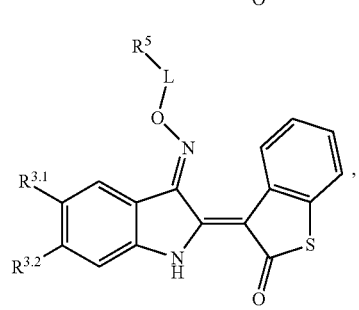

(I-B)

wherein:
n3.1, n3.2, and n5 are independently an integer from 0 to 4;
m3.1, m3.2, m5, v3.1, v3.2, and v5 are independently 1 or 2;
$R^{3.1}$ is hydrogen, halogen, —$CX^{3.1}{}_3$, —$CHX^{3.1}{}_2$, —$CH_2X^{3.1}$, —$N_3$, —CN, —$SO_{n3.1}R^{3.1A}$, —$SO_{v3.1}NR^{3.1B}R^{3.1C}$, —$NHNR^{3.1B}R^{3.1C}$, —$ONR^{3.1B}R^{3.1C}$, —$NHC(O)NHNR^{3.1B}R^{3.1C}$, —NHC(O)

$NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^{3.1}$ and $R^{3.2}$ is not hydrogen;

L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^5$ is hydrogen, halogen, $-CX^5_3$, $-CHX^5_2$, $-CH_2X^5$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and $X^{3.1}$, $X^{3.2}$ and $X^5$ are independently $-Cl$, $-Br$, $-I$ or $-F$.

30. The method of claim 28, wherein the kinase is JAK, JAK2, TYK2, Src, c-Src, ABL1, ABL1 T315I, an Aurora kinase, GSK-3b or a CDK; and the Aurora kinase is Aurora A.

31. A method of modulating STAT or STAT3, comprising contacting STAT or STAT3 with a compound, or pharmaceutically acceptable salt thereof, having structural Formula (I):

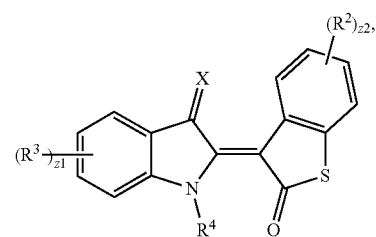

wherein:

n1, n2, n3 and n4 are independently an integer from 0 to 4;

m2, m3, v1, v2, v3 and v4 are independently 1 or 2;

z1 and z2 are independently an integer from 1 to 4;

X is $=O$, $=S$ or $=NR^1$;

$R^1$ is hydrogen, halogen, $-CX^1_3$, $-CHX^1_2$, $-CH_2X^1$, $-N_3$, $-CN$, $-SO_{n1}R^{1A}$, $-SO_{v1}NR^{1B}R^{1C}$, $-NR^{1B}R^{1C}$, $-C(O)R^{1D}$, $-C(O)OR^{1D}$, $-C(O)NR^{1B}R^{1C}$, $-OR^{1A}$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^2$ is hydrogen;

$R^3$ is independently hydrogen, halogen, $-CX^3_3$, $-CHX^3_2$, $-CH_2X^3$, $-N_3$, $-CN$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^3_3$, $-OCHX^3_2$, $-OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^3$ is not hydrogen;

$R^4$ is hydrogen, halogen, $-CX^4_3$, $-CHX^4_2$, $-CH_2X^4$, $-CN$, $-SO_{n4}R^{4A}$, $-SO_{v4}NR^{4B}R^{4C}$, $-NR^{4B}R^{4C}$, $-C(O)R^{4D}$, $-C(O)OR^{4D}$, $-C(O)NR^{4B}R^{4C}$, $-OR^{4A}$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$ and $R^{4B}$ and $R^{4C}$ substituents bonded to the same nitrogen atom may optionally be joined to form a substituted or unsubstituted heterocycloalkyl or substituted or unsubstituted heteroaryl; and $X^1$, $X^2$, $X^3$ and $X^4$ are independently $-Cl$, $-Br$, $-I$ or $-F$.

32. The method of claim 31, wherein the compound has structural Formula (I-A) or (I-B):

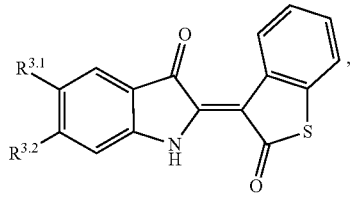

(I-A)

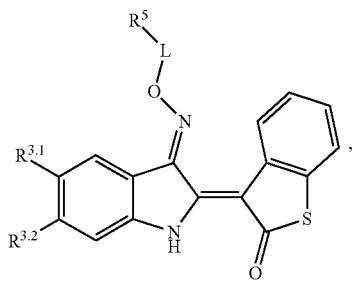

(I-B)

wherein:
n3.1, n3.2, and n5 are independently an integer from 0 to 4;
m3.1, m3.2, m5, v3.1, v3.2, and v5 are independently 1 or 2;
$R^{3.1}$ is hydrogen, halogen, $-CX^{3.1}_3$, $-CHX^{3.1}_2$, $-CH_2X^{3.1}$, $-N_3$, $-CN$, $-SO_{n3.1}R^{3.1A}$, $-SO_{v3.1}NR^{3.1B}R^{3.1C}$, $-NHNR^{3.1B}R^{3.1C}$, $-ONR^{3.1B}R^{3.1C}$, $-NHC(O)NHNR^{3.1B}R^{3.1C}$, $-NHC(O)NR^{3.1B}R^{3.1C}$, $-N(O)_{m3.1}$, $-NR^{3.1B}R^{3.1C}$, $-C(O)R^{3.1D}$, $-C(O)OR^{3.1D}$, $-C(O)NR^{3.1B}R^{3.1C}$, $-OR^{3.1A}$, $-NR^{3.1B}SO_2R^{3.1A}$, $-NR^{3.1B}C(O)R^{3.1D}$, $-NR^{3.1B}C(O)OR^{3.1D}$, $-NR^{3.1B}OR^{3.1D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^{3.2}$ is hydrogen, halogen, $-CX^{3.2}_3$, $-CHX^{3.2}_2$, $-CH_2X^{3.2}$, $-N_3$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $-OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein at least one of $R^{3.1}$ and $R^{3.2}$ is not hydrogen;
L is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$R^5$ is hydrogen, halogen, $-CX^5_3$, $-CHX^5_2$, $-CH_2X^5$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3.1A}$, $R^{3.1B}$, $R^{3.1C}$, $R^{3.1D}$, $R^{3.2A}$, $R^{3.2B}$, $R^{3.2C}$, $R^{3.2D}$, $R^{5A}$, $R^{5B}$, $R^{5C}$ and $R^{5D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1B}$ and $R^{3.1C}$, $R^{3.2B}$ and $R^{3.2C}$, and $R^{5B}$ and $R^{5C}$ substituents bonded to the same nitrogen atom may optionally be joined to form a substituted or unsubstituted heterocycloalkyl or substituted or unsubstituted heteroaryl; and
$X^{3.1}$, $X^{3.2}$, and $X^5$ are independently —Cl, —Br, —I or —F.

* * * * *